US009782493B2

(12) United States Patent
Vlahov et al.

(10) Patent No.: US 9,782,493 B2
(45) Date of Patent: Oct. 10, 2017

(54) CONJUGATES FOR TREATING DISEASES CAUSED BY PSMA EXPRESSING CELLS

(71) Applicant: ENDOCYTE, INC., West Lafayette, IN (US)

(72) Inventors: Iontcho Radoslavov Vlahov, West Lafayette, IN (US); Joseph Anand Reddy, West Lafayette, IN (US); Alicia Bloomfield, Lafayette, IN (US); Ryan Dorton, Lafayette, IN (US); Melissa Nelson, Delphi, IN (US); Marilynn Vetzel, Rossville, IN (US); Christopher Paul Leamon, West Lafayette, IN (US)

(73) Assignee: ENDOCYTE, INC., West Lafayette, IN (US)

( * ) Notice: Subject to any disclaimer, the term of this patent is extended or adjusted under 35 U.S.C. 154(b) by 0 days.

(21) Appl. No.: 15/245,505

(22) Filed: Aug. 24, 2016

(65) Prior Publication Data

US 2016/0361376 A1 Dec. 15, 2016

Related U.S. Application Data

(62) Division of application No. 14/443,212, filed as application No. PCT/US2013/070007 on Nov. 14, 2013.

(60) Provisional application No. 61/875,971, filed on Sep. 10, 2013, provisional application No. 61/788,382, filed on Mar. 15, 2013, provisional application No. 61/726,991, filed on Nov. 15, 2012.

(51) Int. Cl.
| | |
|---|---|
| *A61K 47/48* | (2006.01) |
| *A61K 38/06* | (2006.01) |
| *A61K 38/05* | (2006.01) |
| *A61P 35/00* | (2006.01) |
| *A61K 49/00* | (2006.01) |
| *A61K 38/07* | (2006.01) |
| *A61K 38/08* | (2006.01) |
| *C07K 5/10* | (2006.01) |
| *C07K 5/02* | (2006.01) |
| *C07K 5/11* | (2006.01) |
| *C07K 5/072* | (2006.01) |
| *A61K 38/00* | (2006.01) |

(52) U.S. Cl.
CPC ........ *A61K 47/48246* (2013.01); *A61K 38/05* (2013.01); *A61K 38/06* (2013.01); *A61K 38/07* (2013.01); *A61K 38/08* (2013.01); *A61K 47/48023* (2013.01); *A61K 47/48038* (2013.01); *A61K 49/0002* (2013.01); *C07K 5/021* (2013.01); *C07K 5/06113* (2013.01); *C07K 5/10* (2013.01); *C07K 5/1019* (2013.01); *A61K 38/00* (2013.01)

(58) Field of Classification Search
CPC ........ A61K 47/48246; A61K 47/48038; A61K 49/0002; A61K 38/05; A61K 47/48023; A61K 38/06; A61K 38/07; A61K 38/08; A61K 38/00; C07K 5/10; C07K 5/021; C07K 5/1019; C07K 5/06113
See application file for complete search history.

(56) References Cited

U.S. PATENT DOCUMENTS

| | | |
|---|---|---|
| 4,691,024 A | 9/1987 | Shirahata et al. |
| 4,713,249 A | 12/1987 | Schroder |
| 5,103,018 A | 4/1992 | Motomichi et al. |
| 5,266,333 A | 11/1993 | Cady et al. |
| 5,418,982 A | 5/1995 | Kishi |
| 5,627,165 A | 5/1997 | Glazier |
| 5,795,877 A | 8/1998 | Jackson et al. |
| 5,863,536 A | 1/1999 | Jackson et al. |
| 5,866,679 A | 2/1999 | DeFeo-Jones et al. |
| 5,902,817 A | 5/1999 | Jackson et al. |
| 5,948,750 A | 9/1999 | Garsky et al. |
| 5,962,237 A | 10/1999 | Ts'o et al. |
| 5,962,521 A | 10/1999 | Jackson et al. |
| 5,968,915 A | 10/1999 | Jackson et al. |
| 5,998,362 A | 12/1999 | Feng et al. |
| 6,054,444 A | 4/2000 | Jackson et al. |
| 6,127,333 A | 10/2000 | Brady et al. |
| 6,174,858 B1 | 1/2001 | Brady et al. |
| 6,177,404 B1 | 1/2001 | DeFeo-Jones et al. |
| 6,232,287 B1 | 5/2001 | Ruoslahti et al. |
| 6,368,598 B1 | 4/2002 | D'Amico et al. |
| 6,391,305 B1 | 5/2002 | Feng et al. |
| 6,428,785 B1 | 8/2002 | Gokcen |

(Continued)

FOREIGN PATENT DOCUMENTS

| | | |
|---|---|---|
| CA | 2606138 | 10/2005 |
| EP | 0116208 | 8/1984 |

(Continued)

OTHER PUBLICATIONS

Kularatne et al., "Prostate-specific membrane antigen targeted imaging and therapy of prostate cancer using a PSMA inhibitor as a homing ligand," *Molecular Pharmaceutics*, 6(3): 780-789 (2009).
Pubchem, Compound summary for: CID 58099954 (Aug. 19, 2012).
Reddy et al., "PSMA-specific anti-tumor activity of the targeted-tubulysin conjugate, EC1169," *American Association for Cancer Research Annual Meeting* (Apr. 8, 2013) Poster.
Reddy et al., "PSMA-specific anti-tumor activity of the targeted-tubulysin conjugate, EC1169," *American Association for Cancer Research Annual Meeting* (Apr. 8, 2013) Presentation Abstract.

(Continued)

*Primary Examiner* — Julie Ha
*Assistant Examiner* — Li Ni Komatsu
(74) *Attorney, Agent, or Firm* — Barnes & Thornburg LLP; Gregory H. Zayia

(57) ABSTRACT

The invention described herein pertains to the diagnosis, imaging, and/or treatment of pathogenic cell populations. In particular, the invention described herein pertains to the diagnosis, imaging, and/or treatment of diseases caused by PSMA expressing cells, such as prostate cancer cells, using compounds capable of targeting PSMA expressing cells.

19 Claims, 6 Drawing Sheets

(56) References Cited

U.S. PATENT DOCUMENTS

| | | |
|---|---|---|
| 6,479,470 B1 | 11/2002 | Kozikowski et al. |
| 6,528,499 B1 | 3/2003 | Kozikowski et al. |
| 6,875,886 B2 | 4/2005 | Frangioni |
| 6,946,133 B1 | 9/2005 | Schlom et al. |
| 7,008,765 B1 | 3/2006 | Bussemakers et al. |
| 7,128,893 B2 | 10/2006 | Leamon et al. |
| 7,129,254 B2 | 10/2006 | Berger et al. |
| 7,147,837 B2 | 12/2006 | Lauffer et al. |
| 7,192,586 B2 | 3/2007 | Bander |
| 7,232,805 B2 | 6/2007 | Weinshenker et al. |
| 7,361,338 B2 | 4/2008 | Jakobovits et al. |
| 7,381,745 B2 | 6/2008 | Kozikowski et al. |
| 7,408,079 B2 | 8/2008 | Pomper et al. |
| 7,485,299 B2 | 2/2009 | Afar et al. |
| 7,514,078 B2 | 4/2009 | Bander et al. |
| 7,534,580 B2 | 5/2009 | Reeves et al. |
| 7,601,332 B2 | 10/2009 | Vlahov et al. |
| 7,635,682 B2 | 12/2009 | Denmeade et al. |
| 7,638,122 B2 | 12/2009 | Yu et al. |
| 7,659,395 B2 | 2/2010 | Pajouhesh et al. |
| 7,662,795 B2 | 2/2010 | Rodriguez et al. |
| 7,696,185 B2 | 4/2010 | Berkman |
| 7,713,944 B2 | 5/2010 | Kinberger et al. |
| 7,740,847 B2 | 6/2010 | Allan et al. |
| 7,767,202 B2 | 8/2010 | Pardoll et al. |
| 7,767,803 B2 | 8/2010 | Diener et al. |
| 7,794,929 B2 | 9/2010 | Baylin et al. |
| 7,872,235 B2 | 1/2011 | Rousso et al. |
| 7,875,586 B2 | 1/2011 | Kovbasnjuk et al. |
| 7,879,981 B2 | 2/2011 | Obata |
| RE42,275 E | 4/2011 | Berkman |
| 7,990,533 B2 | 8/2011 | Maier et al. |
| 8,000,773 B2 | 8/2011 | Rousso et al. |
| 8,101,369 B2 | 1/2012 | Nam et al. |
| 8,101,713 B2 | 1/2012 | Cuello et al. |
| 8,105,568 B2 | 1/2012 | Vlahov et al. |
| 8,153,595 B2 | 4/2012 | Chen |
| 8,211,402 B2 | 7/2012 | Babich et al. |
| 8,211,473 B2 | 7/2012 | Troiano et al. |
| 8,211,635 B2 | 7/2012 | Barton |
| 8,258,111 B2 | 9/2012 | Shen et al. |
| 8,404,817 B2 | 3/2013 | Sherman et al. |
| 8,414,898 B2 | 4/2013 | Afar et al. |
| 8,445,851 B2 | 5/2013 | Rousso et al. |
| 8,450,290 B2 | 5/2013 | Worm et al. |
| 8,465,725 B2 | 6/2013 | Babich et al. |
| 8,487,129 B2 | 7/2013 | Babich et al. |
| 8,507,434 B2 | 8/2013 | Popel et al. |
| 8,557,772 B2 | 10/2013 | Popel et al. |
| 8,606,349 B2 | 12/2013 | Rousso et al. |
| 8,644,910 B2 | 2/2014 | Rousso et al. |
| 8,685,891 B2 | 4/2014 | Muraca |
| 8,703,918 B2 | 4/2014 | Colombatti et al. |
| 8,772,226 B2 | 7/2014 | Denmeade et al. |
| 8,772,459 B2 | 7/2014 | Ho et al. |
| 8,816,095 B2 | 8/2014 | Brown et al. |
| 8,852,630 B2 | 10/2014 | Spiegel et al. |
| 8,859,509 B2 | 10/2014 | Spiegel et al. |
| 8,877,970 B2 | 11/2014 | Zimmerman et al. |
| 8,907,058 B2 | 12/2014 | Low et al. |
| 8,940,871 B2 | 1/2015 | Wu et al. |
| 8,946,388 B2 | 2/2015 | Sahin et al. |
| 8,987,319 B2 | 3/2015 | Miller |
| 9,044,468 B2 | 6/2015 | Pomper et al. |
| 9,242,012 B2 | 1/2016 | Ma et al. |
| 9,278,067 B2 | 3/2016 | Boulikas |
| 2001/0031252 A1 | 10/2001 | Low et al. |
| 2002/0001782 A1 | 1/2002 | Watanabe et al. |
| 2002/0055121 A1 | 5/2002 | Vielkind |
| 2002/0103136 A1 | 8/2002 | Feng |
| 2002/0115596 A1 | 8/2002 | Garsky et al. |
| 2002/0132983 A1 | 9/2002 | Junghans |
| 2003/0035804 A1 | 2/2003 | D'Amico et al. |
| 2003/0086900 A1 | 5/2003 | Low et al. |
| 2003/0133927 A1 | 7/2003 | DeFeo-Jones et al. |
| 2003/0138432 A1 | 7/2003 | Glazier |
| 2003/0207808 A1 | 11/2003 | Savitzky et al. |
| 2003/0215456 A1 | 11/2003 | Yao et al. |
| 2003/0220241 A1 | 11/2003 | DeFeo-Jones et al. |
| 2003/0232760 A1 | 12/2003 | Garsky et al. |
| 2004/0001846 A1 | 1/2004 | Israeli et al. |
| 2004/0002478 A1 | 1/2004 | Kozikowski et al. |
| 2004/0018203 A1 | 1/2004 | Pastan et al. |
| 2004/0029778 A1 | 2/2004 | Isaacs |
| 2004/0033195 A1 | 2/2004 | Leamon et al. |
| 2004/0052727 A1 | 3/2004 | Dalton et al. |
| 2004/0054190 A1 | 3/2004 | Pomper et al. |
| 2004/0058857 A1 | 3/2004 | Yao |
| 2004/0110723 A1 | 6/2004 | Frangioni |
| 2004/0146516 A1 | 7/2004 | Roben et al. |
| 2004/0213791 A1 | 10/2004 | Bander et al. |
| 2004/0229845 A1 | 11/2004 | Frangioni |
| 2004/0242582 A1 | 12/2004 | Green et al. |
| 2005/0002942 A1 | 1/2005 | Vlahov et al. |
| 2005/0107325 A1 | 5/2005 | Manoharan et al. |
| 2005/0119166 A1 | 6/2005 | Brady et al. |
| 2005/0158780 A1 | 7/2005 | Lupold et al. |
| 2005/0234247 A1 | 10/2005 | Klar et al. |
| 2005/0239138 A1 | 10/2005 | Hess et al. |
| 2005/0239739 A1 | 10/2005 | Matulic-Adamic |
| 2005/0245486 A1 | 11/2005 | Frangioni |
| 2006/0024317 A1 | 2/2006 | Boyd et al. |
| 2006/0052312 A1 | 3/2006 | Erhardt et al. |
| 2006/0062793 A1 | 3/2006 | Webb et al. |
| 2006/0105975 A1 | 5/2006 | Pendergrast et al. |
| 2006/0106047 A1 | 5/2006 | Jiang et al. |
| 2006/0140871 A1 | 6/2006 | Sillerud |
| 2006/0148718 A1 | 7/2006 | Brady et al. |
| 2006/0155021 A1 | 7/2006 | Lenges et al. |
| 2006/0155146 A1 | 7/2006 | Lenges et al. |
| 2007/0010014 A1 | 1/2007 | Wood et al. |
| 2007/0020327 A1 | 1/2007 | Fikes et al. |
| 2007/0031326 A1 | 2/2007 | Shirvan et al. |
| 2007/0031438 A1 | 2/2007 | Junghans |
| 2007/0041901 A1 | 2/2007 | Diener et al. |
| 2007/0117153 A1 | 5/2007 | Bieniarz et al. |
| 2007/0128670 A1 | 6/2007 | Klatzmann et al. |
| 2007/0134332 A1 | 6/2007 | Turnell et al. |
| 2007/0142296 A1 | 6/2007 | McBride et al. |
| 2007/0148662 A1 | 6/2007 | Israeli et al. |
| 2007/0160617 A1 | 7/2007 | Ma et al. |
| 2007/0172422 A1 | 7/2007 | Glazier |
| 2007/0179100 A1 | 8/2007 | Manoharan |
| 2007/0219165 A1 | 9/2007 | Berkman et al. |
| 2007/0225213 A1 | 9/2007 | Kosak |
| 2007/0244055 A1 | 10/2007 | Brady et al. |
| 2007/0254316 A1 | 11/2007 | Rodriguez et al. |
| 2007/0254317 A1 | 11/2007 | Busseret-Michel et al. |
| 2008/0008719 A1 | 1/2008 | Bowdish et al. |
| 2008/0089869 A1 | 4/2008 | Denmeade et al. |
| 2008/0114153 A1 | 5/2008 | Steeves et al. |
| 2008/0175789 A1 | 7/2008 | Frangioni |
| 2008/0176821 A1 | 7/2008 | Kozikowski et al. |
| 2008/0193381 A1 | 8/2008 | Babich et al. |
| 2008/0214436 A1 | 9/2008 | Yu et al. |
| 2008/0248052 A1 | 10/2008 | Vlahov et al. |
| 2008/0269105 A1 | 10/2008 | Taft et al. |
| 2008/0311037 A1 | 12/2008 | Heston et al. |
| 2009/0117042 A1 | 5/2009 | Pomper et al. |
| 2009/0123467 A1 | 5/2009 | Bedi et al. |
| 2009/0180951 A1 | 7/2009 | Zimmerman et al. |
| 2009/0247614 A1 | 10/2009 | Manoharan et al. |
| 2009/0258002 A1 | 10/2009 | Barrett et al. |
| 2009/0274625 A1 | 11/2009 | Denmeade et al. |
| 2010/0048490 A1 | 2/2010 | Vlahov et al. |
| 2010/0092496 A1 | 4/2010 | Boyd et al. |
| 2010/0178246 A1 | 7/2010 | Babich et al. |
| 2010/0183509 A1 | 7/2010 | Babich et al. |
| 2010/0183517 A1 | 7/2010 | Berkman |
| 2010/0209343 A1 | 8/2010 | Bander et al. |
| 2010/0240701 A1 | 9/2010 | Vlahov et al. |
| 2011/0008253 A1 | 1/2011 | Babich et al. |
| 2011/0027180 A1 | 2/2011 | Magnani |
| 2011/0027274 A1 | 2/2011 | Cheng et al. |

(56) References Cited

U.S. PATENT DOCUMENTS

| | | |
|---|---|---|
| 2011/0064657 A1 | 3/2011 | Pomper et al. |
| 2011/0142760 A1 | 6/2011 | Pomper et al. |
| 2011/0176998 A1 | 7/2011 | Pomper et al. |
| 2011/0200677 A1 | 8/2011 | Chandran et al. |
| 2011/0288152 A1 | 11/2011 | Low et al. |
| 2012/0009121 A1 | 1/2012 | Pomper et al. |
| 2012/0276162 A1 | 11/2012 | Zale et al. |
| 2014/0107316 A1 | 4/2014 | Vlahov et al. |
| 2014/0140925 A1 | 5/2014 | Leamon et al. |

FOREIGN PATENT DOCUMENTS

| | | |
|---|---|---|
| JP | 2002-506204 | 2/2002 |
| JP | 2004-536034 | 12/2004 |
| JP | 2005-274569 | 10/2005 |
| JP | 2006-501149 | 1/2006 |
| JP | 2006-518712 | 8/2006 |
| JP | 2007-521803 | 8/2007 |
| WO | WO 88/01622 | 3/1988 |
| WO | WO 91/07418 | 4/1991 |
| WO | WO 99/45374 | 9/1999 |
| WO | WO 02/43773 | 6/2002 |
| WO | WO 02/062398 | 8/2002 |
| WO | WO 02/098885 | 12/2002 |
| WO | WO 03/060523 | 7/2003 |
| WO | WO 03/092742 | 11/2003 |
| WO | WO 03/097647 | 11/2003 |
| WO | WO 2004/010957 | 2/2004 |
| WO | WO 2004/069159 | 8/2004 |
| WO | WO 2005/082023 | 9/2005 |
| WO | WO 2006/012527 | 2/2006 |
| WO | WO 2006/093991 | 9/2006 |
| WO | WO 2006/096754 | 9/2006 |
| WO | WO 2007/022494 | 2/2007 |
| WO | WO 2007/106869 | 9/2007 |
| WO | WO 2008/057437 | 5/2008 |
| WO | WO 2008/058192 | 5/2008 |
| WO | WO 2008/121949 | 10/2008 |
| WO | WO 2009/026177 | 2/2009 |
| WO | WO 2009/082606 | 2/2009 |
| WO | WO 2009/002993 | 12/2009 |
| WO | WO 2010/014933 | 2/2010 |
| WO | WO 2010/065902 | 6/2010 |
| WO | WO 2011/106639 | 9/2011 |
| WO | WO 2014/078484 | 5/2014 |
| WO | WO 2014/134543 | 9/2014 |

OTHER PUBLICATIONS

Silverman, "The Organic Chemistry of Drug Design and Drug Action," Elsevier Academic Press (2nd Ed. 2003) (Book).

Wang et al., "Prostate-Specific Membrane Antigen Targeted Tubulysin Conjugates for Cancer Therapy," *246th ACS National Meeting and Exposition* (Sep. 8, 2013) Poster.

Banerjee, S. et al., "Sequential SPECT and Optical Imaging of Experimental Models of Prostate Cancer with a Dual Modality Inhibitor of the Prostate-Specific Membrane Antigen," Angewandte Chemie International Edition, 2011, 50, 9167-9170.

Bennet, V.J., "Analysis of fluorescently labeled substance P analogs: binding, imaging and receptor activation," BMC Chemical Biology, 2001, 1:1. doi:10.1186/1472-6769-1-1.

Kaur, G. et al., "Biological evaluation of tubulysin A: a potential anticancer and antiangiogenic natural product," Biochem. J., 2006, 396, 235-242.

Lu, G. et al., "Synthesis and SAR of 99mTc/Re-labeled small molecule prostate specific membrane antigen inhibitors with novel polar chelates," Bioorganic and Medicinal Chemistry Letters, 2013, 23, 1557-1563.

Banerjee, S.R. et al. "Synthesis and Evaluation of Technetium-99m- and Rhenium-Labeled Inhibitors of the Prostate-Specific Membrane Antigen (PSMA)," J Med Chem. Aug. 14, 2008; 51(15): 4504-4517.

Chen, Ying, et al., "Radiohalogenated Prostate-Specific Membrane Antigen (PSMA)-Based Ureas as Imaging Agents for Prostate Cancer," J. Med. Chem., 2008, 51 (24), pp. 7933-7943.

Davis, Mindy I., et al., "Crystal Structure of Prostate-Specific Membrane Antigen, A Tumor Marker and Peptidase", Apr. 26, 2005, PNAS, vol. 102, No. 17, pp. 5981-5986.

Definition of ligand, Random House Kernerman Webster's College Dictionary, downloaded on Jan. 25, 2014 from http://www.thefreedictionary.com/ligand, 1 page.

Eder et al., 68Ga-complex lipophilicity and the targeting property of a urea-based PSMA inhibitor for PET imaging, Bioconjugate Chemistry, 2012; 23:688-697.

Farokhzad, et al., "Nanoparticle-Aptamer Bioconjugates: A New Approach for Targeting Prostate Cancer Cells," Cancer Research 64, pp. 7668-7672 (2004).

Foss, Catherine A., et al. "Radiolabeled small-molecule ligands for prostate-specific membrane antigen: in vivo imaging in experimental models of prostate cancer." Clinical cancer research 11.11 (2005): 4022-4028.

Gomez-Hens et al., "Long wavelength fluorophores: new trends in their analytical use," Trends in Analytical Chemistry, 2004; 23:127-136.

Henne, et al., "Synthesis and activity of a folate peptide camptothecin prodrug," ScienceDirect, Bioorganic & Medical Chemistry Letters 16 (2006) 5350-5355.

Hillier, Shawn M., et al., "Preclinical Evaluation of Novel Glutamate-Urea-Lysine Analogues That Target Prostate-Specific Membrane Antigen as Molecular Imaging Pharmaceuticals for Prostate Cancer," Cancer Res. Sep. 1, 2009;69(17):6932-40.

Jackson, Paul F., et al., "Design of NAALADase Inhibitors: A Novel Neuroprotective Strategy", 2001, Current Medicinal Chemistry, vol. 8, No. 8, pp. 949-957.

Jayaprakash, Sarva, et al. "Design and synthesis of a PSMA inhibitor—doxorubicin conjugate for targeted prostate cancer therapy." ChemMedChem 1.3 (2006): 299-302.

Kozikowski, Alan P., et al., Design of Remarkably Simple, Yet Potent Urea-Based Inhibitors of Glutamate Carbozypeptidase II (NAALADase) 2001, Journal of Medicinal Chemistry, vol., 44, No. 3, pp. 298-301.

Kozikowski, Alan P., et al., "Synthesis of Urea-Based Inhibitors as Active Site Probes of Glutamate Carboxypeptodase II: Efficacy as Analgesic Agents", 2004, Journal of Medicinal Chemistry, vol., 47, No. 7, pp. 1729-1738.

Kularatne, S., "Synthesis and Biological Analysis of Prostate-Specific Membrane Antigen-Targeted Anticancer Prodrugs," J. Med. Chem, 2010, 53(21), 7767-7777.

Larock, "Comprehensive Organic Transformations, a guide to functional group preparations," VCH Publishers, Inc. New York (1989).

Lupold, et al., "Identification and characterization of nuclease-stabilized RNA molecules that bind human prostate cancer cells via the prostate-specific membrane antigen." Cancer Res. 2002; 62:4029-4033.

Majer, Pavel., et al., "Synthesis and Biological Evaluation of Thiol-Based Inhibitors of Glutamate Carboxypeptodase II: Discovery of an Orally Active GCP II Inhibitor", 2003, Journal of Medicinal Chemistry, vol. 46, No. 10, pp. 1989-1996.

Maresca, K. P., "A Series of Halogenated Heterodimeric Inhibitors of Prostate Specific Membrane Antigen (PSMA) as Radiolabeled Probes for Targeting Prostate Cancer," J. Med. Chem., 2009, 52 (2), pp. 347-357.

Maresca, K., et al., "Molecular targeting of prostate cancer with small molecule inhibitors of prostate specific membrane antigen (PSMA)," J. Nucl. Med. 2007, 48 (Supplement 2):25P.

Martin, et al., Helv. Chim. Acta, 78, 486-504 (1995) and Abstract, Abstract only.

McNamara et al, Cell type specific delivery of siRNAs with aptamer-siRNA chimeras, Nature Biotechnolgy, 2006; 24: 1005-1015.

Melby, et at., Cancer Research 53(8), pp. 1755-1760 (1993).

Mesters, et al., et al., "Structure of Glutamate Carboxypeptidase II, a Drug Target in Neuronal Damage and Prostate Cancer" 2006, The EMBO Journal, vol. 25, No. 6, pp. 1375-1384.

Olsnes, S., et al., Immunology Today, 10, pp. 291-295 (1989).

Paranjpe, et al., "Tumor-targeted bioconjugate based delivery of camptothecin: design, synthesis and in vitro evaluation," ScienceDirect Journal of Controlled Release 100 (2004) 275-292.

(56) References Cited

OTHER PUBLICATIONS

Pathalk et al., Enzymic protecting group techniques in organic synthesis, Stereosel. Biocatal. 775-797 (2000).

PCT International Search Report and Written Opinion for PCT/US2011/026238, mailed Apr. 27, 2011.

PCT International Search Report and Written Opinion for PCT/US2013/070007, mailed Mar. 5, 2014.

PCT International Search Report for PCT/US2008/073375 dated Oct. 26, 2008.

PCT International Search Report/Written Opinion for PCT/US2009/061067, completed May 28, 2010.

PCT International Search Report/Written Opinion for PCT/US2009/061049, completed Mar. 15, 2010.

Peltier et al., "The Total Synthesis of Tubulysin D," J. Am. Chem. Soc. 128:16018-19 (2006).

Pubchem, Compound summary for: CID 58099954, Aug. 19, 2012.

Ranasinghe, M. G., et al., "Facile Synthesis of Unsymmetrical Thiolsulfonates via Sulfonylation of Mercaptans", 1988, Synthetic Communications, vol. 18, No. 3, pp. 227-232.

Roy, et al., "Dupa Conjugation of a Cytotoxic Indenoisoquinoline Topoisomerase I Inhibitor for Selective Prostate Cancer Cell Targeting," J. Med. Chem. 58 (2015) 3094-3103.

Silverman, "The Organic Chemistry of Drug Design and Drug Action," Elsevier Academic Press (2nd Ed. 2003). (Book).

Theodora E. Greene & Peter G.M. Wuts, "Protective Groups ion Organic Synthesis," 2d edition, John Wiley & Sons, Inc. New York (1991).

Truffert, et al., Tetrahedron, 52:3005 (1996).

Vlahov, et al., "Design and regioselective synthesis of a new generation of targeted chemotherapeutics. Part 1: EC145, a folic acid conjugate of desacetylvinblastine monohydrazide," ScienceDirect, Bioorganic & Medical Chemistry Letters 16 (2006) 5093-5096.

Yang, et al., "Characterization of the pH of Folate Receptor-Containing Endosomes and the Rate of Hydrolysis of Internalized Acid-Labile Folate-Drug Conjugates," JPET 321: 462-468, 2007.

Cole et al., " Cancer Theranostics: The Rise of Targeted Magnetic Nanoparticles," *Trends Biotechnol.*, 29(7): 323-332 (2011).

CONJUGATES FOR TREATING DISEASES CAUSED BY PSMA EXPRESSING CELLS

CROSS REFERENCE TO RELATED APPLICATIONS

This application is a divisional of U.S. application Ser. No. 14/443,212, filed May 15, 2015, now U.S. Pat. No. 9,636,413, which is a U.S. national stage application under 35 U.S.C. §371(b) of International Application No. PCT/US2013/070007, filed Nov. 14, 2013, which in turn claims priority under 35 U.S.C. §119(e) to U.S. Provisional Application Ser. No. 61/726,991, filed Nov. 15, 2012, U.S. Provisional Application Ser. No. 61/788,382, filed Mar. 15, 2013, and U.S. Provisional Application Ser. No. 61/875,971, filed Sep. 10, 2013, all of which are incorporated herein by reference in their entirety.

TECHNICAL FIELD

The invention described herein pertains to the diagnosis, imaging, and/or treatment of pathogenic cell populations. In particular, the invention described herein pertains to the diagnosis, imaging, and/or treatment of diseases caused by PSMA expressing cells, such as prostate cancer cells, using compounds capable of targeting PSMA expressing cells.

BACKGROUND AND SUMMARY OF THE INVENTION

The prostate is a male reproductive organ and functions to produce and store seminal fluid that provides nutrients and fluids for the survival of sperm introduced into the vagina during reproduction. Like other tissues, the prostate gland may develop either malignant (cancerous) or benign (non-cancerous) tumors. In fact, prostate cancer is one of the most common male cancers in western societies, and is the second leading form of malignancy among American men. Current treatment methods for prostate cancer include hormonal therapy, radiation therapy, surgery, chemotherapy, photodynamic therapy, and combination therapy. However, many of these treatments affect the quality of life of the patient, especially for those men who are diagnosed with prostate cancer over age 50. For example, the use of hormonal drugs is often accompanied by side effects such as osteoporosis and liver damage. Such side effects might be mitigated by the use of treatments that are more selective or specific to the tissue being responsible for the disease state, and avoid non-target tissues like the bones or the liver.

Prostate-specific membrane antigen (PSMA) is a biomarker that is overexpressed on prostate cancer. PSMA is over-expressed in the malignant prostate tissues when compared to other organs in the human body such as kidney, proximal small intestine, and salivary glands. PSMA is also expressed on the neovasculature within many non-prostate solid tumors, including lung, colon, breast, renal, liver and pancreatic carcinomas, but not on normal vasculature. PSMA is also expressed minimally in brain. PSMA is a type II cell surface membrane-bound glycoprotein with ~110 kD molecular weight, including an intracellular segment (amino acids 1-18), a transmembrane domain (amino acids 19-43), and an extensive extracellular domain (amino acids 44-750). While the functions of the intracellular segment and the transmembrane domains are currently believed to be insignificant, the extracellular domain is involved in several distinct activities. For example, PSMA plays a role in the central nervous system, where it metabolizes N-acetyl aspartyl glutamate (NAAG) into glutamic and N-acetyl aspartic acid. PSMA also plays a role in the proximal small intestine where it removes γ-linked glutamate from poly-γ-glutamated folate and α-linked glutamate from peptides and small molecules. However, PSMA's particular function on prostate cancer cells remains unresolved.

Unlike many other membrane-bound proteins, PSMA undergoes rapid internalization into the cell in a similar fashion to cell surface bound receptors like vitamin receptors. PSMA is internalized through clathrin-coated pits and subsequently can either recycle to the cell surface or go to lysosomes. Accordingly, diagnostic, imaging, and therapeutic agents can be targeted to PSMA for delivery into PSMA expressing cells, such as prostate cancer cells.

Described herein are compounds capable of binding to PSMA. Also described herein are compounds capable of targeting PSMA for delivery of diagnostic, imaging, and therapeutic agents. Also described herein are compounds and compositions, and methods and uses thereof for diagnosing, imaging, and treating diseases caused by pathogenic populations of cells that express, or overexpress, PSMA.

It has been unexpectedly discovered that the conjugates described herein exhibit high affinity for PSMA. It has also been discovered that the compounds described herein are efficacious in treating diseases caused by pathogenic cells that express PSMA, such a prostate cancer cells.

In one illustrative embodiment of the invention, PSMA binding drug delivery conjugates of the formula $$B\text{-}L\text{-}(D)_n$$

or pharmaceutically acceptable salts thereof are described herein, where B comprises a urea or thiourea of lysine and an amino acid, or one or more carboxylic acid derivatives thereof, where the urea or thiourea is capable of binding to PSMA, L is a polyvalent linker, D is a radical of a drug, and n is an integer selected from 1, 2, 3, and 4. It is to be understood that as used herein, such drugs, and the term drug, includes therapeutic agents, diagnostic agents, imaging agents, and other compounds that are desirably delivered to or targeted to PSMA and/or PSMA expressing cells.

In another illustrative embodiment, PSMA binding drug delivery conjugates of the formula $$B\text{-}L\text{-}(D)_n$$

or pharmaceutically acceptable salts thereof are described herein, where B is a radical of a PSMA binding or targeting ligand, L is a polyvalent linker comprising an aminomethylphenylacetic acid diradical, or an aminophenylacetic acid diradical, or both, D is a radical of a drug, and n is an integer selected from 1, 2, 3, and 4.

It is to be understood that every combination of the various embodiments ea of B, L, D, and n described herein form illustrative embodiments of the conjugates of the invention, whether those various embodiments of each of B, L, D are species, subgenera, or genera. It is to be further understood that each of those additional illustrative embodiments of compounds may be used in any of the compositions, unit doses, methods, and/or uses described herein.

In another embodiment, pharmaceutical compositions containing one or more of the compounds are also described herein. In one aspect, the compositions are in bulk form and are suitable for preparing unit doses, unit dosage forms, and the like that may be included in the uses and/or methods described herein. In another aspect, the compositions include a therapeutically effective amount of the one or more compounds for diagnosis, imaging, and/or treatment of diseases caused by PSMA expressing cells in a patient.

Illustrative compositions include unit doses, unit dosage forms, and the like. It is to be understood that the compositions may include other components and/or ingredients, including, but not limited to, other therapeutically active compounds, and/or one or more carriers, and/or one or more diluents, and/or one or more excipients, and the like. In another embodiment, methods fix using the compounds and pharmaceutical compositions for diagnosis, imaging, and/or treatment of diseases caused by PSMA expressing cells in a patient are also described herein. In one aspect, the methods include the step of administering one or more of the compounds and/or compositions described herein to the patient. In another embodiment, uses of the compounds and compositions in the manufacture of a medicament for diagnosis, imaging, and/or treatment of diseases caused by PSMA expressing cells in a patient are also described herein. In one aspect, the medicaments include a therapeutically effective amount of the one or more compounds and/or compositions described herein.

It is appreciated herein that the compounds described herein may be used alone or in combination with other compounds useful for diagnosis, imaging, and/or treatment of diseases caused by PSMA expressing cells in a patient, including those compounds that may be therapeutically effective by the same or different modes of action. In addition, it is appreciated herein that the compounds described herein may be used in combination with other compounds that are administered to treat other symptoms of the disease, such as compounds administered to decrease pain, and the like.

DETAILED DESCRIPTION

Figure 1:
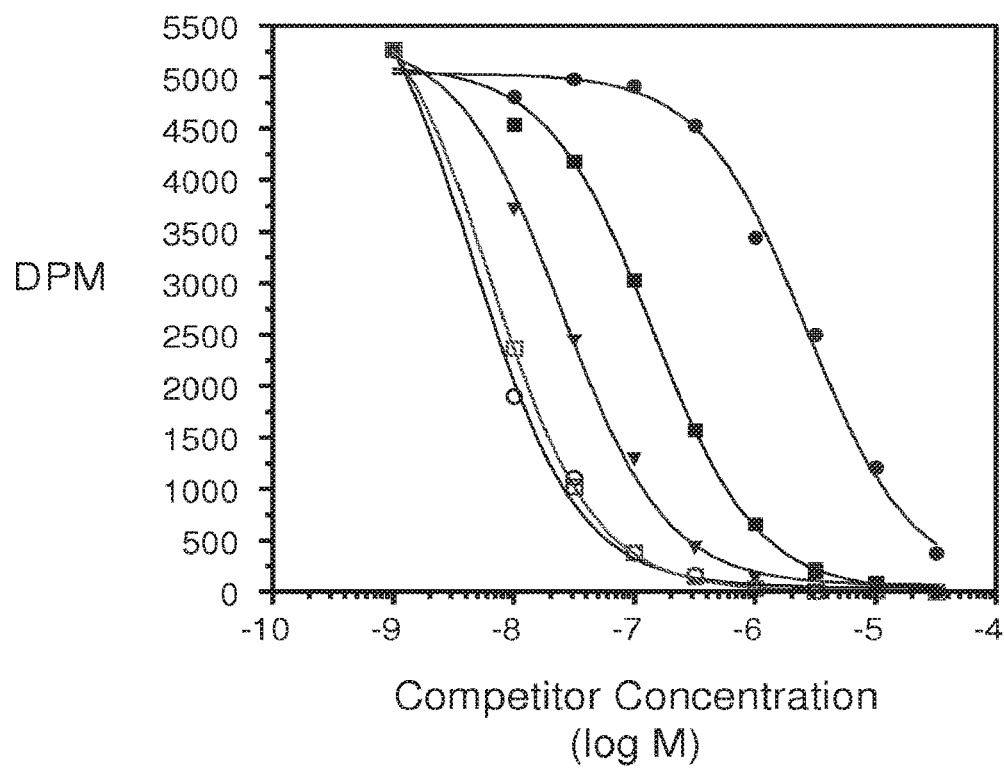
FIG. 1 shows the relative affinity of (■) PMPA, 1.0 (normalized); (●) DUPA, 0.05 (19-fold lower); (○) EC1067, 30×; (□) EC1069, 22×; and (▼) EC1080, 6× in 10% serum/FDRPMI for PSMA.

Several illustrative embodiments of the invention are described by the following enumerated clauses:

1. A conjugate of the formula

or a pharmaceutically acceptable salt thereof, wherein B comprises a urea or thiourea of lysine and an amino acid, or one or more carboxylic acid derivatives thereof, including, but not limited to, ureas or thioureas of lysine and aspartic acid, or glutamic acid, or homoglutamic acid, where the urea or thiourea is capable of binding to PSMA, L is a polyvalent linker, D is a radical of a drug, and n is an integer selected from 1, 2, 3, and 4.

2. A conjugate of the formula

or a pharmaceutically acceptable salt thereof, wherein B is a radical of the formula

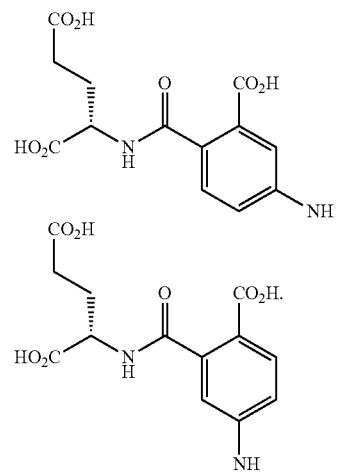

L is a polyvalent linker, D is a radical of a drug, and n is an integer selected from 2, 3, and 4.

3. The conjugate of clause 1 or 2 wherein L is a polyvalent linker comprising an aminomethylphenylacetic acid diradical, or an aminophenylacetic acid diradical, or both.

4. A conjugate of the formula

or a pharmaceutically acceptable salt thereof, wherein B is a radical of a PSMA binding ligand, L is a polyvalent linker comprising an aminomethylphenylacetic acid diradical or an aminophenylacetic acid diradical or both, D is a radical of a drug, and n is an integer selected from 1, 2, 3, and 4.

5. The conjugate of clause 3 wherein B comprises a urea or thiourea of lysine and an amino acid, or one or more carboxylic acid derivatives thereof, including, but not limited to ureas or thioureas of lysine and aspartic acid, or glutamic acid, or homoglutamic acid.

6. The conjugate of any one of clauses 1 to 5 wherein B comprises a urea or thiourea of lysine and glutamate, or one or more carboxylic acid derivatives thereof.

7. The conjugate of any one of clauses 1 to 5 wherein B comprises a urea of lysine and glutamate.

8. The conjugate of any one of clauses 1 to 5 wherein B comprises a urea or thiourea of L-lysine and glutamate, or one or more carboxylic acid derivatives thereof.

9. The conjugate of any one of clauses 1 to 5 wherein B comprises a urea of L-lysine and L-glutamate.

10. The conjugate of any one of clauses 1 to 5 wherein B comprises a urea or thiourea of lysine and glutamic acid.

11. The conjugate of any one of clauses 1 to 5 wherein B comprises a urea or thiourea of D-lysine and D-glutamic acid.

12. The conjugate of any one of clauses 1 to 5 wherein B comprises a urea or thiourea of D-lysine and one or the following:

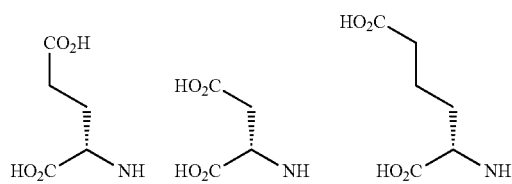

13. The conjugate of any one of clauses 1 to 5 wherein B comprises a urea or thiourea of D-lysine and:

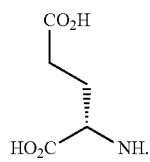

14. The conjugate of any one of clauses 1 to 5 wherein B is a urea.

15. The conjugate of any one of clauses 1 to 5 wherein B is selected from the following

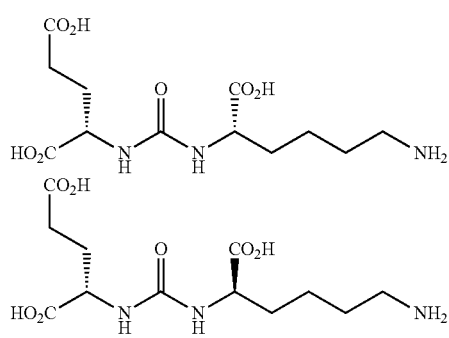

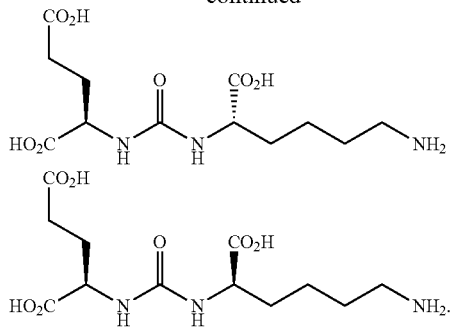

16. The conjugate of any one of clauses 1 to 5 wherein B is selected from the following

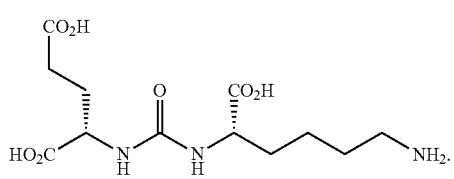 [SMILES: NCCCC[C@H](NC(=O)N[C@@H](CCC(=O)O)C(=O)O)C(=O)O]

17. The conjugate of any one of clauses 1 to 5 wherein B is of the formula

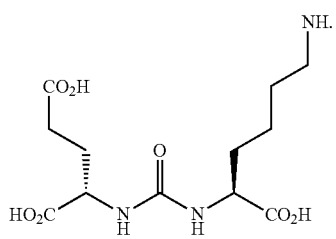

The conjugate of any one of the preceding clauses wherein n is 1, 2, or 3.

The conjugate of any one of the preceding clauses wherein n is 1 or 2.

The conjugate of any one of the preceding clauses wherein n is 1.

The conjugate of any one of the preceding clauses wherein at least one drug is an imaging agent.

The conjugate of any one of the preceding clauses wherein at least one drug is a diagnostic agent.

The conjugate of any one of the preceding clauses wherein at least one drug is a therapeutic agent.

The conjugate of any one of the preceding clauses wherein at least one drug is a cytotoxic agent.

The conjugate of any one of the preceding clauses wherein at least one drug is a tubulysin.

The conjugate of any one of the preceding clauses wherein at least one drug is a naturally occurring tubulysin.

The conjugate of any one of the preceding clauses wherein at least one drug is tubulysin B.

The conjugate of any one of the preceding clauses wherein at least one drug, is a tubulysin of the formula

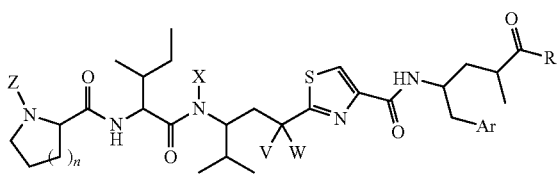

and pharmaceutical salts thereof are described, where
n is 1-3;

V is hydrogen, $OR^2$, or halo, and W is hydrogen, $OR^2$, or alkyl, where $R^2$ is independently selected in each instance from hydrogen, alkyl, and $C(O)R^3$, where $R^3$ is alkyl, cycloalkyl, alkenyl, aryl, or arylalkyl, each of which is optionally substituted; providing that $R^2$ is not H when both V and W are $OR^2$; or V and W are taken together with the attached carbon to form a carbonyl;

X is hydrogen, alkyl, such as $C_{1-6}$ alkyl, or $C_{2-6}$ alkyl, $C_{1-4}$ alkyl, or $C_{2-4}$ alkyl, or alkenyl, such as $C_{2-6}$ alkenyl or $C_{2-4}$ alkenyl, each of which is optionally substituted;

Z is alkyl or $C(O)R^4$, where $R^4$ is alkyl, $CF_3$, or aryl;

Ar is aryl or heteroaryl, each of which is optionally substituted; and

R is OH or R and the carbonyl to which it is attached is a carboxylic acid derivative.

The conjugate of any one of the preceding clauses wherein Ar is optionally substituted phenyl.

The conjugate of any one of the preceding clauses wherein Ar is phenyl substituted with one or more substituents selected from the group consisting of halo, hydroxy, amino, thio, carboxylate or a derivative thereof, sulfinyl or a derivative thereof, sulfonyl or a derivative thereof, phosphinyl or a derivative thereof, or phosphonyl or a derivative thereof, or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted.

The conjugate of any one of the preceding clauses wherein Ar is phenyl.

The conjugate of any one of the preceding clauses wherein Ar is 4-hydroxyphenyl.

The conjugate of any one of the preceding clauses wherein X is $CH_2QR^9$, where Q is —N—, —O—, or —S—; $R^9$ is hydrogen or alkyl, alkenyl, cycloalkyl, aryl, or arylalkyl, each of which is optionally substituted, or $C(O)R^{10}$.

The conjugate of any one of the preceding clauses wherein Q is O.

The conjugate of any one of the preceding clauses wherein $R^9$ is optionally substituted alkyl.

The conjugate of any one of the preceding clauses wherein $R^9$ is alkyl.

The conjugate of any one of the preceding clauses wherein $R^{10}$ is optionally substituted alkyl.

The conjugate of any one of the preceding clauses wherein $R^{10}$ is alkyl.

The conjugate of any one of the preceding clauses wherein at least one drug is selected from the following:

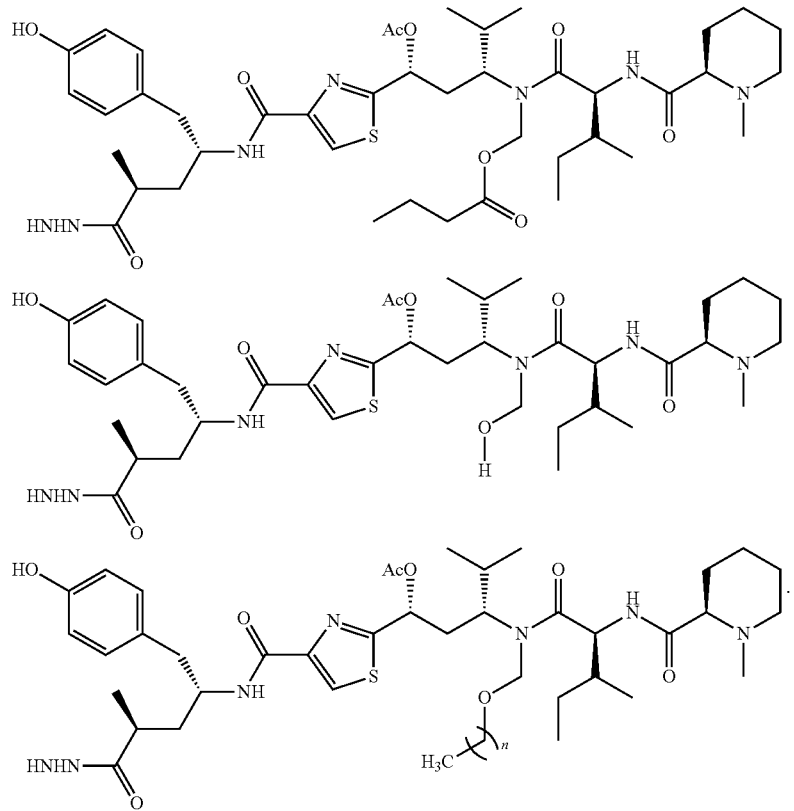

n = 0, 1, 2, 3, 4, 5, 6

The conjugate of any one of the preceding clauses wherein at least one drug is:

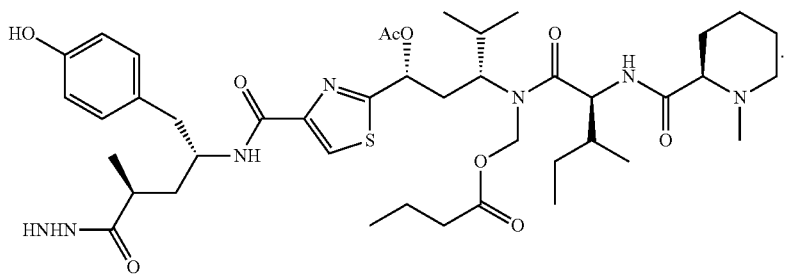

The conjugate of any one of the preceding clauses wherein at least one D is a radical of the formula

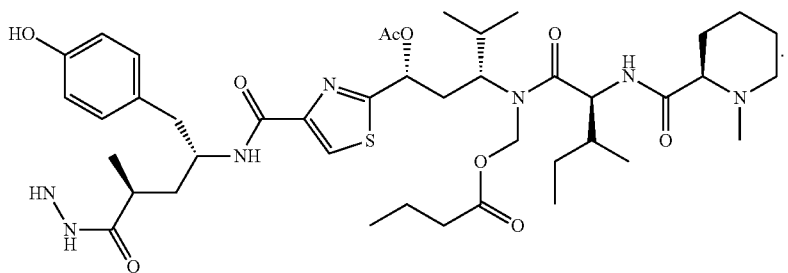

The conjugate of any one of the preceding clauses wherein at least one D is a radical of the formula

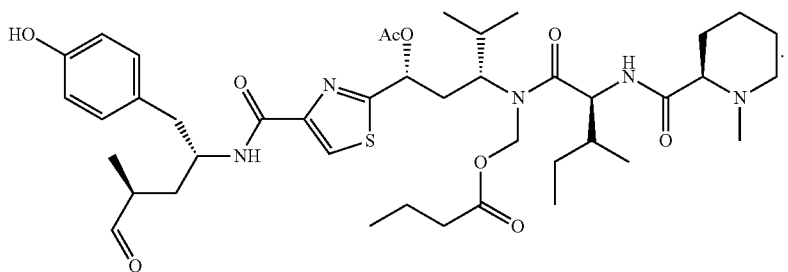

The conjugate of any one of the preceding clauses wherein at least one D is a radical of the formula

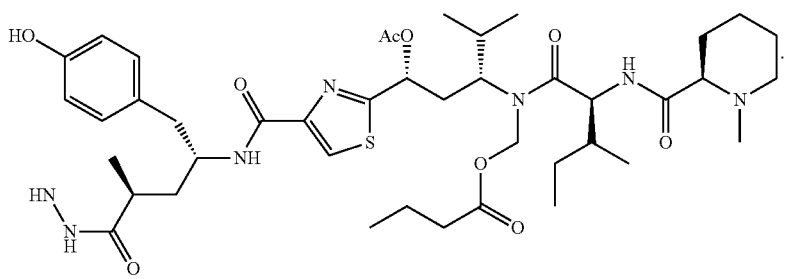

The conjugate of any one of the preceding clauses wherein at least one D is a radical of the formula

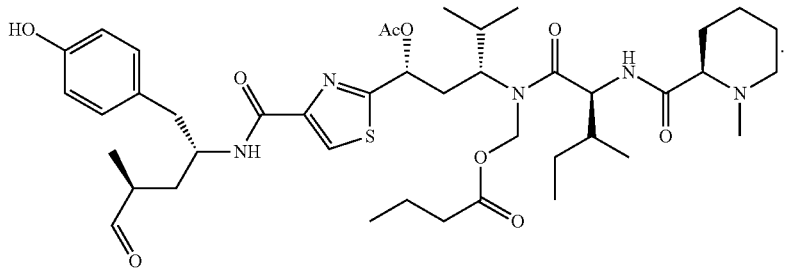

The conjugate of any one of the preceding clauses wherein at least one D is a radical of the formula

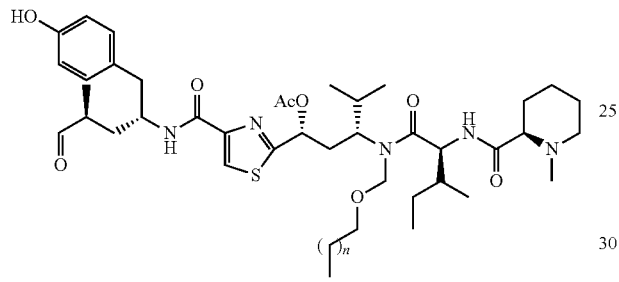

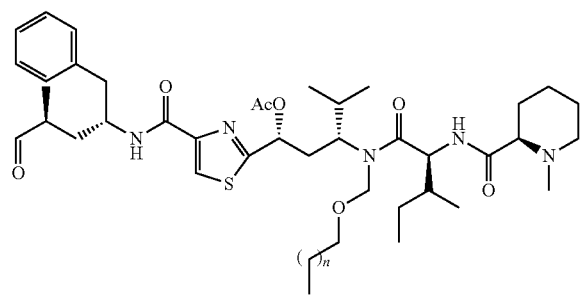

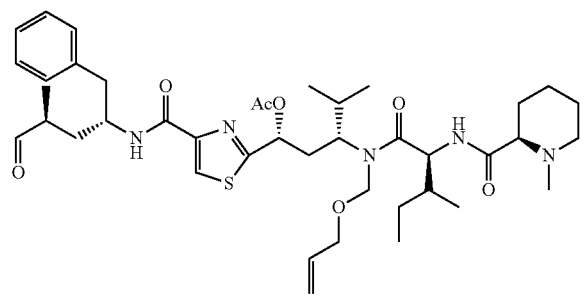

where n=1, 2, 3, 4, 5, or 6.

The conjugate of any one of the preceding clauses wherein L comprises an aminomethylphenylacetic acid diradical.

The conjugate of any one of the preceding clauses wherein L comprises an aminophenylacetic acid diradical The conjugate of any one of the preceding clauses wherein L forms a urea or thiourea with the lysine.

The conjugate of any one of the preceding clauses wherein L forms a urea with the lysine.

The conjugate of any one of the preceding clauses wherein L forms an amide or thioamide with the lysine.

The conjugate of any one of the preceding clauses wherein L forms an amide with the lysine.

The conjugate of any one of the preceding clauses wherein L comprises one or more aspartic acid diradicals.

The conjugate of any one of the preceding clauses wherein comprises two or more aspartic acid diradicals.

The conjugate of the preceding clauses wherein the aspartic acid diradicals are L-aspartic acid diradicals.

The conjugate of any one of the preceding clauses wherein L comprises a cysteine diradical.

The conjugate of any one of the preceding clauses wherein L comprises a L-cysteine diradical.

The conjugate of any one of the preceding clauses wherein L comprises L-Asp-L-Asp-L-Cys.

The conjugate of any one of the preceding clauses wherein L is a releasable linker, such as a releasable linker that is cleaved under conditions encountered at or near, or inside of pathogenic cells expressing, preferentially expressing, or overexpressing PSMA.

The conjugate of any one of the preceding clauses wherein L comprises a disulfide.

The conjugate of any one of the preceding clauses wherein L comprises a cysteine disulfide diradical.

The conjugate of any one of the preceding clauses wherein L comprises a L-cysteine disulfide diradical.

The conjugate of any one of the preceding clauses wherein L comprises L-Asp-L-Asp-L-Cys(S—S).

The conjugate of any one of the preceding clauses wherein L comprises a diradical of the formula O—C(O)—N.

The conjugate of any one of the preceding clauses wherein L comprises a diradical of the formula O—C(O)—NH.

The conjugate of any one of the preceding clauses wherein L and at least one D taken together comprise a diradical of the formula O—C(O)—N.

The conjugate of any one of the preceding clauses wherein L and at least one D taken together comprise a diradical of the formula O—C(O)—NH.

The conjugate of any one of the preceding clauses wherein L comprises a diradical of the formula S—(CH$_2$)$_m$—O, where m is 2, 3, or 4.

The conjugate of any one of the preceding clauses wherein L comprises a diradical of the formula S—(CH$_2$)$_m$—O—C(O)—N, where in is 2, 3, or 4.

The conjugate of any one of the preceding clauses wherein L comprises a diradical of the formula S—(CH$_2$)$_m$—O—C(O)—NH, where m is 2, 3, or 4.

The conjugate of any one of the preceding clauses wherein L and at least one D taken together comprise a diradical of the formula S—(CH$_2$)$_m$—O—C(O)—N, where m is 2, 3, or 4.

The conjugate of any one of the preceding clauses wherein L and at least one D taken together comprise a diradical of the formula S—(CH$_2$)$_m$—O—C(O)—NH, where m is 2, 3, or 4.

The conjugate of any one of the preceding clauses wherein the terminal sulfur atom forms a disulfide.

The conjugate of any one of the preceding clauses wherein m is 2.

The conjugate of any one of the preceding clauses wherein L comprises a chain of at least about 7 atoms, at least about 8 atoms, at least about 9 atoms, at least about 10 atoms, at least about 11 atoms, at least about 12 atoms, at least about 13 atoms, at least about 14 atoms, or at least about 15 atoms.

The conjugate of any one of the preceding clauses wherein L comprises a chain of at least about 16 atoms, at least about 17 atoms, at least about 18 atoms, at least about 19 atoms, at least about 20 atoms, at least about 21 atoms, at least about 22 atoms, at least about 23 atoms, at least about 24 atoms, at least about 25 atoms, or at least about 26 atoms.

The conjugate of any one of the preceding clauses wherein L comprises a chain of between about 7 and about 35 atoms, between about 7 and about 30 atoms, or between about 7 and about 26 atoms.

The conjugate of any one of the preceding clauses wherein L comprises a diradical of the formula

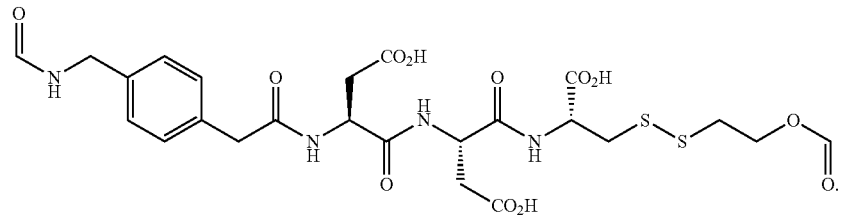

The conjugate of any one of the preceding clauses wherein L comprises a diradical of the formula

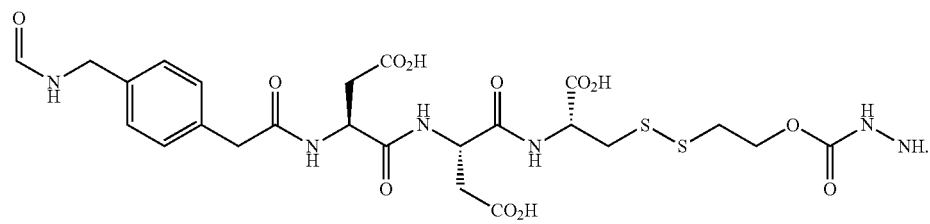

The conjugate of any one of the preceding clauses wherein L comprises a diradical of the formula

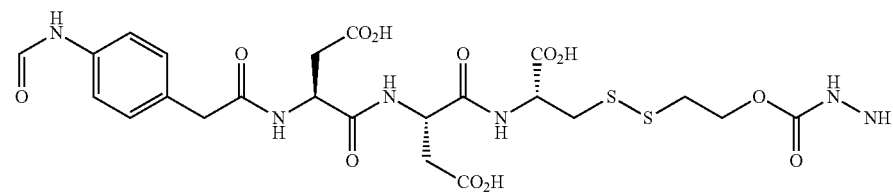

The conjugate of any one of the preceding clauses wherein L comprises a diradical of the formula

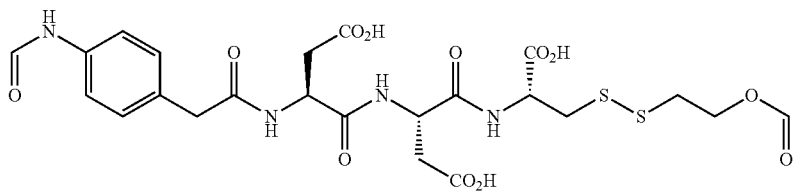

The conjugate of any one of the preceding clauses where L comprises a diradical of the formula

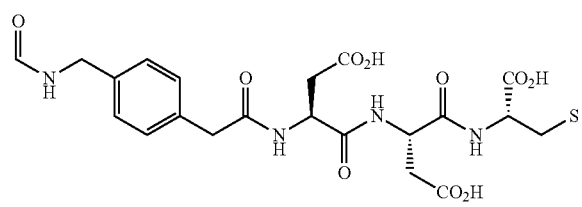

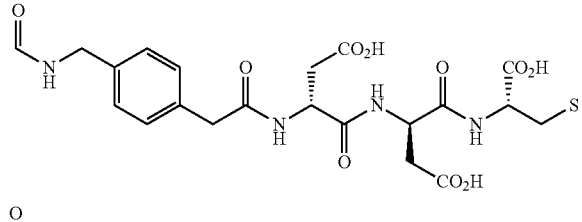

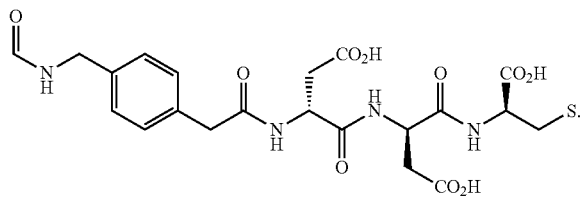

The conjugate of any one of the preceding clauses where L comprises a diradical of the formula

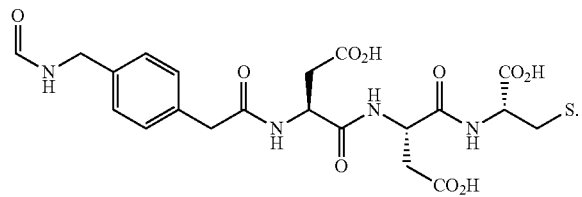

The conjugate of any one of the preceding clauses wherein L comprises a diradical of the formula

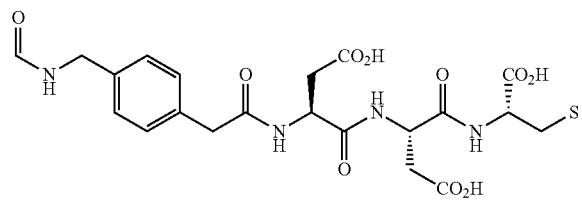

-continued

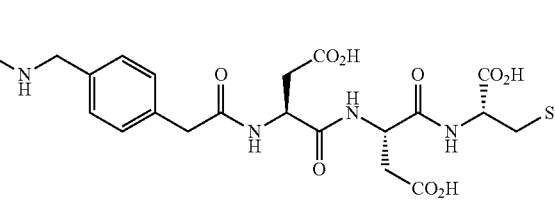

The conjugate of any one of the preceding clauses wherein L comprises a diradical of the formula The conjugate of any one of the preceding clauses wherein L comprises a diradical of the formula

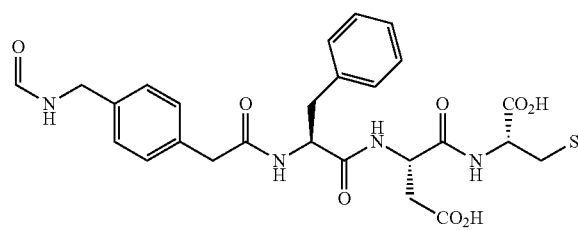
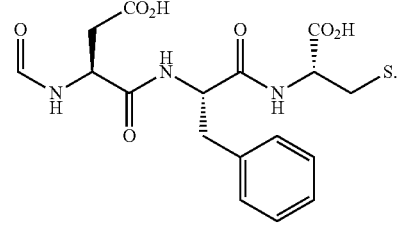
The conjugate of any one of the preceding clauses where comprises a diradical of the formula
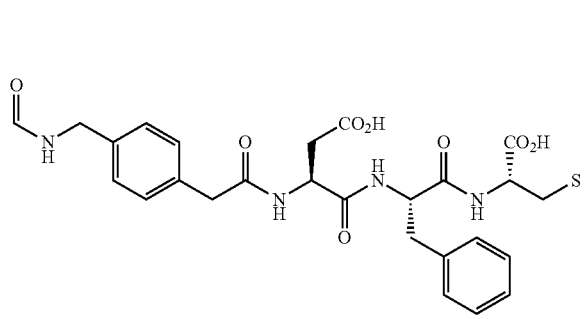
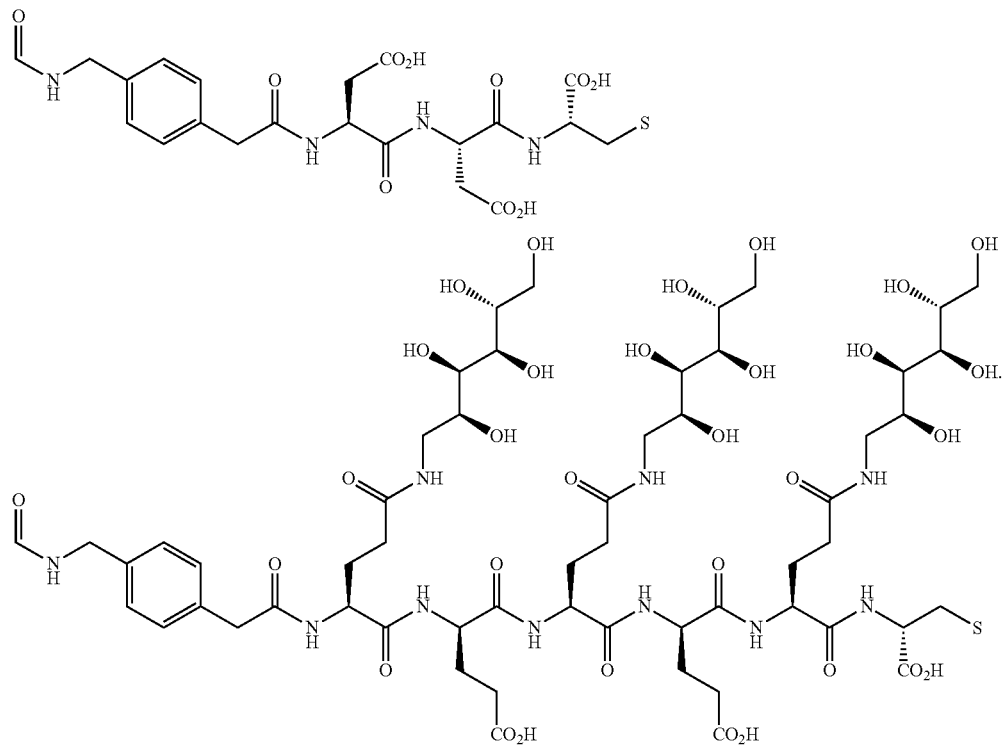
The conjugate of any one of the preceding clauses where L comprises a diradical of the formula The conjugate of any one of the preceding clauses where L comprises a diradical of the formula

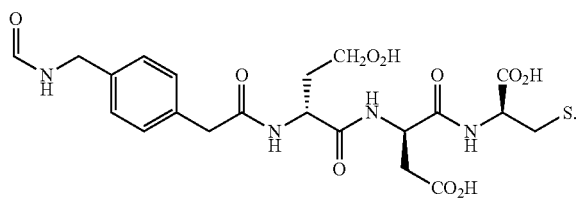

The conjugate of any one of the preceding clauses wherein L comprises a diradical of the formula

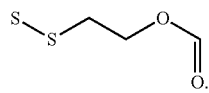

The conjugate of any one of the preceding clauses wherein L comprises a diradical of the formula

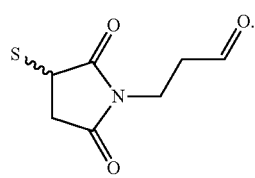

The conjugate of any one of the preceding clauses wherein B-L comprises a diradical of the formula

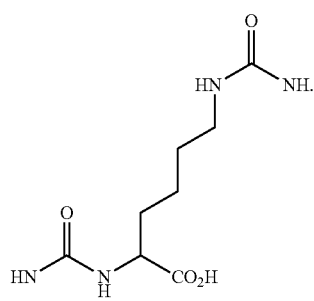

The conjugate of any one of the preceding clauses wherein B-L comprises a diradical of the formula

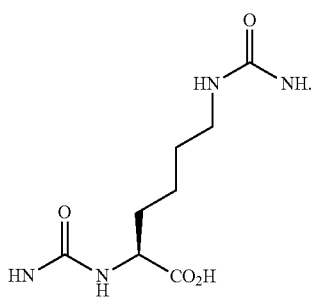

The conjugate of any one of the preceding clauses wherein B-L comprises a diradical of the formula

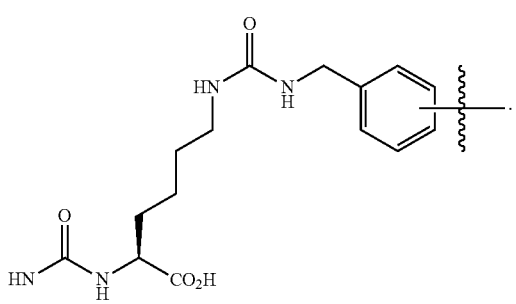

The conjugate of any one of the preceding clauses wherein B-L comprises a diradical of the formula

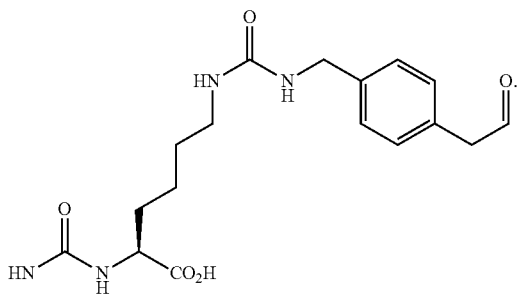

A conjugate of the formula

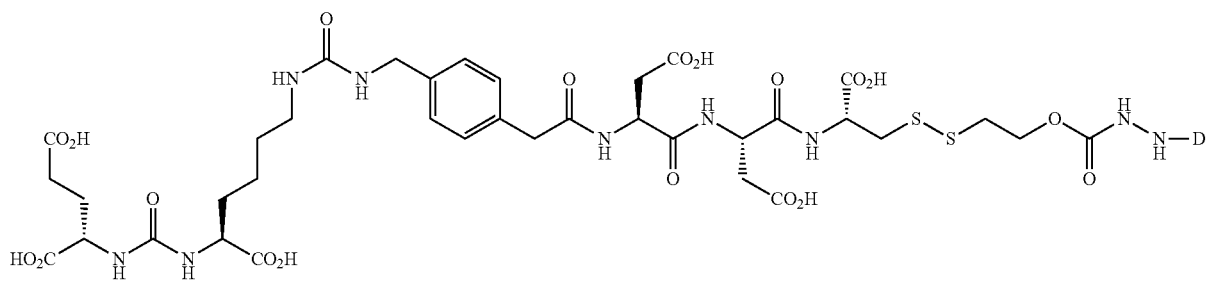

or a pharmaceutically acceptable salt thereof, and/or a hydrate, and/or a solvate, and/or a co-crystal of the foregoing; where D is radical of a drug.

A conjugate of the formula

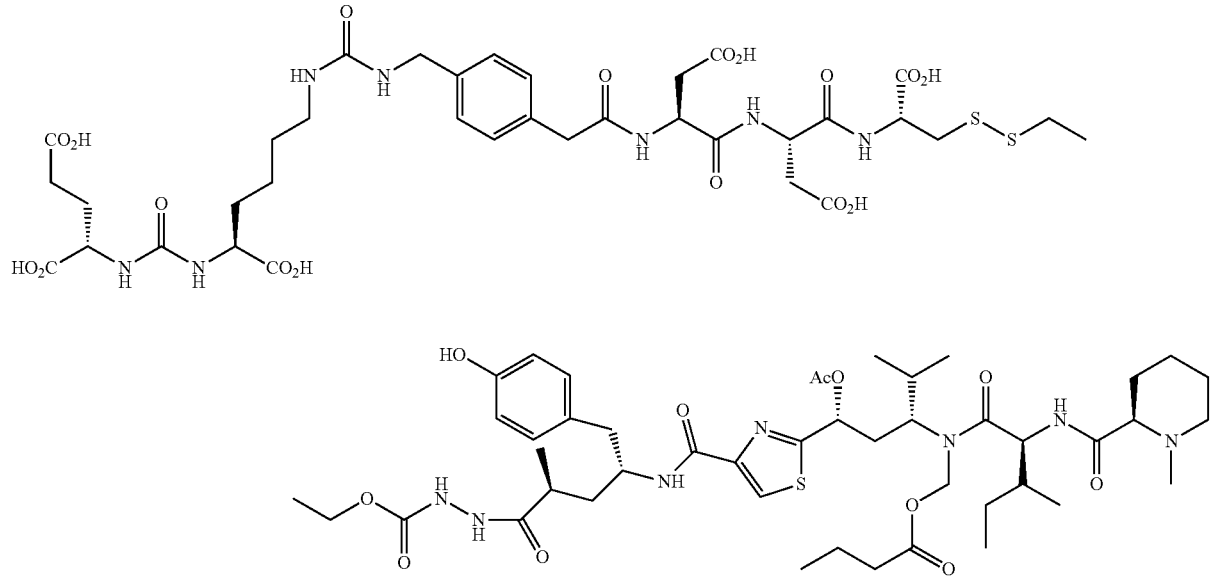

or a pharmaceutically acceptable salt thereof, and/or a hydrate, and/or a solvate, and/or a co-crystal of the foregoing; where D is radical of a drug.

A conjugate the formula

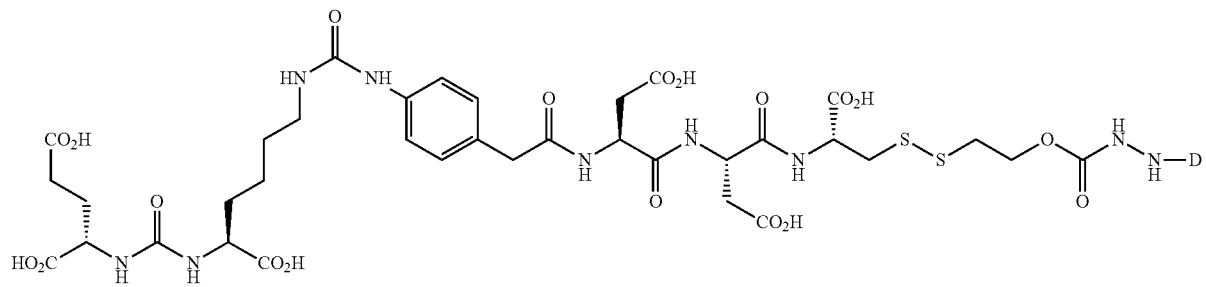

or a pharmaceutically acceptable salt thereof, and/or a hydrate, and/or a solvate, and/or a co-crystal of the foregoing; where D is radical of a drug.

A conjugate of the formula

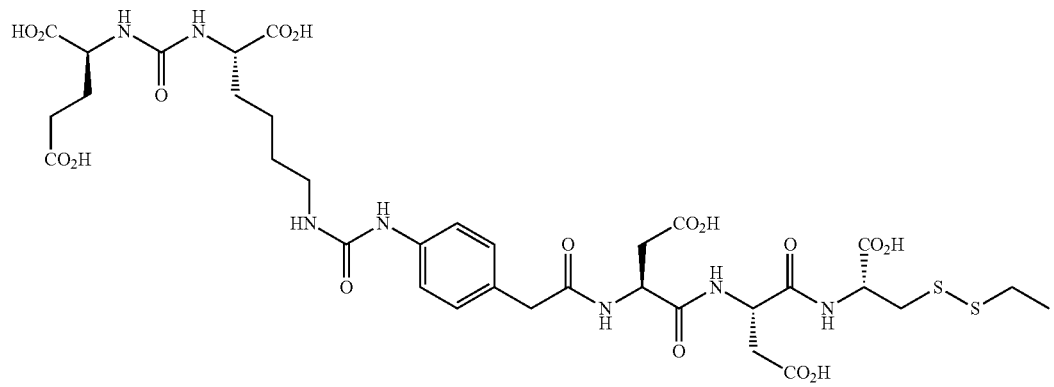

-continued

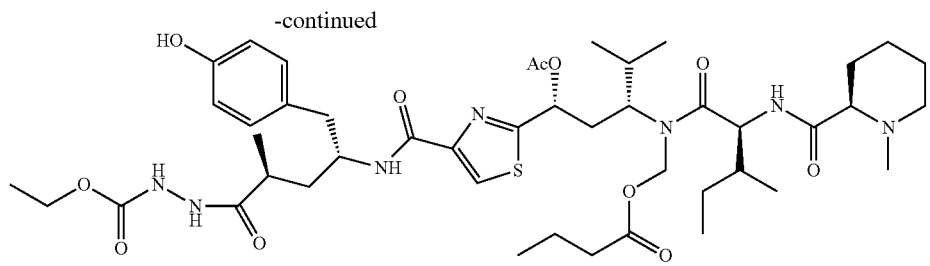

or a pharmaceutically acceptable salt thereof, and/or a hydrate, and/or a solvate, and/or a co-crystal of the foregoing; where D is radical of a drug.

A pharmaceutical composition comprising one or more of the compounds or conjugates of any one of the preceding clauses.

A pharmaceutical composition comprising one or more of the compounds or conjugates of any one of the preceding clauses for treating a disease in a host animal caused by a pathogenic population of cells, said cells expressing PSMA.

A unit dose or unit dosage form in single or divided form, the unit dose or unit dosage form comprising a therapeutically effective amount of one or more of the compounds or conjugates of any one of the preceding clauses for treating a disease in a host animal caused by a pathogenic population of cells, said cells expressing PSMA.

The composition or unit dose or unit dosage form of any one of the preceding clauses further comprising one or more carriers, diluents, or excipients, or a combination thereof.

A method for treating a disease in a host animal caused by a pathogenic population of cells, said cells expressing PSMA, the method comprising the step of administering to the patient a composition comprising a therapeutically effective amount of one or more of the compounds or conjugates or one or more of the compositions or unit doses or unit dosage forms of any one of clauses 1 to 73

Use of one or more of the compounds or conjugates, compositions, unit doses, or unit dosage forms of any one of the preceding clauses in the manufacture of a medicament for treating a disease in a host animal caused by a pathogenic population of cells, said cells expressing PSMA.

The composition, unit doses or unit dosage form, method, or use of any one of the preceding clauses wherein the cells are prostate cancer cells.

The composition, unit doses or unit dosage form, method, or use of any one of the preceding clauses wherein the disease is prostate cancer.

The composition, unit doses or unit dosage form, method, or use of any one of the preceding clauses wherein the host animal is a human.

In reciting the foregoing and following collection of embodiments and clauses, it is to be understood that all possible combinations of features, and all possible subgenera and sub-combinations are described. For example, it is to be understood that when B is limited to a binding ligand comprising urea of L-lysine and L-glutamate, L may be limited to a linker comprising one or more aspartic acid diradicals, or alternatively, to comprising a cysteine diradical, or alternatively, comprising L-Asp-L-Asp-L-Cys(S—S), and so forth. Similarly, when D is limited to a naturally occurring tubulysin L may be limited to a linker comprising diradical of the formula S—$(CH_2)_m$—O—C(O)—N, or alternatively, to comprising a cysteine disulfide diradical, or alternatively, comprising an aminophenylacetic acid diradical, and so forth. Similarly, when B is limited to a binding ligand comprising a urea or thiourea of lysine and glutamate, or one or more carboxylic acid derivatives thereof, L may be limited to a linker comprising one or more D-aspartic acid diradicals, and D may be limited to a tubulysin, or alternatively. L may be limited to a linker comprising a diradical of the formula O—C(O)—N, and D may be limited to an imaging agent, or alternatively, L may be limited to a linker comprising a diradical of the formula S—$(CH_2)_m$—O—C(O)—NH, and D may be limited to a therapeutic agent, and so forth. Other combinations, subgenera and sub-combinations are also described by the collection of clauses.

In another embodiment, at one drug is an imaging agent. Illustrative imaging agents for the conjugates described herein include, but are not limited to, radioisotopes, such as a radioactive isotope of a metal coordinated to a chelating group. Illustrative radioactive metal isotopes include technetium, rhenium, gallium, gadolinium, indium, copper, and the like, including isotopes $^{111}$In, $^{99m}$Tc, $^{64}$Cu, $^{67}$Cu, $^{67}$Ga, $^{68}$Ga, and the like. Additional illustrative examples of radionuclide imaging agents are described in U.S. Pat. No. 7,128,893, the disclosure of which is incorporated herein by reference. Additional illustrative chelating groups are tripeptide or tetrapeptides, including but not limited to tripeptides having the formula:

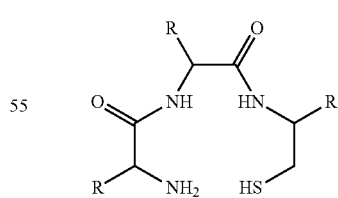

wherein R is independently selected in each instance II, alkyl, heteroalkyl, cycloalkyl, heterocyclyl, alkenyl, alkynyl, aryl, heteroaryl, arylalkyl, heteroarylalkyl, and the like, each of which is optionally substituted. It is to be understood that one R includes a heteroatom, such as nitro, oxygen, or sulfur, and is the point of attachment of linker L. Illustratively, the following chelating groups are described:

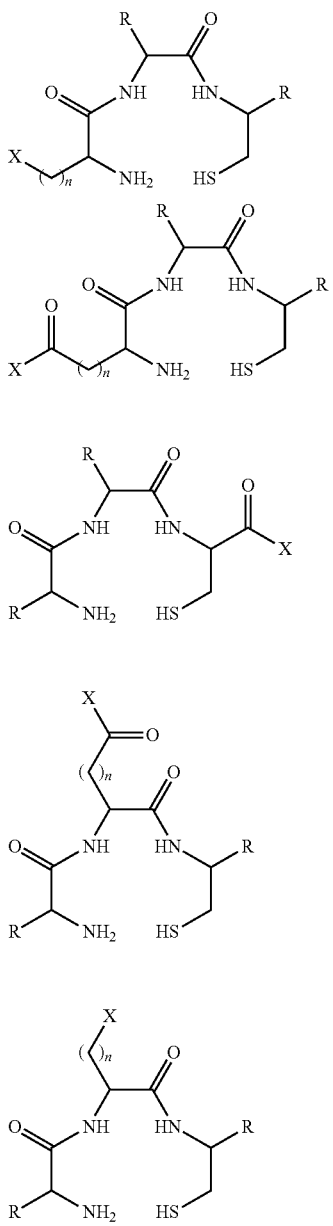

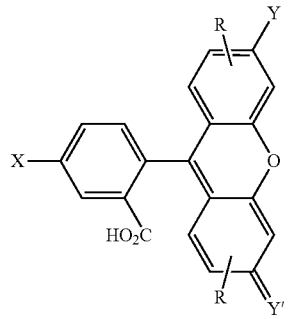

where X is oxygen, nitrogen, or sulfur, and where X is attached to linker L; Y is $OR^a$, $NR^a_2$, or $NR^a_3{}^+$; and Y' is O, $NR^a$, or $NR^a_2{}^+$; where each R is independently selected in each instance from H, fluoro, sulfonic acid, sulfonate, and salts thereof, and the like; and $R^a$ is hydrogen or alkyl. Further illustrative fluorescent agents include compounds of the following formula:

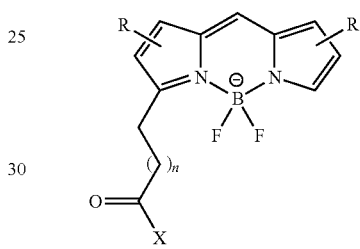

where X is oxygen, nitrogen, or sulfur, and where X is attached to linker L; and each R is independently selected in each instance from H, alkyl, heteroalkyl, and the like; and n is an integer from 0 to about 4.

Illustrative imaging agents also include, but are not limited to, PET imaging agents, and FRET imaging agents. Illustrative PET imaging agents include $^{18}F$, $^{11}C$, $^{64}Cu$, $^{65}Cu$, and the like. Illustrative FRET imaging agents include $^{64}Cu$, $^{65}Cu$, and the like. It is to be understood that in the case of $^{18}F$ and $^{11}C$, the imaging isotope may be directly attached to the linker, or alternatively may be present on a structure attached to the linker. For example in the case of $^{18}F$, fluoroaryl groups, such as fluorophenyl, difluorophenyl, fluoronitrophenyl, and the like are described. For example in the case of $^{11}C$, alkyl and alkyl aryl are described.

In another embodiment, the drug can be any molecule capable of modulating or otherwise modifying cell function, including pharmaceutically active compounds. Illustrative drugs include, but are not limited to, peptides, oligopeptides, retro-inverso oligopeptides, proteins, protein analogs in which at least one non-peptide linkage replaces a peptide linkage, apoproteins, alycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; antiwhere X is oxygen, nitrogen, or sulfur, and where X is attached to linker L, and n is a integer from 1 to about 5.

Illustrative imaging agents also include, but are not limited to, fluorescent agents, such as OREGON GREEN® fluorescent agents, including but not limited to OREGON GREEN® 48, OREGON GREEN® 514, and the like, ALEXA FLUOR® fluorescent agents, including but not limited to ALEXA FLUOR® 488, ALEXA FLUOR® 647, and the like, fluorescein, and related analogs, BODIPY® fluorescent agents, including but not limited to BODIPY® F1, BODIPY® 505, and the like, rhodamine fluorescent agents, including but not limited to tetramethylrhodamine, and the like, DYLIGHT® fluorescent agents, including but not limited to DYLIGHT® 680, DYLIGHT® 800, and the like, CW 800, IRDYE® 800CW, TEXAS RED®, phycoerythrin, and others. Further illustrative fluorescent agents include compounds of the following formula:

convulsants; antinauseants; prostaglandins and prostaglandin analogs; muscle relaxants; anti-inflammatory substances; immunosuppressants, stimulants; decongestants; antiemetics; diuretics; antispasmodics; antiasthmatics; anti-Parkinson agents; expectorants; cough suppressants; mucolytics; and mineral and nutritional additives.

Illustrative chemotherapeutic agents also include, but are not limited to, compounds that are cytotoxic, enhance tumor permeability, inhibit tumor cell proliferation, promote apoptosis, decrease anti-apoptotic activity in target cells, used to treat diseases caused by infectious agents, enhance an endogenous immune response directed to the pathogenic cells, or are useful for treating a disease state caused by the pathogenic cells. Such chemotherapeutic agents may operate by any of a large variety of mechanisms of action. For example, cytotoxic compounds may disrupt any of a wide variety of cellular mechanisms that are important for cell survival and/or cell proliferation and/or cause cell death or apoptosis.

Illustrative chemotherapeutic agents also include, but are not limited to, adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, TAXOTERE®, cyclophosphamide, daunomycin, rhizoxin, T2 toxin, plant alkaloids, prednisone, hydroxyurea, teniposide, mitomycins, discodermolides, microtubule inhibitors, epothilones, tubulysins, cyclopropyl benz[e]indolone, seco-cyclopropyl benz[e]indolone, O-Ac-seco-cyclopropyl benz[e]indolone, bleomycin and any other antibiotic, nitrogen mustards, nitrosureas, vinca alkaloids, such as vincristine, vinblastine, vindesine, vinorelbine and analogs and derivative thereof such as deacetylvinblastine monohydrazide (DAVLBH), colchicine, colchicine derivatives, allocolchicine, thiocolchicine, trityl cysteine, halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, rapamycins, such as sirolimus and everolimus, and any other drug or toxin.

In another embodiment, at least one drug is selected from cryptophycins, bortezomib, thiobortezomib, tubulysins, aminopterin, rapamycins, such as everolimus and sirolimus, paclitaxel, docetaxel, doxorubicin, daunorubicin, α-amanatin, verucarin, didemnin B, geldanomycin, purvalanol A, ispinesib, budesonide, dasatinib, epothilones, maytansines, and tyrosine kinase inhibitors, including analogs and derivatives of each of the foregoing.

Other drugs that can be included in the conjugates described herein include amphotericin B, acyclovir, trifluridine, ganciclovir, zidovudine, amantadine, ribavirin, and the like.

In another embodiment, at least one drug is a tubulysin. As used herein, the term "tubulysin" generally refers to the compounds described herein and analogs and derivatives thereof. It is also to be understood that any corresponding pharmaceutically acceptable salt is also included in the illustrative embodiments described herein. Illustrative derivatives of tubulysins include, but are not limited to, those compounds that may be synthetically prepared from the compounds described herein. It is to be understood that such derivatives may include prodrugs of the compounds described herein, compounds described herein that include one or more protection or protecting groups, including compounds that are used in the preparation of other compounds described herein.

As described herein, the tubulysin compounds may be inhibitors of tubulin polymerization, and also may be DNA-alkylators.

Illustrative tubulysins include, but are not limited to compounds of the formula

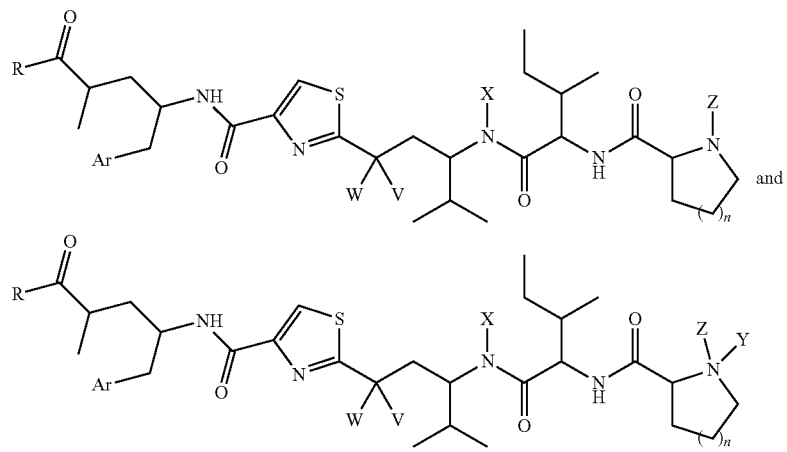

and pharmaceutical salts thereof are described, where n is 1-3;

V is hydrogen, $OR^2$, or halo, and W is hydrogen, $OR^2$, or alkyl, where $R^2$ is independently selected in each instance from hydrogen, alkyl, and $C(O)R^3$, where $R^3$ is alkyl, cycloalkyl, alkenyl, aryl, or arylalkyl, each of which is optionally substituted; providing that $R^2$ is not H when both V and W are $OR^2$; or V and W are taken together with the attached carbon to form a carbonyl;

X is hydrogen, alkyl, such as $C_{1-4}$ alkyl, or alkenyl, such as $C_{2-4}$ alkenyl, each of which is optionally substituted;

Z is alkyl or $C(O)R^4$, where $R^4$ is alkyl, $CF_3$, or aryl; or when Y is present, Z is alkyl; and Y is O;

Ar is aryl, such as phenyl, or heteroaryl, each of which is optionally substituted; and R is OH or R and the carbonyl to which it is attached is a carboxylic acid derivative, such as an acylhydrazide.

In another embodiment, X is CH$_2$QR$^9$, where Q is —N—, —O—, or —S—; R$^9$ is hydrogen or alkyl, alkenyl, cycloalkyl, aryl, or arylalkyl, each of which is optionally substituted, or C(O)R$^{10}$, where R$^{10}$ is hydrogen or alkyl, alkenyl, cycloalkyl, aryl, or arylalkyl In another embodiment, R$^9$ and Q are taken together to form S(O)$_2$R$^{10}$, P(O)(OR$^{10a}$)$_2$, where R$^{10}$ and OR$^{10a}$ are independently selected in each instance from the group consisting of hydrogen, and alkyl, alkenyl, cycloalkyl, aryl, heteroaryl, and arylalkyl, each of which is optionally substituted, or R$^{10a}$ is a metal cation.

In another embodiment, X is H. Illustrative examples of such compounds, and their preparation are described in J. Med. Chem. 10.1021/jm701321p (2008), the disclosure of which is incorporated herein by reference.

In another embodiment, X is a radical of the formula

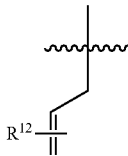

where R$^{12}$ represents 1 or more substituents selected from alkyl, alkenyl, cycloalkyl, aryl, and arylalkyl, each of which is optionally substituted. It is to be understood that other olefins may form by isomerization, depending on the conditions of the reaction and the identity of R$^{12}$. For example, when R$^{12}$ is alkyl, it is appreciated that under the reaction conditions, the double bond can migrate to other carbon atoms along the alkenyl chain, including to form the terminal or ω-olefin.

In another embodiment, X is a radical of the formula

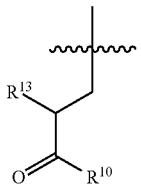

where R$^{13}$ is C(O)R$^{10}$, C(O)OR$^{10}$ or CN, where R$^{10}$ is independently selected in each instance.

In another embodiment, X is CH$_2$—OH.

In another embodiment, X is CH$_2$—X$^A$, where X$^A$ is halogen, OS(O)$_2$R$^{10}$, OP(O)(OR$^{10a}$)R$^{10}$, or OP(O)(OR$^{10a}$)$_2$; where R$^{10}$ and R$^{10a}$ are independently selected in each instance from the group consisting of hydrogen, alkyl, alkenyl, cycloalkyl, aryl, and arylalkyl, each of which is optionally substituted, or R$^{10a}$ is a metal cation.

In another embodiment of any of the foregoing embodiments, Ar is optionally substituted aryl. In another embodiment of any of the foregoing embodiments, Ar is a radical of the formula

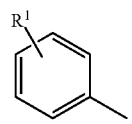

where R$^1$ is hydrogen, or R$^1$ represents 1 to 3 substituents independently selected from the group consisting of halo, nitro, carboxylate or a derivative thereof, cyano, hydroxyl, alkyl, haloalkyl, alkoxy, haloalkoxy, and OR$^6$, where R$^6$ is hydrogen or optionally substituted alkyl, heteroalkyl, aryl, a phenol protecting group, a prodrug moiety, C(O)R$^7$, P(O)(OR$^8$)$_2$, or SO$_3$R$^8$, where R$^7$ and R$^8$ are independently selected in each instance from hydrogen, or alkyl, alkenyl, cycloalkyl, heterocyclyl, aryl, heteroaryl, and arylalkyl, each of which is optionally substituted, or R$^8$ is a metal cation are described.

In another embodiment of any of the foregoing embodiments, Z is methyl. In another embodiment of any of the foregoing embodiments, R$^1$ is H. In another embodiment of any of the foregoing embodiments, R$^1$ is OR$^6$ at C(4), where R$^6$ is hydrogen, alkyl, or COR$^7$. In another embodiment of any of the foregoing embodiments, V is hydrogen, and W is OC(O)R$^3$. In another embodiment of any of the foregoing embodiments, V is hydrogen, and W is acetyloxy.

In another embodiment of any of the foregoing embodiments, the compounds of the various formulae have the following absolute configuration:

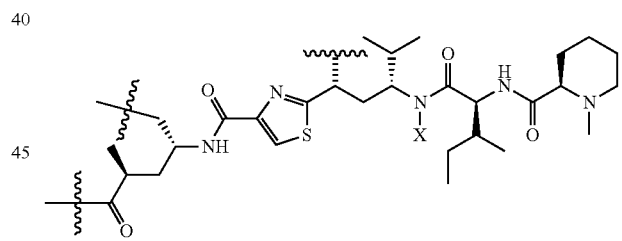

at each of the indicated asymmetric carbon atoms.

Additional illustrative tubulysins that are useable in the conjugates described herein include the following:

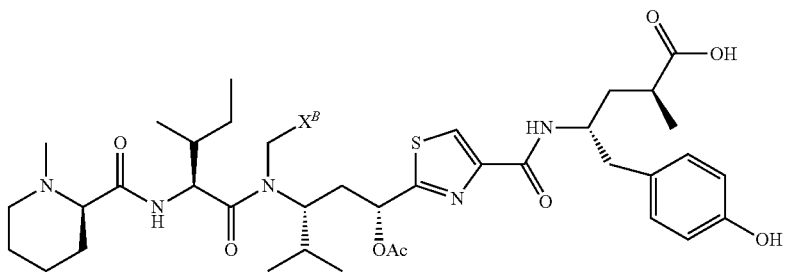

| Tubulysin | $X^B$ |
|---|---|
| EC0313 | —O—CH$_3$ |
| EC0346 | —O—(CH$_2$)$_2$—OH |
| EC0356 | —O—(CH$_2$)$_2$CH(CH$_3$)$_2$ |
| EC0374 | —S—(CH$_2$)$_2$—SH |
| EC0386 | —OH |
| EC0550 | —(CH$_2$)$_2$—CH=CH$_2$ |
| EC0560 | —S—(CH$_2$)$_2$—OH |
| EC0575 | —O—C(O)—(CH=CH)—CH$_2$—Cl |
| EC0585 | —NH—C(O)—CH$_2$CH(CH$_3$)$_2$ |
| EC0611 | —O—(CH$_2$)$_2$CH$_3$ |
| EC0623 | —S—(CH$_2$)$_2$CH$_3$ | and pharmaceutical salts thereof.

In another embodiment, the tubulysin is a naturally occurring tubulysin. Natural tubulysins are generally linear tetrapeptides consisting of N-methyl pipecolic acid (Mep), isoleucine (Ile), an unnatural aminoacid called tubuvalin (Tuv), and either an unnatural aminoacid called tubutyrosine (Tut, an analog of tyrosine) or an unnatural aminoacid called tubuphenylalanine (Tup, an analog of phenylalanine). In another embodiment, naturally occurring tubulysins, and analogs and derivatives thereof, of the following general formula are described

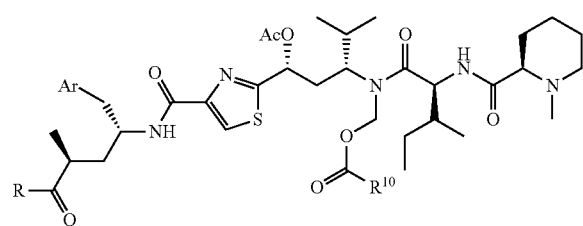

and pharmaceutical salts thereof, where Ar, R, and $R^{10}$ are as described in the various embodiments herein.

In another embodiment, the naturally occurring tubulysins of the following general formula are described

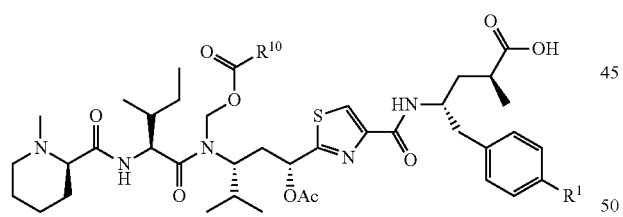

| Factor | $R^{10}$ | $R^1$ |
|---|---|---|
| A | (CH$_3$)$_2$CHCH$_2$ | OH |
| B | CH$_3$(CH$_2$)$_2$ | OH |
| C | CH$_3$CH$_2$ | OH |
| D | (CH$_3$)$_2$CHCH$_2$ | H |
| E | CH$_3$(CH$_2$)$_2$ | H |
| F | CH$_2$CH$_3$ | H |
| G | (CH$_3$)$_2$C=CH | OH |
| H | CH$_3$ | H |
| I | CH$_3$ | OH | and pharmaceutical salts thereof.

It is to be understood that the conjugate of the tubulysin or analog or derivative thereof may be formed at any position. Illustratively, conjugates of tubulysins are described where the linker (L) is attached to any of the following positions:

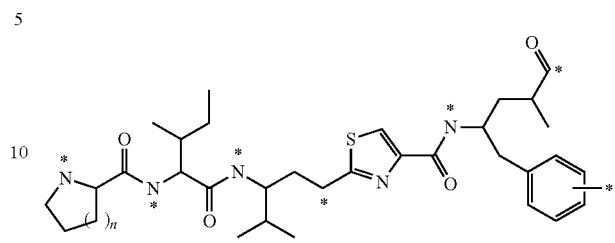

where the (*) symbol indicates optional attachment locations.

In another embodiment, compounds are described herein where the conjugate is formed at the terminal carboxylic acid group or the terminal acylhydrazine derivative group of each of the tybulysins described herein.

Additional tubulysins useful in preparing the conjugates described herein are described in US patent application publication Nos. 2006/0128754 and 2005/0239713, the disclosures of which are incorporated herein by reference. Additional tubulysins useful in preparing the conjugates described herein are described in co-pending U.S. patent application publication No. 2010/0240701 the disclosure of which is incorporated herein by reference. Tubulysins may also be prepared are described in Peltier et al., "The Total Synthesis of Tubulysin D," J. Am. Chem. Soc. 128:16018-19 (2006), the disclosure of which is incorporated herein by reference.

In another embodiment, at least one drug is a rapamycin. As used herein, the term "a rapamycin" is understood to include sirolimus (rapamycin), temsirolimus, everolimus, and ridaforolimus, and related compounds, and compounds of the formula

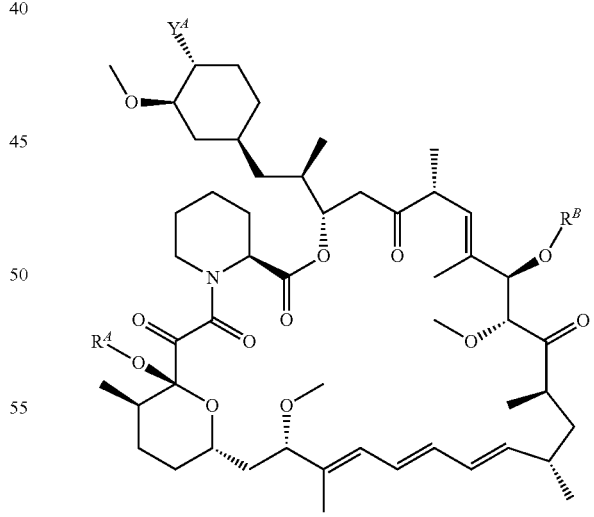

and pharmaceutically acceptable salts thereof, wherein
$Y^A$ is OR$^C$ or OCH$_2$CH$_2$OR$^C$;
one of R$^A$, R$^B$, or R$^C$ is a bond connected to L; and
the other two of R$^A$, R$^B$, and R$^C$ are independently selected in each case from the group consisting of hydrogen, optionally substituted heteroalkyl, prodrug forming group, and C(O)R$^D$, where R$^D$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted is described.

In another embodiment, at least one drug is a vinca alkaloids, such as vincristine, vinblastine, vindesine, vinorelbine and analogs and derivative thereof such as deacetylvinblastine monohydrazide (DAVLBH).

In another embodiment, at least one drug is a mitomycin, or an analog or derivative thereof.

In another embodiment, the conjugates described herein include at least two drugs, including those described herein. In one variation, the drugs are the same. In another variation, at least two of the drugs are different. In another variation, the two or more drugs are selected from vinca alkaloids, cryptophycins, bortezomib, thiobortezomib, tubulysins, aminopterin, rapamycins, such as everolimus and sirotimus, paclitaxel, docetaxel, doxorubicin, daunorubicin, α-amanatin, verucarin, didemnin B, geldanomycin, purvalanol A, ispinesib, budesonide, dasatinib, epothilones, maytansines, and tyrosine kinase inhibitors, including analogs and derivatives of each of the foregoing.

As used herein, the term "linker" includes is a chain of atoms that connects two or more functional parts of a molecule to form a conjugate. Illustratively, the chain of atoms is selected from C, N, O, S, Si, and P, or C, N, O, S, and P, or C, N, O, and S. The chain of atoms covalently connects different functional capabilities of the conjugate, such as binding ligands, drugs, diagnostic agents, imaging agents, and the like. The linker may have a wide variety of lengths, such as in the range from about 2 to about 100 atoms in the contiguous backbone. The atoms used in forming the linker may be combined in all chemically relevant ways, such as chains of carbon atoms forming alkylene, alkenylene, and alkynylene groups, and the like; chains of carbon and oxygen atoms forming ethers, polyoxyalkylene groups, or when combined with carbonyl groups forming esters and carbonates, and the like; chains of carbon and nitrogen atoms forming amines, imines, polyamines, hydrazines, hydrazones, or when combined with carbonyl groups forming amides, ureas, semicarbazides, carbazides, and the like; chains of carbon, nitrogen, and oxygen atoms forming alkoxyamines, alkoxylamines, or when combined with carbonyl groups forming urethanes, amino acids, acyloxylamines, hydroxamic acids, and the like; and many others. In addition, it is to be understood that the atoms forming the chain in each of the foregoing illustrative embodiments may be either saturated or unsaturated, thus forming single, double, or triple bonds, such that for example, alkanes, alkenes, alkynes, imines, and the like may be radicals that are included in the linker. In addition, it is to be understood that the atoms forming the linker may also be cyclized upon each other or be part of cyclic structure to form divalent cyclic structures that form the linker, including cycloalkanes, cyclic ethers, cyclic amines, and other heterocycles, arylenes, heteroarylenes, and the like in the linker. In this latter arrangement, it is to be understood that the linker length may be defined by any pathway through the one or more cyclic structures. Illustratively, the linker length is defined by the shortest pathway through the each one of the cyclic structures. It is to be understood that the linkers may be optionally substituted at any one or more of the open valences along the chain of atoms, such as optional substituents on any of the carbon, nitrogen, silicon, or phosphorus atoms. It is also to be understood that the linker may connect the two or more functional parts of a molecule to form a conjugate at any open valence, and it is not necessary that any of the two or more functional parts of a molecule forming the conjugate are attached at any apparent end of the linker.

In another embodiment, the linker (L) comprises a radical of the formula

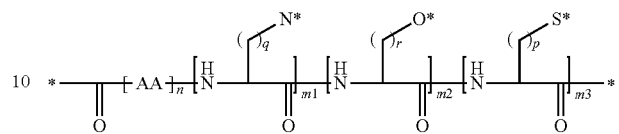

where m1, m2, m3, n, p, q, and r are integers that are each independently selected from the range of 0 to about 8, providing that at least one of m1, m2, m3, n, p, q, and r is not 0; AA is an amino acid; and drugs are optionally attached at one or more of the (*) atoms. It is to be understood that the drugs may be directly attached, or attached through additional portions of the linker (L). In another embodiment, AA is a naturally occurring amino acid of either the natural or unnatural configuration. In another embodiment, one or more of AA is a hydrophilic amino acid. In another embodiment, one or more of AA is Asp and/or Arg. In another embodiment, the integer n is 1 or greater. In another embodiment, the integer n is 2 or greater. In another embodiment, the integer n is 3 or greater. In another embodiment, the integer n is 4 or greater. In another embodiment, the integer n is 5 or greater. In another aspect, the integer q is 1 or greater. In another embodiment, the integer m1 is 1 or greater. In another embodiment, the integer m is 1. In another embodiment, the integer m2 is 1 or greater. In another embodiment, the integer m2 is 1. In another embodiment, the integer m3 is 1 or greater. In another embodiment, the integer in3 is 1. In another embodiment, the integer p is 1 or greater. In another embodiment, the integer p is 1. In another embodiment, the integer p is 2. In another embodiment, the integer q is 1 or greater. In another embodiment, the integer q is 1. In another embodiment, the integer q is 2. In another embodiment, the integer r is 1 or greater. In another embodiment, the integer r is 1. In another embodiment, the integer r is 2.

It is to be understood that all combinations of the foregoing embodiments are described herein. For example, in another embodiment, n is 1 or greater, and m1 is one or greater; or n is 1 or greater, m1 is 1, and q is 1; and so forth. For example, in another embodiment, n is 1 or greater, and m2 is one or greater; or n is 2 or greater, m2 is 1, and q is 1; or n is 2 or greater, m3 is 1, q is 1, and p is 1; and so forth. For example, in another embodiment, n is 1 or greater, and m1 is one or greater; or n is 2 or greater, m3 is 1, and q is 1; or n is 2 or greater, m2 is q is 1, and p is 1; or n is 2 or greater, m1 is 1, q is and r is 1; or n is 2 or greater, m3 is 1, q is 1, p is 1, and r is 1; and so forth.

In another embodiment, the polyvalent linker includes one or more divalent hydrophilic radicals, as described herein, which may also be referred to as spacer linkers. It is appreciated that the arrangement and/or orientation of the various hydrophilic linkers may be in a linear or branched fashion, or both. For example, the hydrophilic linkers may form the backbone of the linker forming the conjugate between the ligand and the one or more drugs. Alternatively, the hydrophilic portion of the linker may be pendant to or attached to the backbone of the chain of atoms connecting the binding ligand B to the one or more drugs D. In this latter arrangement, the hydrophilic portion may be proximal or distal to the backbone chain of atoms.

In another embodiment, the linker is generally linear, and the hydrophilic groups are arranged generally in a series to form a chain-like linker in the conjugate. Said another way, the hydrophilic groups form some or all of the backbone of the linker in such a linear linker embodiment.

In another embodiment, the linker is branched with hydrophilic groups. In this branched embodiment, the hydrophilic groups may be proximal to the backbone or distal to the backbone. In each of these arrangements, the linker is generally more spherical or cylindrical in shape. In another embodiment, the linker is shaped like a bottle-brush. In another embodiment, the backbone of the linker is formed by a linear series of amides, and the hydrophilic portion of the linker is formed by a parallel arrangement of branching side chains, such as by connecting monosaccharides, sulfonates, and the like, and derivatives and analogs thereof.

It is understood that the linker (L) may be neutral or ionizable under certain conditions, such as physiological conditions encountered in vivo. For ionizable linkers, under the selected conditions, the linker may deprotonate to form a negative ion, or alternatively become protonated to form a positive ion. It is appreciated that more than one deprotonation protonation event may occur. In addition, it is understood that the same linker may deprotonate and protonate to form inner salts or zwitterionic compounds.

In another embodiment, the hydrophilic spacer linkers are neutral, an in particular neutral under physiological conditions, the linkers do not significantly protonate nor deprotonate. In another embodiment, the hydrophilic spacer linkers may be protonated to carry one or more positive charges. It is understood that the protonation capability is condition dependent. In one aspect, the conditions are physiological conditions, and the linker is protonated in vivo. In another embodiment, the spacers include both regions that are neutral and regions that may be protonated to carry one or more positive charges. In another embodiment, the spacers include both regions that may be deprotonated to carry one or more negative charges and regions that may be protonated to carry one or more positive charges. It is understood that in this latter embodiment that zwitterions or inner salts may be formed.

In another embodiment, the regions of the linkers that may be deprotonated to carry a negative charge include carboxylic acids, such as aspartic acid, glutamic acid, and longer chain carboxylic acid groups, and sulfuric acid esters, such as alkyl esters of sulfuric acid. In another embodiment, the regions of the linkers that may be protonated to carry a positive charge include amino groups, such as polyamino-alkylenes including ethylene diamines, propylene diamines, butylene diamines and the like, and/or heterocycles including pyrollidines, piperidines, piperazines, and other amino groups, each of which is optionally substituted. In another embodiment, the regions of the linkers that are neutral include poly hydroxyl groups, such as sugars, carbohydrates, saccharides, inositols, and the like, and/or polyether groups, such as polyoxyalkylene groups including polyoxyethylene, polyoxypropylene, and the like.

In another embodiment, the hydrophilic spacer linkers described herein include are formed primarily from carbon, hydrogen, and oxygen, and have a carbon/oxygen ratio of about 3:1 or less, or of about 2:1 or less. In another embodiment, the hydrophilic linkers described herein include a plurality of ether functional groups. In another embodiment, the hydrophilic linkers described herein include a plurality of hydroxyl functional groups. Illustrative fragments and radicals that may be used to form such linkers include polyhydroxyl compounds such as carbohydrates, polyether compounds such as polyethylene glycol units, and acid groups such as carboxyl and alkyl sulfuric acids. In one variation, oligoamide spacers, and the like may also be included in the linker.

Illustrative divalent hydrophilic linkers include carbohydrates such as saccharopeptides as described herein that include both a peptide feature and sugar feature; glucuronides, which may be incorporated via [2+3] cyclization, also known as click chemistry; β-alkyl glycosides, such as of 2-deoxyhexapyranoses (2-deoxyglucose, 2-deoxyglucuronide, and the like), and β-alkyl mannopyranosides. Illustrative PEG groups include those of a specific length range from about 4 to about 20 PEG groups. Illustrative alkyl sulfuric acid esters may also be introduced with click chemistry directly into the backbone. Illustrative oligoamide spacers include EDTA and DTPA spacers, β-amino acids, and the like.

In another embodiment, the polyvalent linker L comprises one or more polyethers, such as the linkers of the following formulae:

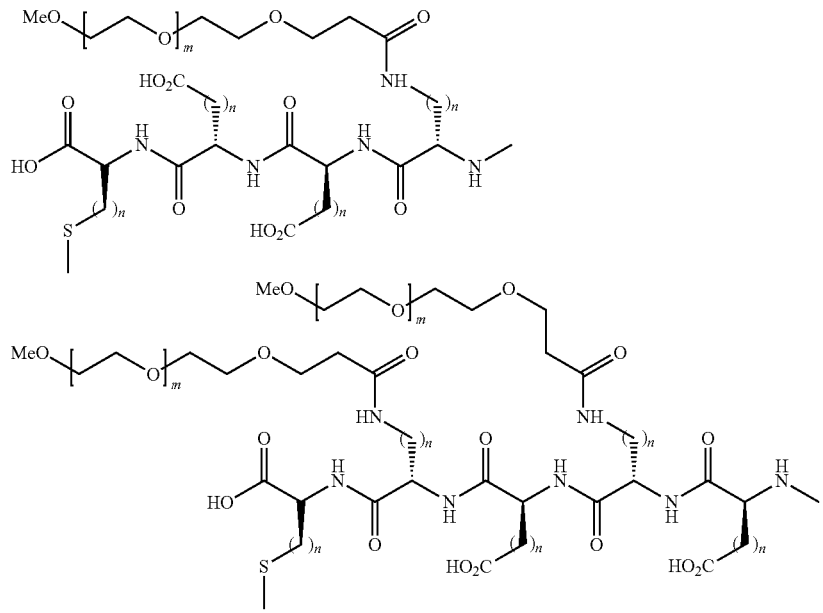

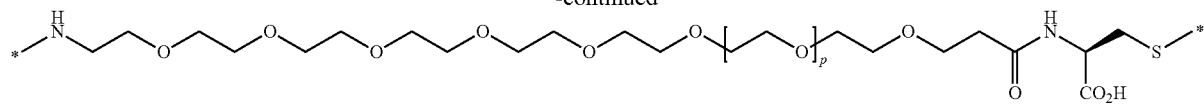

where m is an integer independently selected in each instance from 1 to about 8; p is an integer selected 1 to about 10; and n is an integer independently selected in each instance from 1 to about 3. In one aspect, m is independently in each instance 1 to about 3. In another aspect, n is 1 in each instance. In another aspect, p is independently in each instance about 4 to about 6. Illustratively, the corresponding polypropylene polyethers corresponding to the foregoing are contemplated herein and may be included in the conjugates as hydrophilic spacer linkers. In addition, it is appreciated that mixed polyethylene and polypropylene polyethers may be included in the conjugates as hydrophilic spacer linkers. Further, cyclic variations of the foregoing polyether compounds, such as those that include tetrahydrofuranyl, 1,3-dioxanes, 1,4-dioxanes, and the like are contemplated herein.

In another embodiment, the polyvalent linker L comprises a plurality of hydroxyl functional groups, such as linkers that incorporate monosaccharides, oligosaccharides, polysaccharides, and the like. It is to be understood that the polyhydroxyl containing spacer linkers comprises a plurality of —(CROH)— groups, where R is hydrogen or alkyl.

In another embodiment, the polyvalent linker L comprises one or more of the following fragments:

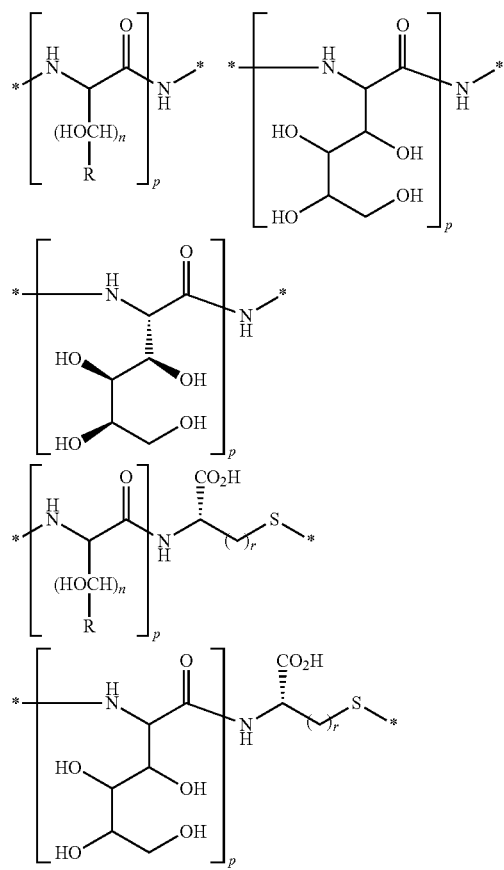

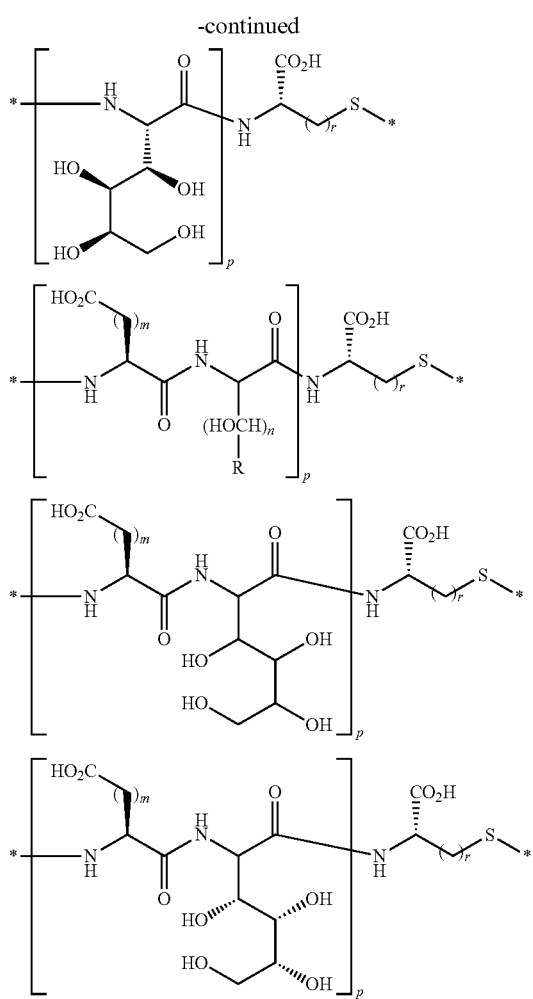

wherein R is H, alkyl, cycloalkyl, or arylalkyl; m is an integer from 1 to about 3; n is an integer from 1 to about 5, or from 2 to about 5, p is an integer from 1 to about 5, and r is an integer selected from 1 to about 3. In one aspect, the integer n is 3 or 4. In another aspect, the integer p is 3 or 4. In another aspect, the integer r is 1.

In another embodiment, the polyvalent linker L comprises one or more of the following fragments:

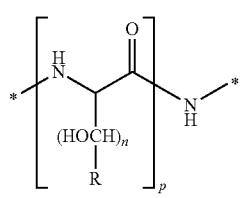

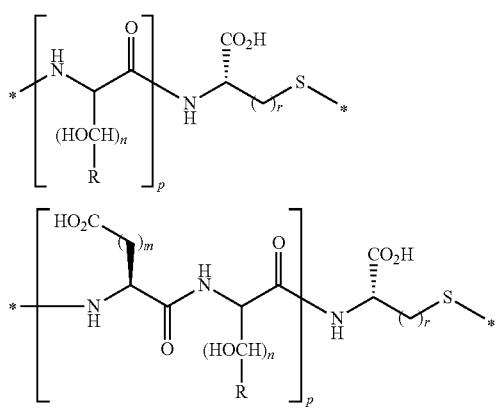

wherein R is H, alkyl, cycloalkyl, or arylalkyl; m is an integer from 1 to about 3; n is an integer from 1 to about 5, or from 2 to about 5, p is an integer from 1 to about 5, and r is an integer selected from 1 to about 3. In one aspect, the integer n is 3 or 4. In another aspect, the integer p is 3 or 4. In another aspect, the integer r is 1.

In another embodiment, the polyvalent linker L comprises one or more of the following cyclic polyhydroxyl groups:

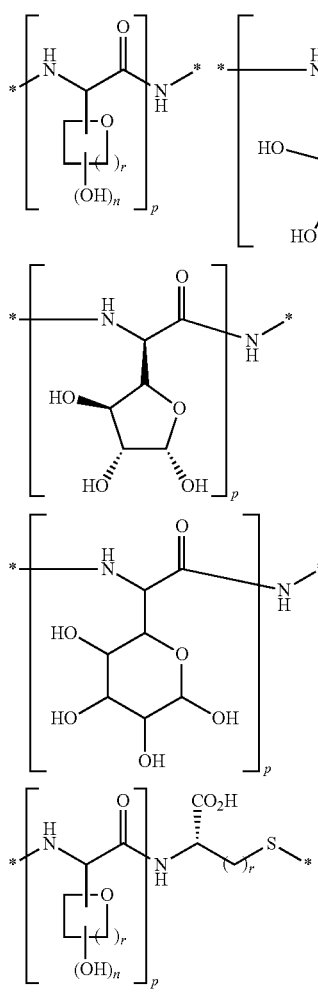

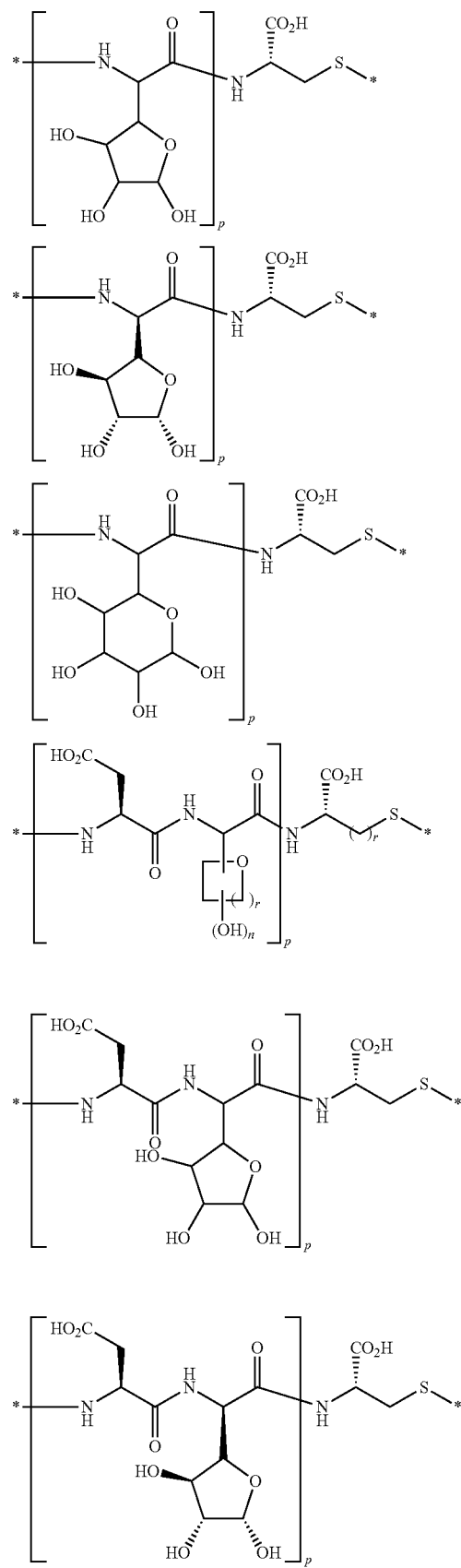

-continued

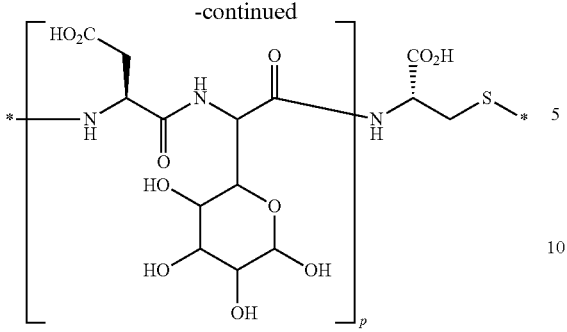

wherein n is an integer from 2 to about 5, p is an integer from 1 to about 5, and r is an integer from 1 to about 4. In one aspect, the integer n is 3 or 4. In another aspect, the integer p is 3 or 4. In another aspect, the integer r is 2 or 3. It is understood that all stereochemical forms of such sections of the linkers are contemplated herein. For example, in the above formula, the section may be derived from ribose, xylose, glucose, mannose, galactose, or other sugar and retain the stereochemical arrangements of pendant hydroxyl and alkyl groups present on those molecules. In addition, it is to be understood that in the foregoing formulae, various deoxy compounds are also contemplated. Illustratively, compounds of the following formulae are contemplated:

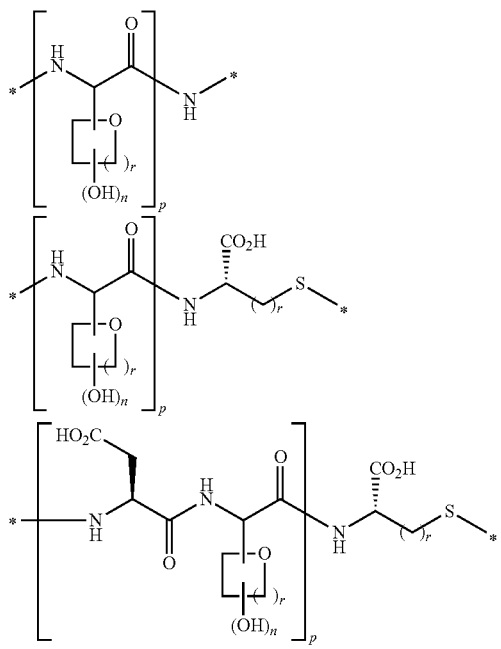

wherein n is equal to or less than r, such as when r is 2 or 3, n is 1 or 2, or 1, 2, or 3, respectively.

In another embodiment, the polyvalent linker L comprises one or more polyhydroxyl radicals of the following formula:

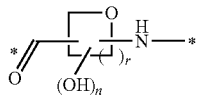

wherein n and r are each an integer selected from 1 to about 3. In one aspect, the linker includes one or more polyhydroxyl compounds of the following formulae:

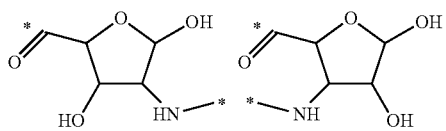

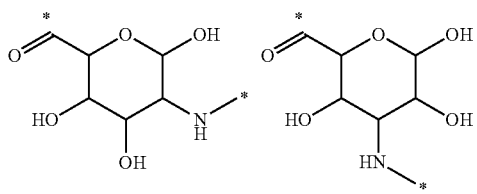

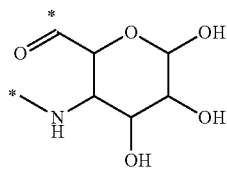

It is understood that all stereochemical forms of such sections of the linkers are contemplated herein. For example, in the above formula, the section may be derived from ribose, xylose, glucose, mannose, galactose, or other sugar and retain the stereochemical arrangements of pendant hydroxyl and alkyl groups present on those molecules.

In another embodiment, the polyvalent linker L comprises one or more polyhydroxyl groups that are spaced away from the backbone of the linker. In one embodiment, such carbohydrate groups or polyhydroxyl groups are connected to the back bone by a triazole group, forming triazole-linked hydrophilic spacer linkers. Illustratively, the linker includes fragments of the following formulae:

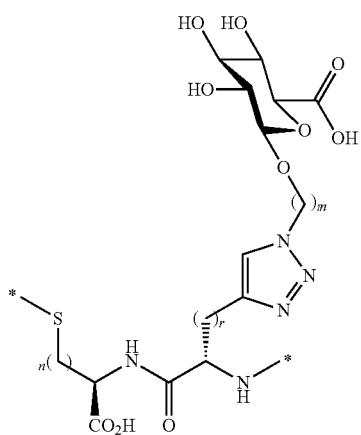

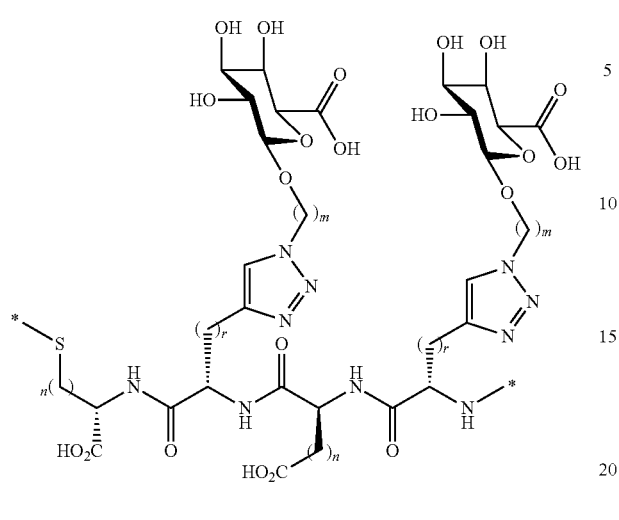

wherein n, m, and r are integers and are each independently selected in each instance from 1 to about 5. In one illustrative aspect, m is independently 2 or 3 in each instance. In another aspect, r is 1 in each instance. In another aspect, n is 1 in each instance. In one variation, the group connecting the polyhydroxyl group to the backbone of the linker is a different heteroaryl group, including but not limited to, pyrrole, pyrazole, 1,2,4-triazole, furan, oxazole, isoxazole, thienyl, thiazole, isothiazole, oxadiazole, and the like. Similarly, divalent 6-membered ring heteroaryl groups are contemplated. Other variations of the foregoing illustrative hydrophilic spacer linkers include oxyalkylene groups, such as the following formulae:

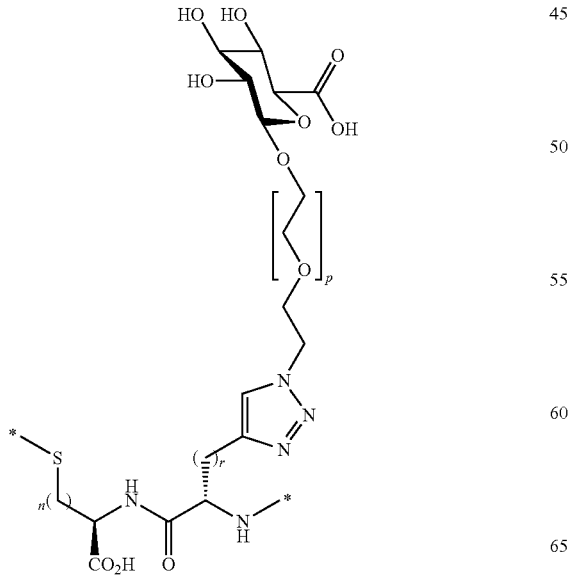

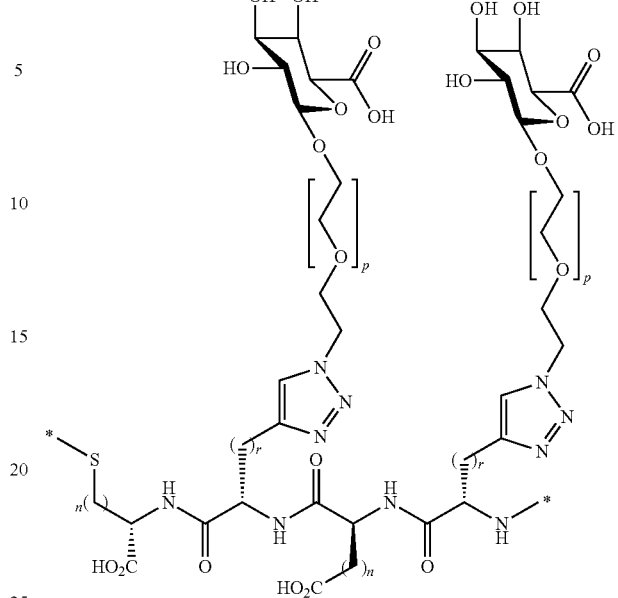

wherein n and r are integers and are each independently selected in each instance from to about and p is an integer selected from 1 to about 4.

In another embodiment, the polyvalent linker L comprises one or more carbohydrate groups or polyhydroxyl groups connected to the back bone by an amide group, forming amide-linked hydrophilic spacer linkers. Illustratively, such linkers include fragments of the following formulae:

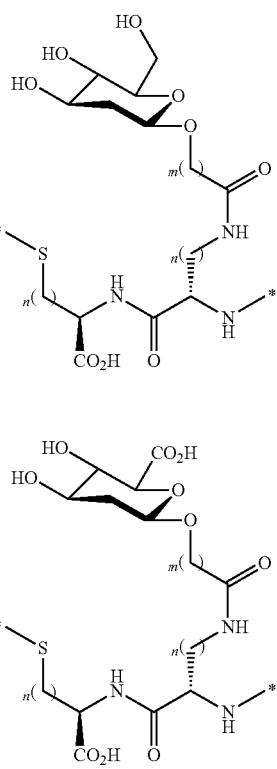

-continued

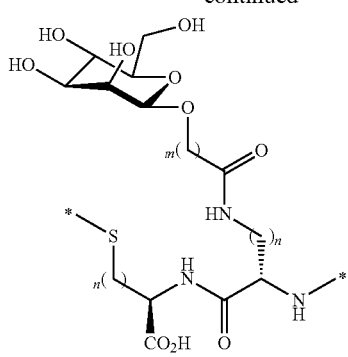

wherein n is an integer selected from 1 to about 3, and m is an integer selected from 1 to about 22. In one illustrative aspect, n is 1 or 2. In another illustrative aspect, in is selected from about 6 to about 10, illustratively 8. In one variation, the group connecting the polyhydroxyl group to the backbone of the linker is a different functional group, including but not limited to, esters, ureas, carbamates, acythydrazones, and the like. Similarly, cyclic variations are contemplated. Other variations of the foregoing illustrative hydrophilic spacer linkers include oxyalkylene groups, such as the following formulae:

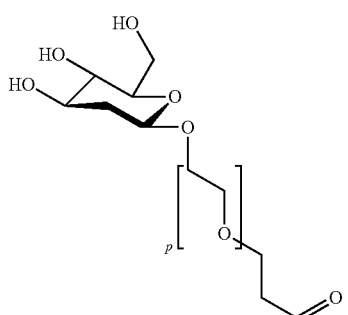

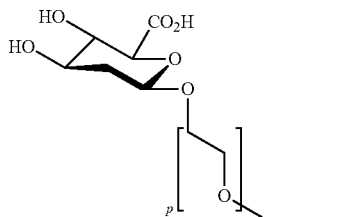

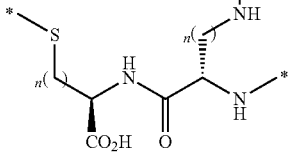

-continued

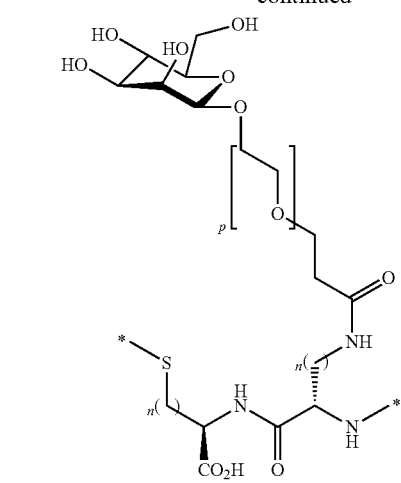

wherein n and r are integers and are each independently selected in each instance from 1 to about 5; and p is an integer selected from 1 to about 4.

In another embodiment, the polyvalent linker L comprises one or more of the following fragments:

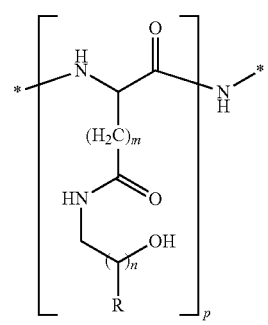

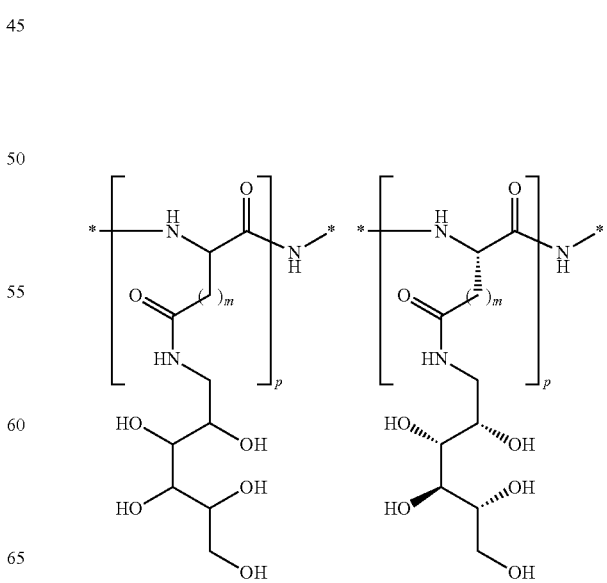

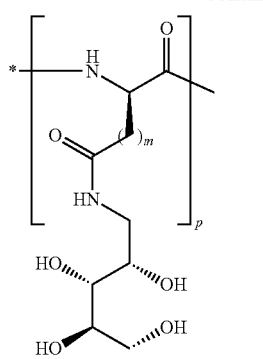
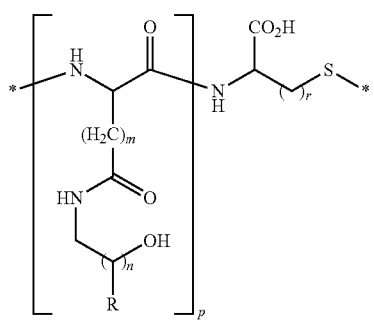
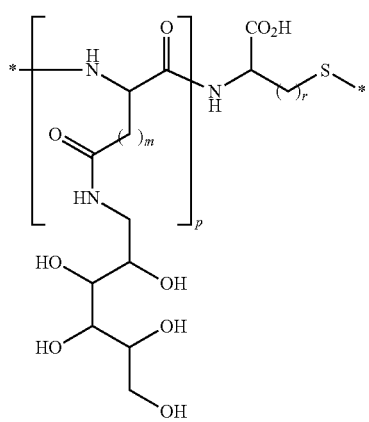
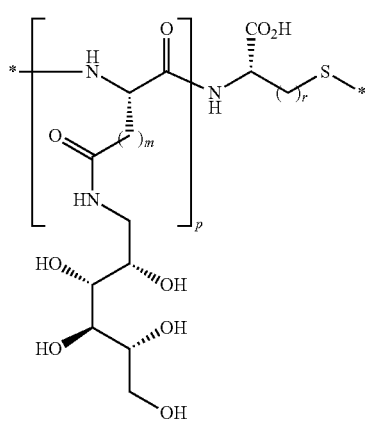
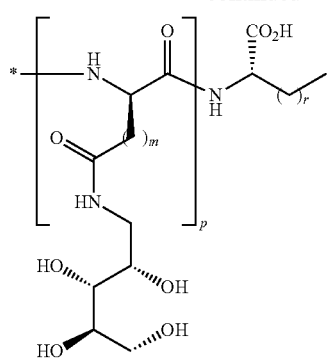
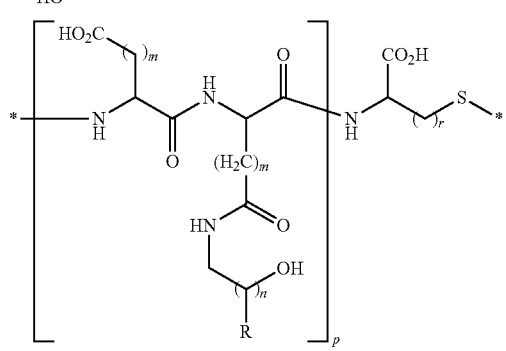
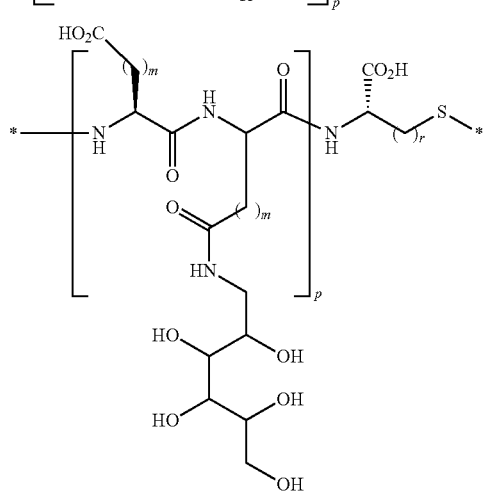
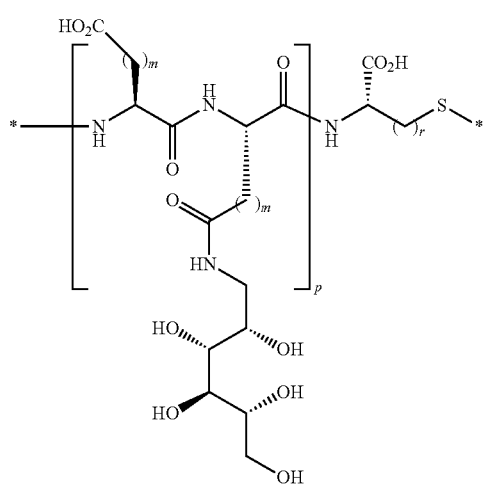

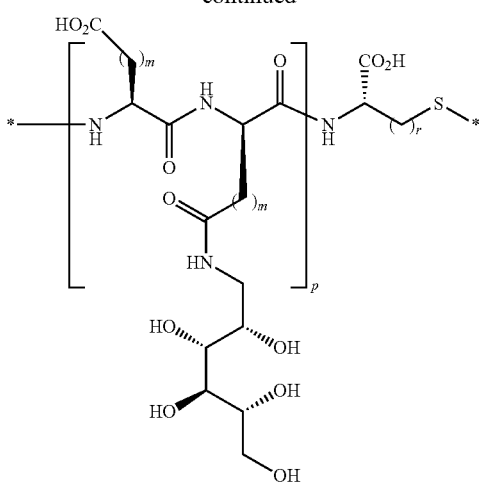

wherein R is H, alkyl, cycloalkyl, or arylalkyl; m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the polyvalent linker L comprises one or more of the following fragments:

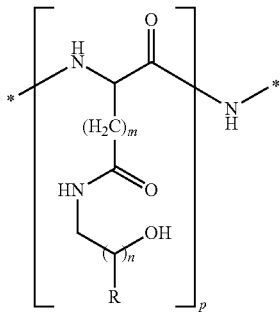

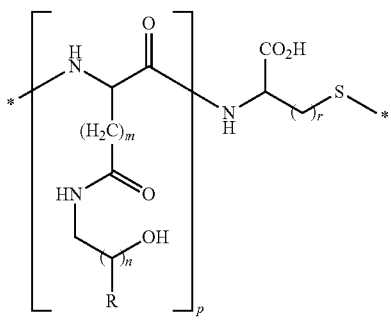

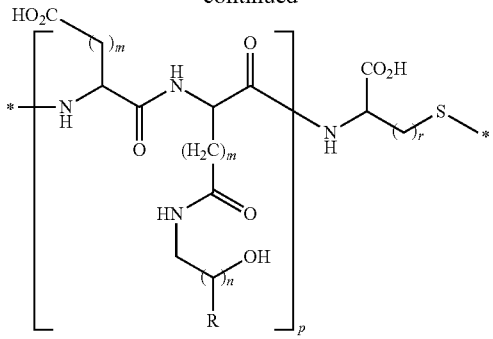

wherein R is H, alkyl, cycloalkyl, or arylalkyl; m is an independently selected integer from 1 to about 3; n is an integer from 2 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the polyvalent linker comprises one or more of the following fragments:

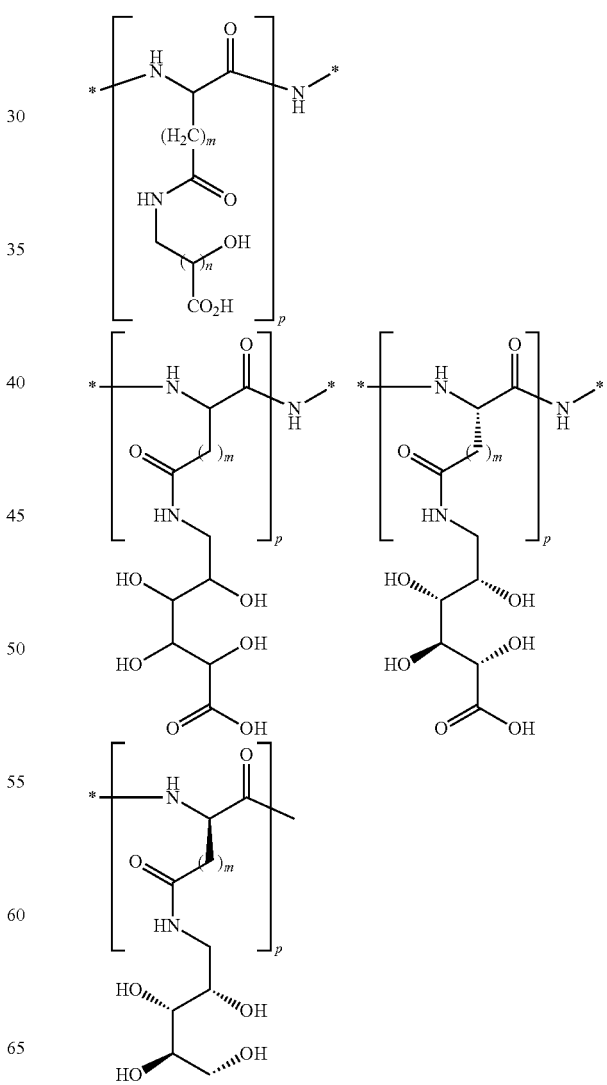

51
-continued
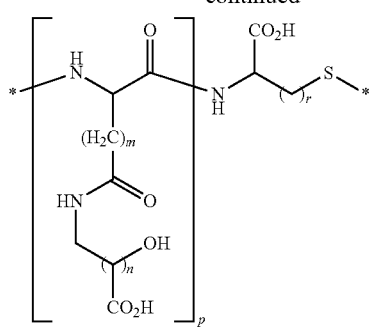
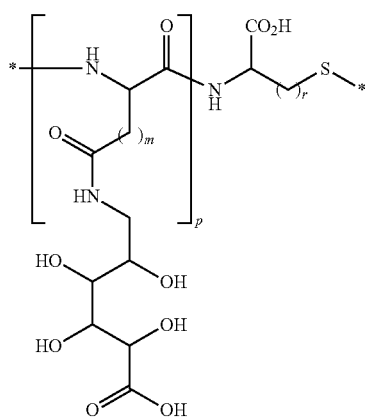
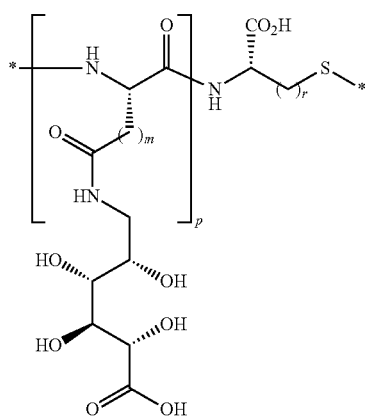
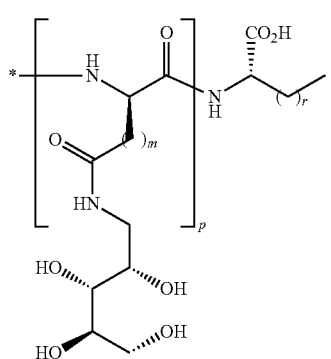
52
-continued
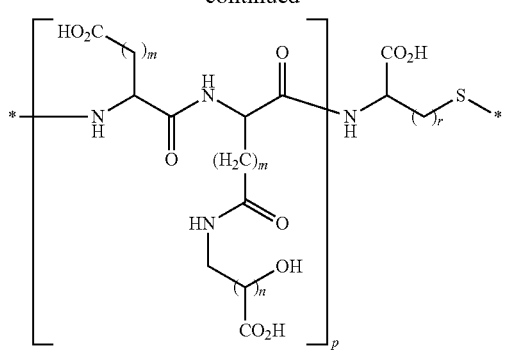
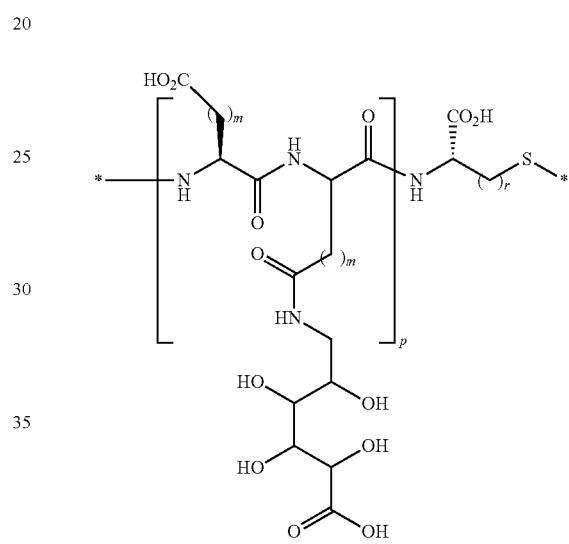
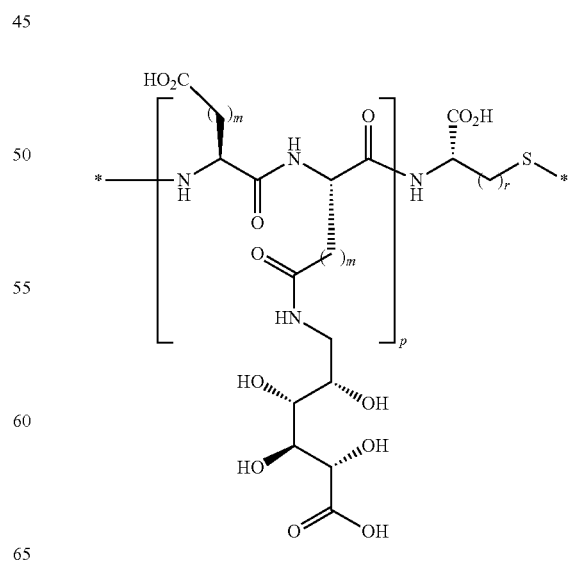

-continued

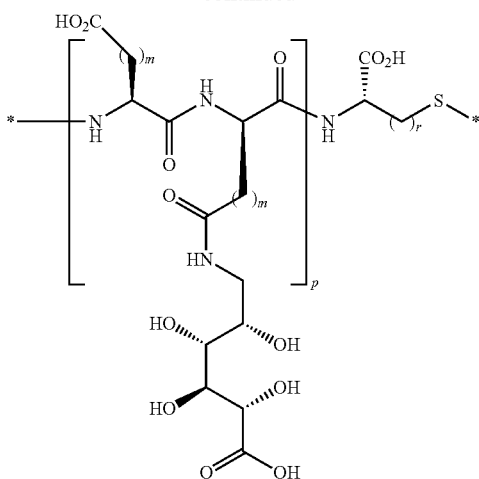

wherein m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the polyvalent lit e comprises one or more of the following fragments:

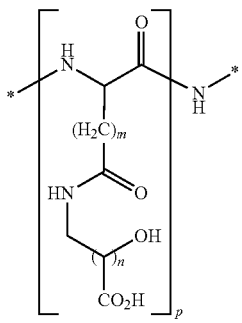

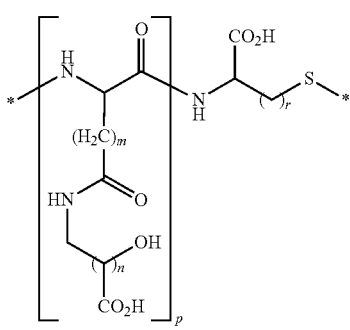

-continued

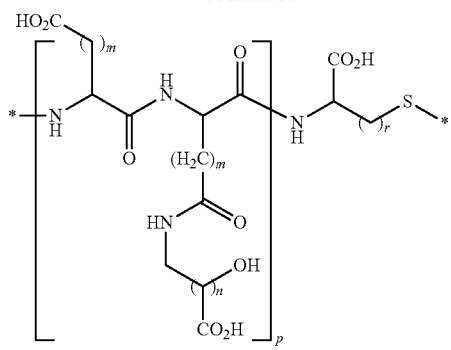

wherein m is an independently selected integer from 1 to about 3; n is an integer from 2 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the polyvalent linker L comprises one or more of the following fragments:

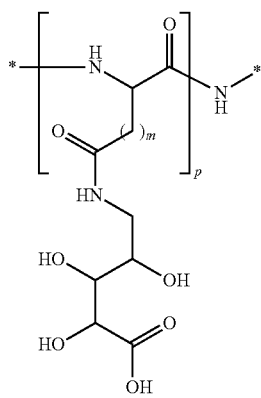

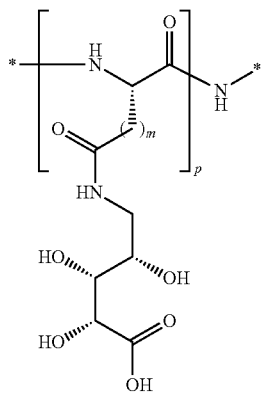

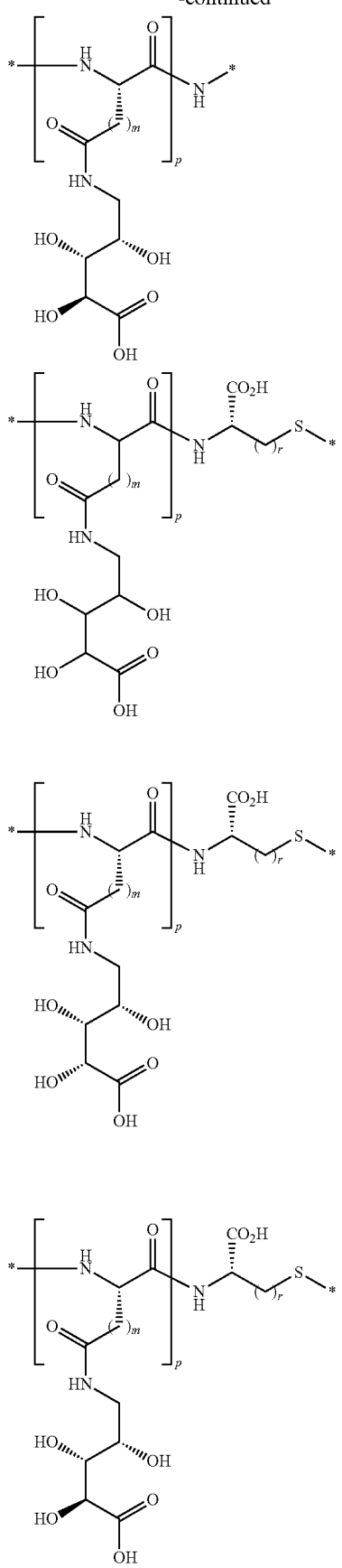

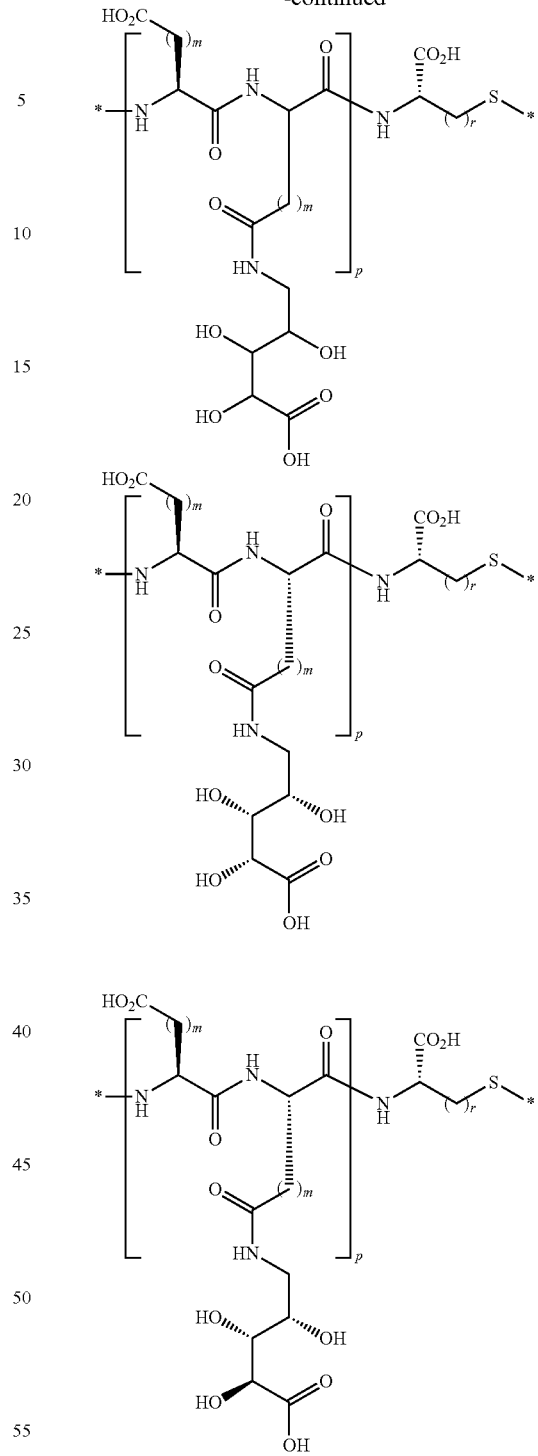

wherein m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the polyvalent linker L comprises a combination of backbone and branching side motifs such as is illustrated by the following formulae

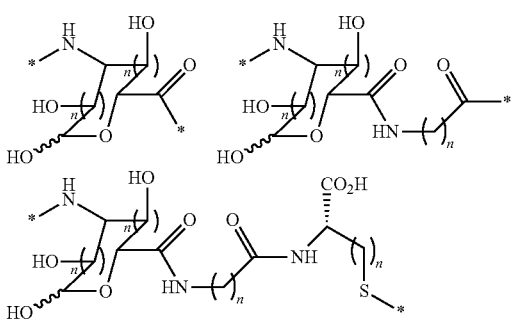

wherein n is an integer independently selected in each instance from 0 to about 3. The above formula are intended to represent 4, 5, 6, and even larger membered cyclic sugars. In addition, it is to be understood that the above formula may be modified to represent deoxy sugars, where one or more of the hydroxy groups present on the formulae are replaced by hydrogen, alkyl, or amino. In addition, it is to be understood that the corresponding carbonyl compounds are contemplated by the above formulae, where one or more of the hydroxyl groups is oxidized to the corresponding carbonyl.

In addition, in this illustrative embodiment, the pyranose includes both carboxyl and amino functional groups and (a) can be inserted into the backbone and (b) can provide synthetic handles for branching side chains in variations of this embodiment. Any of the pendant hydroxyl groups may be used to attach other chemical fragments, including additional sugars to prepare the corresponding oligosaccharides. Other variations of this embodiment are also contemplated, including inserting the pyranose or other sugar into the backbone at a single carbon, i.e. a Spiro arrangement, at a geminal pair of carbons, and like arrangements. For example, one or two ends of the linker, or the drug ID, or the binding ligand B may be connected to the sugar to be inserted into the backbone in a 1,1; 1,2; 1,3; 1,4; 2,3, or other arrangement.

In another embodiment, the hydrophilic spacer linkers described herein include are formed primarily from carbon, hydrogen, and nitrogen, and have a carbon/nitrogen ratio of about 3:1 or less, or of about 2:1 or less. In one aspect, the hydrophilic linkers described herein include a plurality of amino functional groups.

In another embodiment, the polyvalent linker L comprises one or more amino groups of the following formulae:

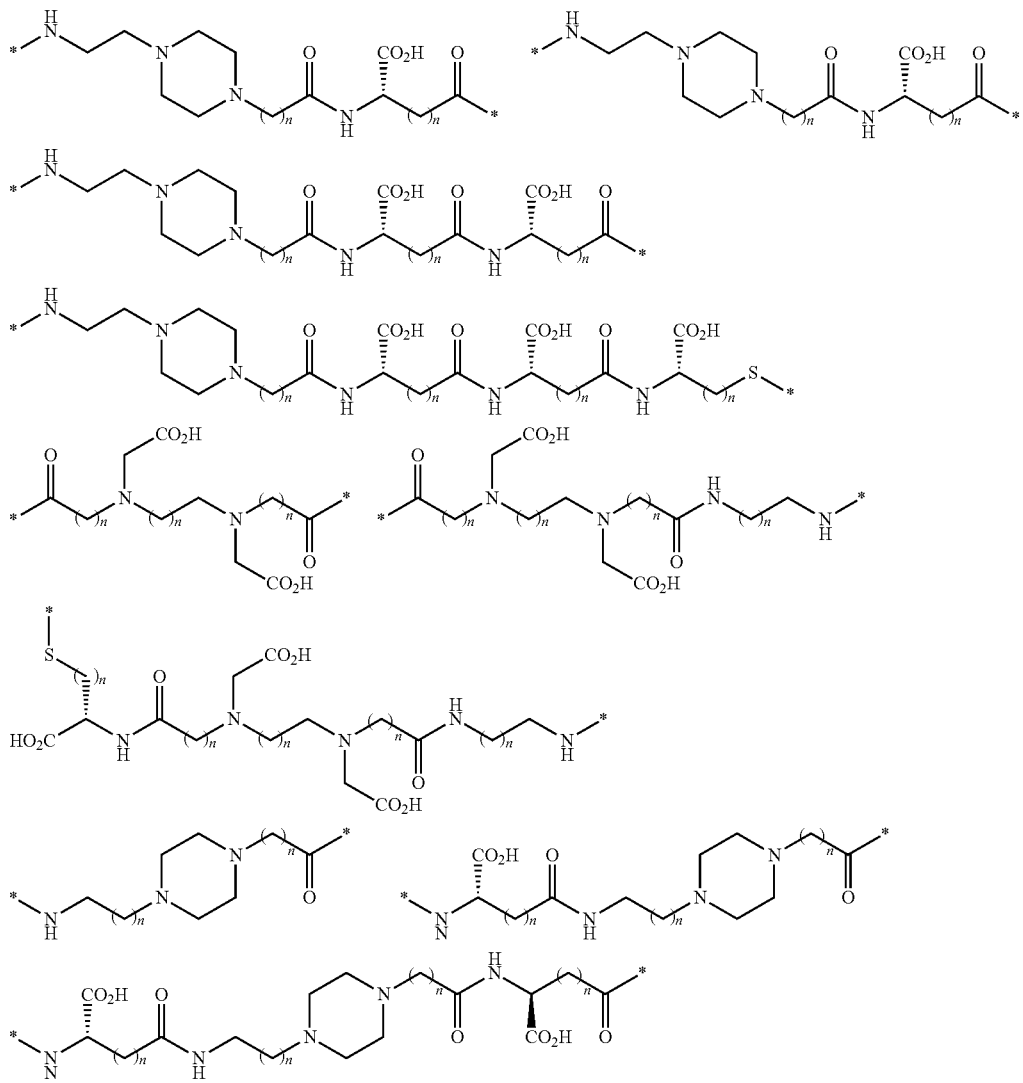

-continued

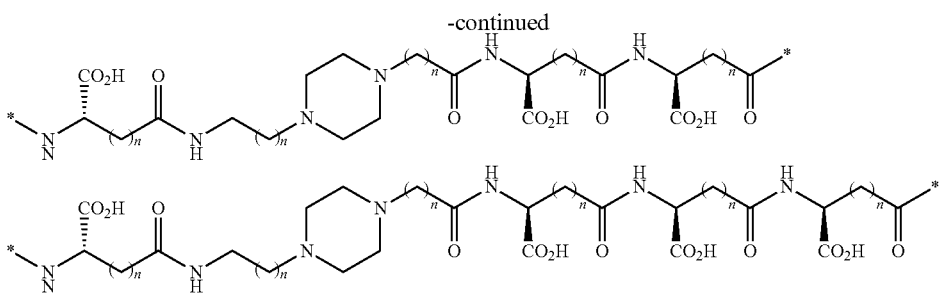

where n is an integer independently selected in each instance from 1 to about 3. In one aspect, the integer n is independently 1 or 2 in each instance. In another aspect, the integer n is 1 in each instance.

In another embodiment, the polyvalent linker L comprises one or more sulfuric acid esters, such as an alkyl ester of sulfuric acid. Illustratively, the linker includes the following formula(e):

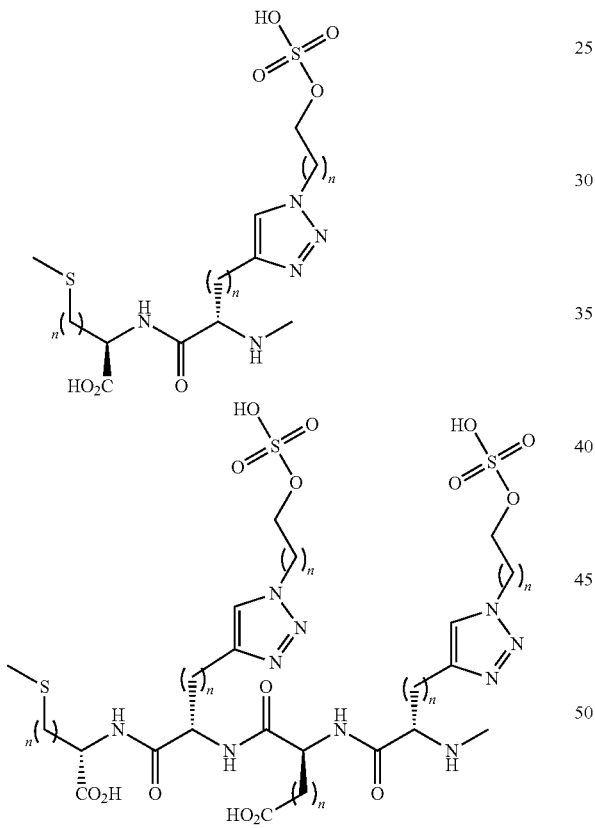

where n is an integer independently selected in each instance from 1 to about 3. Illustratively, n is independently 1 or 2 in each instance.

It is understood, that in such polyhydroxyl, polyamino, carboxylic acid, sulfuric acid, and like linkers that include free hydrogens bound to heteroatoms, one or more of those free hydrogen atoms may be protected with the appropriate hydroxyl, amino, or acid protecting group, respectively, or alternatively may be blocked as the corresponding pro-drugs, the latter of which are selected for the particular use, such as pro-drugs that release the parent drug under general or specific physiological conditions.

In another embodiment, the polyvalent linker comprises one or more of the following divalent radicals:

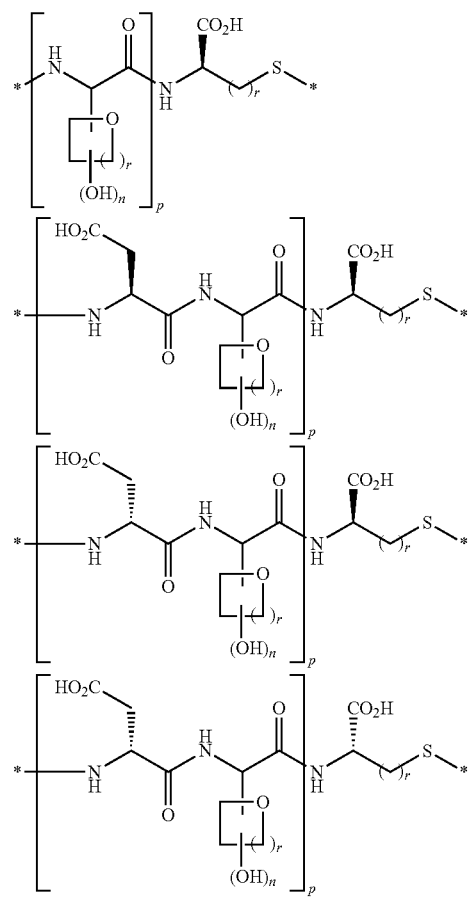

wherein n is an integer from 2 to about 5, p is an integer from 1 to about 5, and r is an integer from 1 to about 4, as described above.

It is to be further understood that in the foregoing embodiments, open positions, such as (*) atoms are locations for attachment of the binding ligand (B) or any drug (D) to be delivered. In addition, it is to be understood that such attachment of either or both of B and any D may be direct or through an intervening linker comprising one or more of the radicals described herein. In addition, (*) atoms may form releasable linkers with any drug D, or other portion of the linker L.

In another embodiment, the hydrophilic spacer linker comprises one or more carbohydrate containing or polyhydroxyl group containing linkers. In another embodiment, the hydrophilic spacer linker comprises at least three carbohydrate containing or polyhydroxyl group containing linkers. In another embodiment, the hydrophilic spacer linker comprises one or more carbohydrate containing or polyhydroxyl group containing linkers, and one or more aspartic acids. In another embodiment, the hydrophilic spacer linker comprises one or more carbohydrate containing or polyhydroxyl group containing linkers, and one or more glutamic acids. In another embodiment, the hydrophilic spacer linker comprises one or more carbohydrate containing or polyhydroxyl group containing linkers, one or more glutamic acids, one or more aspartic acids, and one or more beta amino alanines. In a series of variations, in each of the foregoing embodiments, the hydrophilic spacer linker also includes one or more cysteines. In another series of variations, in each of the foregoing embodiments, the hydrophilic spacer linker also includes at least one arginine.

In another embodiment, the polyvalent linker L includes a hydrophilic spacer linker comprising one or more divalent 1,4-piperazines that are included in the chain of atoms connecting at least one of the binding ligands (L) with at least one of the drugs (D). In one variation, the hydrophilic spacer linker includes one or more carbohydrate containing or polyhydroxyl group containing linkers. In another variation, the hydrophilic spacer linker includes one or more carbohydrate containing or polyhydroxyl group containing linkers and one or more aspartic acids. In another variation, the hydrophilic spacer linker includes one or more carbohydrate containing or polyhydroxyl group containing linkers and one or more glutamic acids. In a series of variations, in each of the foregoing embodiments, the hydrophilic spacer linker also includes one or more cysteines. In another series of variations, in each of the foregoing embodiments, the hydrophilic spacer linker also includes at least one arginine.

In another embodiment, the hydrophilic spacer linker comprises one or more oligoamide hydrophilic spacers, such as but not limited to aminoethylpiperazinylacetamide.

In another embodiment, the polyvalent linker L includes a hydrophilic spacer linker comprising one or more triazole linked carbohydrate containing or polyhydroxyl group containing linkers. In another embodiment, the hydrophilic spacer linker comprises one or more amide linked carbohydrate containing or polyhydroxyl group containing linkers. In another embodiment, the hydrophilic spacer linker comprises one or more PEG groups and one or more cysteines. In another embodiment, the hydrophilic spacer linker comprises one or more EDTE derivatives.

In another embodiment, the polyvalent linker L includes a divalent radical of the formula

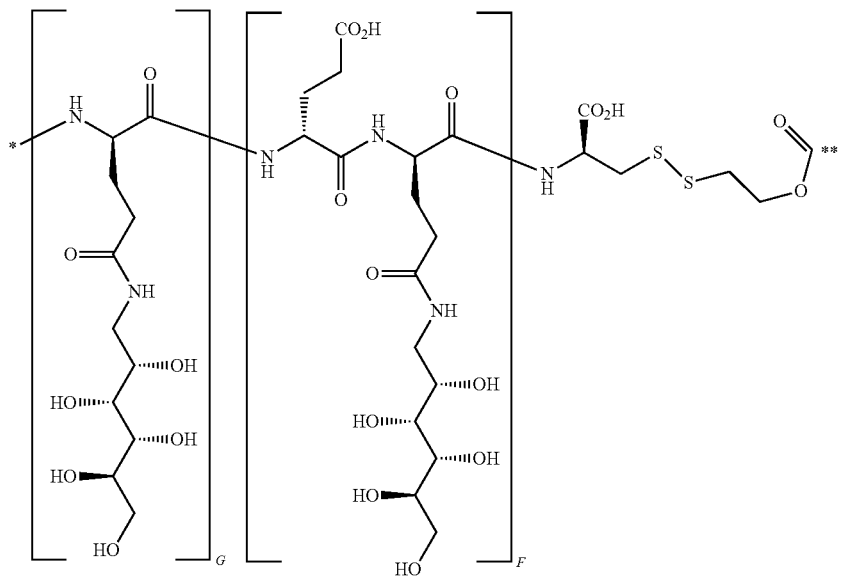

wherein * indicates the point of attachment to a folate and ** indicates the point of attachment to a drug; and F and G are each independently 1, 2, 3 or 4 are described.

In another embodiment, the polyvalent linker L includes a trivalent radical of the formula

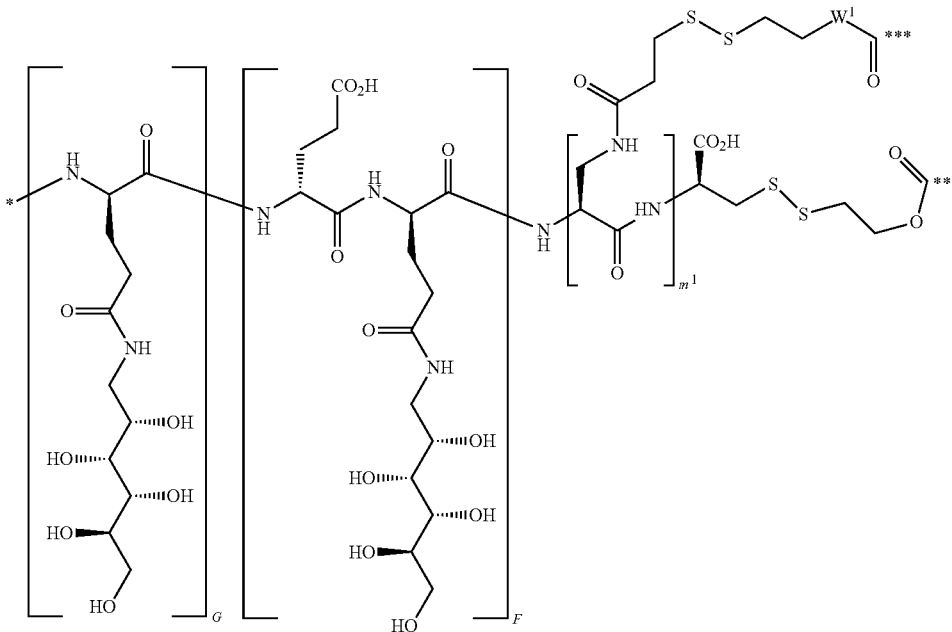

wherein *, , * each indicate points of attachment to the folate receptor binding moiety B, and the one or more drugs D. It is to be understood that when there are fewer drugs, *, , * are substituted with hydrogen or a heteroatom. F and G are each independently 1, 2, 3 or 4; and $W^1$ is NH or O is described. In another aspect, $m^1$ is 0 or 1.

In any of the embodiments described herein heteroatom linkers can also be included in the polyvalent linker L, such as —$NR^1R^2$—, oxygen, sulfur, and the formulae —($NHR^1NHR^2$)—, —SO—, —($SO_2$)—, and —$N(R^3)O$—, wherein $R^1$, $R^2$, and $R^3$ are each independently selected from hydrogen, alkyl, aryl, arylalkyl, substituted aryl, substituted arylalkyl, heteroaryl, substituted heteroaryl, and alkoxyalkyl. It is to be understood that the heteroatom linkers may be used to covalently attach any of the radicals described herein, including drug radicals D to the polyvalent linker, ligand radicals B to the polyvalent linker, or various di and polyvalent radicals that from the polyvalent linker L Illustrative additional bivalent radicals that can be used to form parts of the linker are as follows.

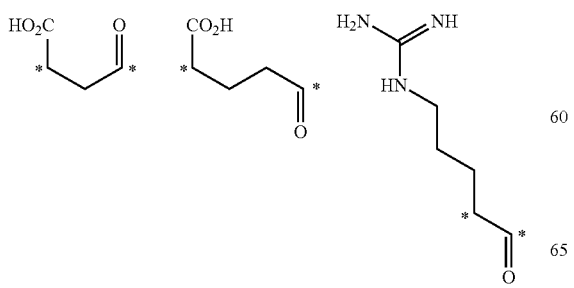

-continued

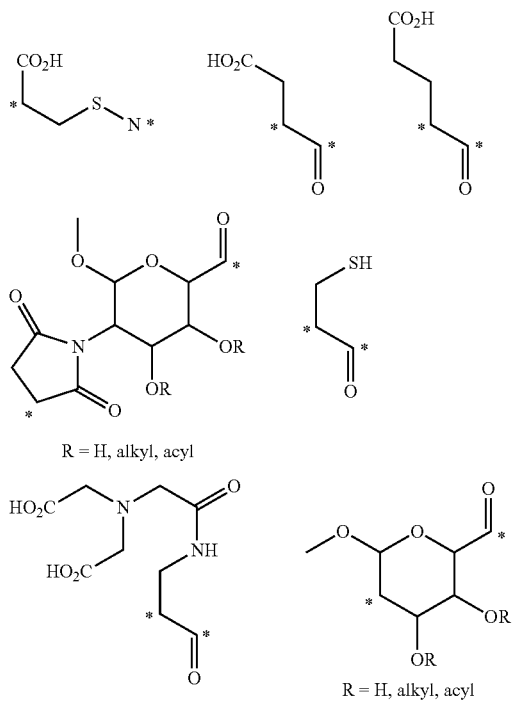

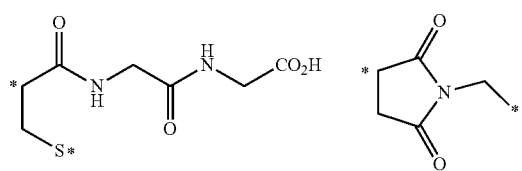

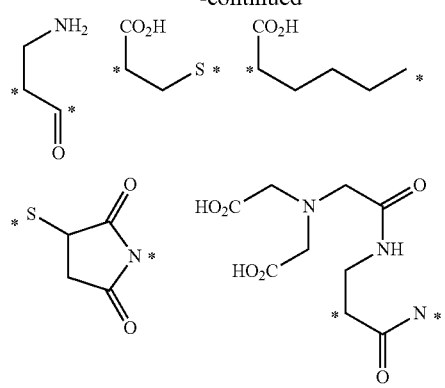
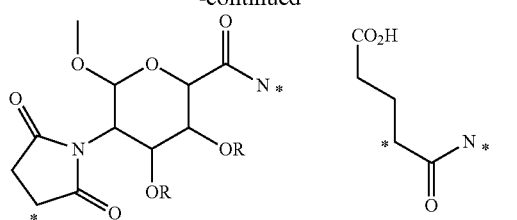
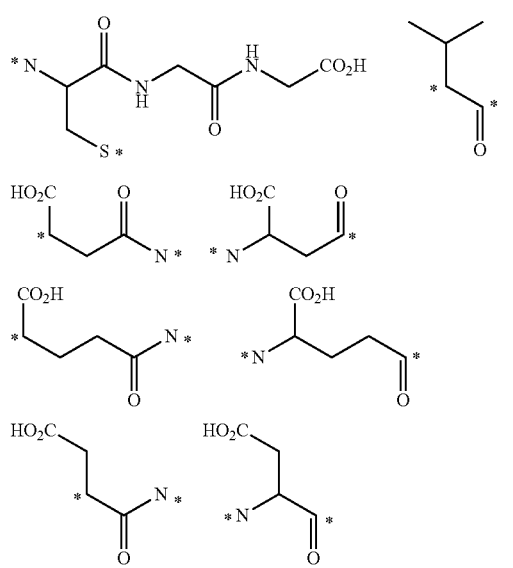

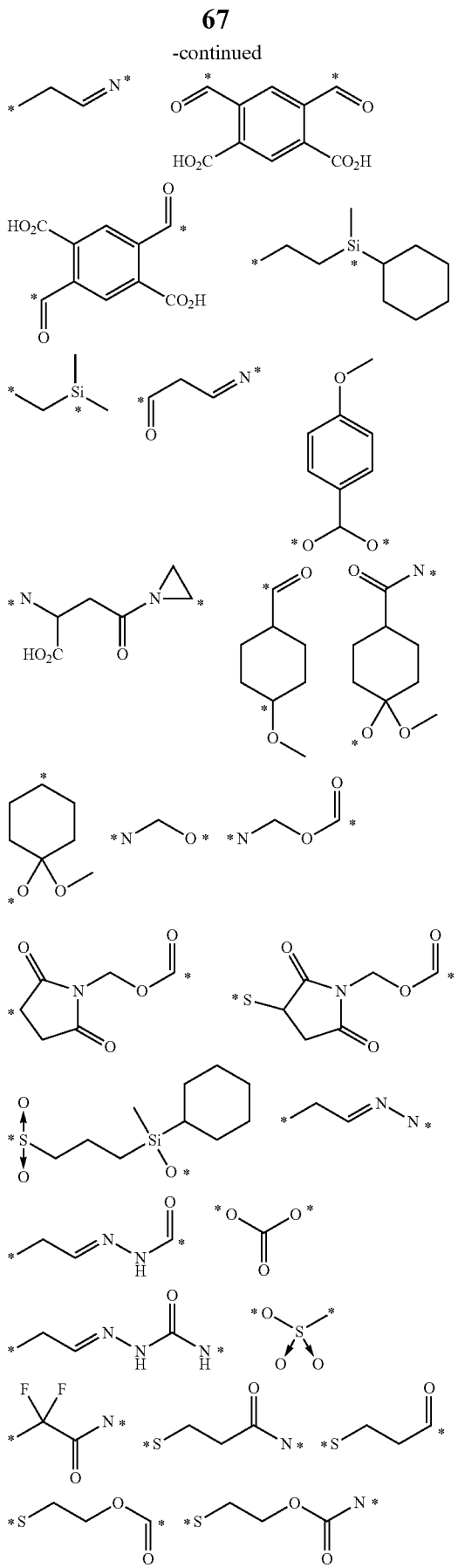
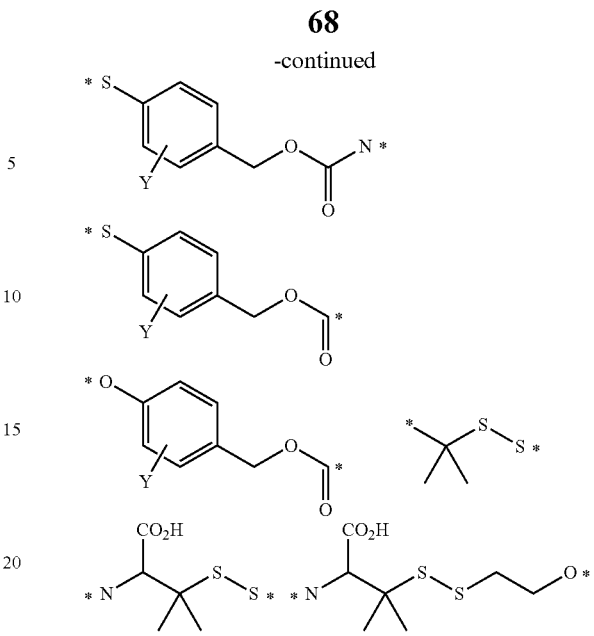

In another embodiment, the polyvalent linker L is a releasable linker.

As used herein, the term "releasable linker" refers to a linker that includes at least one bond that can be broken under physiological conditions when the compounds described herein are delivered to or inside of the target cell. The linker itself may include one or more cleavable, scissile, or breakable bond, or form one or more cleavable, scissile, or breakable bonds with the PSMA binding ligand (B), and/or with one or more of the drugs (D). However, it is appreciated that releasable linkers described herein are advantageously not cleavable, scissile, or breakable until the conjugate containing the releasable linker is at or near the intended target site. Accordingly, releasable linkers described herein do not generally include those linkers that have bonds that are substantially cleavable, scissile, or breakable under non-target conditions, or in non-target tissues. Similarly, releasable linkers described herein do not include those linkers that include bonds that are substantially only cleavable, scissile, or breakable under non-physiological conditions.

The term releasable linker does not generally refer simply to a bond that is labile in vivo, such as in serum, plasma, the gastrointestinal tract, or liver, unless those systems are the target for the cell surface receptor binding ligand. However, after delivery and/or selective targeting, releasable linkers may be cleaved by any process that includes at least one bond being broken in the linker or at the covalent attachment of the linker to B or any D under physiological conditions, such as by having one or more pH-labile, acid-labile, base-labile, oxidatively labile, metabolically labile, biochemically labile, and/or enzyme-labile bonds. It is appreciated that such physiological conditions resulting in bond breaking do not necessarily include a biological or metabolic process, and instead may include a standard chemical reaction, such as a hydrolysis reaction, for example, at physiological pH, or as a result of compartmentalization into a cellular organelle such as an endosome having a lower pH than cytosolic pH.

It is understood that a cleavable bond can connect two adjacent atoms within the releasable linker, and/or connect other linkers with B, and/or any D, as described herein, at any ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an additional heteroatom, a spacer linker, another releasable portion of the linker, any D, or B, following breakage of the bond, the releasable linker is separated from the other moiety. It is to be understood that a linker is a releasable linker when if forms a cleavable, scissile, or breakable bond with the one or more of the drugs (D) is capable of delivery of the one or more drugs (D) in a traceless manner, where the one or more drugs (D) do not include any residual part of the conjugate.

Illustrative radicals that themselves include a cleavable bond, or form a cleavable bond with B and/or any D hemiacetals and sulfur variations thereof, acetals and sulfur variations thereof, hemiaminals, aminals, and the like, or which can be formed from methylene fragments substituted with at least one heteroatom, such as 1-alkoxyalkylene, 1-alkoxycycloalkylene, 1-alkoxyalkylenecarbonyl, 1-alkoxycycloalkylenecarbonyl, and the like. Illustrative releasable linkers described herein include polyvalent linkers that include carbonylarylcarbonyl, carbonyl(carboxyaryl)carbonyl, carbonyl(biscarboxyaryl)carbonyl, haloalkylenecarbonyl, and the like. Illustrative releasable linkers described herein include polyvalent linkers that include alkylene(dialkylsilyl), alkylene(alkylarylsilyl), alkylene(diarylsilyl), (dialkylsilyl)aryl, (alkylarylsilyl)aryl, (diarylsilyl)aryl, and the like. Illustrative releasable linkers described herein include oxycarbonyloxy, oxycarbonyloxyalkyl, sulfonyloxy, oxysulfonylalkyl, and the like. Illustrative releasable linkers described herein include polyvalent linkers that include iminoalkylidenyl, carbonylalkylideniminyl, iminocycloalkylidenyl, carbonylcycloalkylideniminyl, and the like. Illustrative releasable linkers described herein include polyvalent linkers that include alkylenethio, alkylenearylthio, and carbonylalkylthio, and the like. Each of the foregoing fragments is optionally substituted with a substituent $X^2$, as defined herein.

The substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the heteroatom linker can be nitrogen, and the substituent $X^2$ and the heteroatom linker can be taken together with the releasable linker to which they are bound to form an heterocycle.

The heterocycles can be pyrrolidines, piperidines, axazolidines, isoxazolidines, thiazolidines, isothiazolidines, pyrrolidinones, piperidinones, oxazolidinones, isoxazolidinones, thiazolidinones, isothiazolidinones, and succinimides.

Illustrative releasable linkers include ketals, acetals, hemiaminals, and aminals formed from methylene, 1-alkoxyalkylene, 1-alkoxycycloalkylene, 1-alkoxyalkylenecarbonyl, and 1-alkoxycycloalkylenecarbonyl radicals, esters and amides formed from carbonylarylcarbonyl, carbonyl(carboxyaryl)carbonyl, carbonyl(biscarboxyaryl)carbonyl, and haloalkylenecarbonyl radicals, oxysilanes and aminosilanes formed from alkylene(dialkylsilyl), alkylene(alkylarylsilyl), alkylene(diarylsilyl), (dialkylsilyl)aryl, (alkylarylsilyl)aryl, and (diarylsilyl)aryl radicals, oxycarbonyloxy, oxycarbonyloxyalkyl, sulfonyloxy, oxysulfonylalkyl, iminoalkylidenyl, carbonylalkylideniminyl, iminocycloalkylidenyl, carbonylcycloalkylideniminyl, alkylenethio, alkylenearylthio, and carbonylalkylthio radicals, each of which is optionally substituted.

Further illustrative releasable linkers include hydrazones, acylhydrazones orthoformates, and carbamoyl derivatives.

Further illustrative releasable linkers include disulfides and activated thioethers.

In any of the embodiments described herein, the releasable linker may include oxygen bonded to methylene, 1-alkoxyalkylene, 1-alkoxycycloalkylene, 1-alkoxyalkylenecarbonyl, and 1-alkoxycycloalkylenecarbonyl to form an acetal or ketal, wherein each of the fragments is optionally substituted with a substituent $X^2$, as defined herein. Alternatively, the methylene or alkylene is substituted with an optionally-substituted aryl.

In any of the embodiments described herein, the releasable linker may include nitrogen bonded to methylene, 1-alkoxyalkylene, 1-alkoxycycloalkylene, 1-alkoxyalkylenecarbonyl, and 1-alkoxycycloalkylenecarbonyl to form a hemiaminal ether or aminal, wherein each of the fragments is optionally substituted with a substituent $X^2$, as defined herein. Alternatively, the methylene or alkylene is substituted with an optionally-substituted aryl.

In any of the embodiments described herein, the releasable linker may include oxygen bonded to sulfonylalkyl to form an alkylsulfonate.

In any of the embodiments described herein, the releasable linker may include nitrogen bonded to iminoalkylidenyl, carbonylalkylideniminyl, iminocycloalkylidenyl, and carbonylcycloalkylideniminyl to form an hydrazone, each of which is optionally substituted with a substituent $X^2$, as defined herein. In an alternate configuration, the hydrazone may be acylated with a carboxylic acid derivative, an orthoformate derivative, or a carbamoyl derivative to form releasable linkers containing various acylhydrazones.

In any of the embodiments described herein, the releasable linker may include oxygen bonded to alkylene(dialkylsilyl), alkylene(alkylarylsilyl), alkylene(diarylsilyl), (alkylarylsilyl)aryl, and (diarylsilyl)aryl to form a silanol, each of which is optionally substituted with a substituent $X^2$, as defined herein.

In any of the embodiments described herein, the releasable linker may include nitrogen bonded to carbonylarylcarbonyl, carbonyl(carboxyaryl)carbonyl, carbonyl(biscarboxyaryl)carbonyl to form an amide, or alternatively an amide with a drug nitrogen.

In any of the embodiments described herein, the releasable linker may include oxygen bonded to carbonylarylcarbonyl, carbonyl(carboxyaryl)carbonyl, carbonyl(biscarboxyaryl)carbonyl to form an ester, or alternatively an ester with drug oxygen.

It is to be understood that the bivalent spacer linkers may be combined in any chemically relevant way, either directly or via an intervening heteroatom to construct the releasable linkers described herein. It is further understood that the nature of the arrangement of spacer and heteroatom linkers defines where the releasable linker will cleave in vivo. For example, two spacer linkers that terminate in a sulfur atom when combined form a disulfide, which is the cleavable bond in the releasable linker formed thereby.

For example, in another embodiment, the polyvalent linker comprises a 3-thiosuccinimid-1-ylalkyloxymethyloxy moiety, where the methyl is optionally substituted with alkyl or substituted aryl.

In another embodiment, the polyvalent linker comprises a 3-thiosuccinimid-1-ylalkylcarbonyl, where the carbonyl forms an acylaziridine with the drug.

In another embodiment, the polyvalent linker comprises a 1-alkoxycycloalkylenoxy moiety.

In another embodiment, the polyvalent linker comprises an alkyleneaminocarbonyl(dicarboxylarylene)carboxylate.

In another embodiment, the polyvalent linker comprises a dithioalkylcarbonylhydrazide, where the hydrazide forms an hydrazone with the drug.

In another embodiment, the polyvalent linker comprises a 3-thiosuccinimid-1-ylalkylcarbonylhydrazide, where the hydrazide forms a hydrazone with the drug.

In another embodiment, the polyvalent linker comprises a 3-thioalkylsulfonylalkyl(disubstituted silyl)oxy, where the disubstituted silyl is substituted with alkyl or optionally substituted aryl.

In another embodiment, the polyvalent linker comprises a plurality of spacer linkers selected from the group consisting of the naturally occurring amino acids and stereoisomers thereof.

In another embodiment, the polyvalent linker comprises a 2-dithioalkyloxycarbonyl, where the carbonyl forms a carbonate with the drug.

In another embodiment, the polyvalent linker comprises a 2-dithioarylalkyloxycarbonyl, where the carbonyl forms a carbonate with the drug and the aryl is optionally substituted.

In another embodiment, the polyvalent linker comprises a 2-dithioarylalkyloxycarbonyl, where the carbonyl forms a carbonate with the drug, and the aryl is optionally substituted.

In another embodiment, the polyvalent linker comprises a 3-thiosuccinimid-1-ylalkyloxyalkyloxyalkylidene, where the alkylidene forms an hydrazone with the drug, each alkyl is independently selected, and the oxyalkyloxy is optionally substituted with alkyl or optionally substituted aryl.

In another embodiment, the polyvalent linker comprises a 2-dithioalkyloxycarbonylhydrazide.

In another embodiment, the polyvalent linker comprises a 2- or 3-dithioalkylamino, where the amino forms a vinylogous amide with the drug.

In another embodiment, the polyvalent linker comprises a 2-dithioalkylamino, where the amino forms a vinylogous amide with the drug, and the alkyl is ethyl.

In another embodiment, the polyvalent linker comprises a 2- or 3-dithioalkylaminocarbonyl, where the carbonyl forms a carbamate with the drug.

In another embodiment, the polyvalent linker comprises a 2-dithioalkylaminocarbonyl, where the carbonyl forms a carbamate with the drug. In another aspect, the alkyl is ethyl.

In another embodiment, the polyvalent linker comprises a 2-dithioalkyloxycarbonyl, where the carbonyl forms a carbamate with the drug. In another aspect, the alkyl is ethyl.

In another embodiment, the polyvalent linker comprises a 2-dithioarylalkyloxycarbonyl, where the carbonyl forms a carbamate or a carbamoylaziridine with the drug.

In another embodiment, the polyvalent linker comprises a 4-dithioarylalkyloxycarbonyl, where the carbonyl forms a carbamate or a carbamoylaziridine with the drug.

In another embodiment, the polyvalent linkers described herein comprise divalent radicals of the formulae

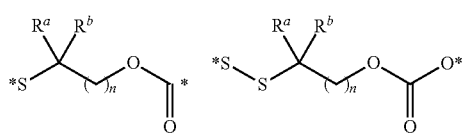

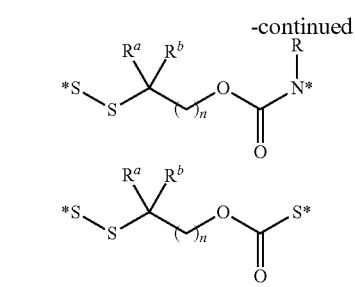

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates points of attachment for the drug, vitamin, imaging agent, diagnostic agent, other bivalent linkers, or other parts of the conjugate.

In another embodiment, the polyvalent linkers described herein comprise divalent radicals of the formulae

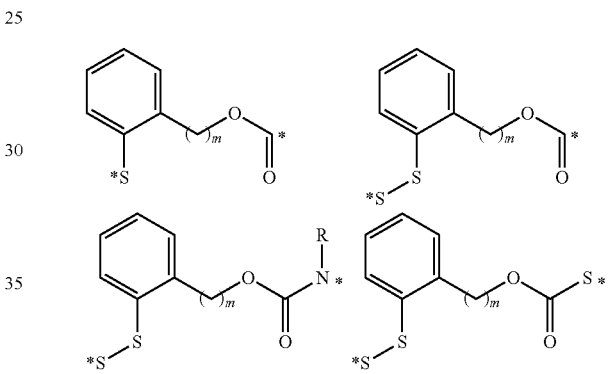

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other bivalent linkers, or other parts of the conjugate.

In another embodiment, the polyvalent linkers described herein comprise divalent radicals of the formulae

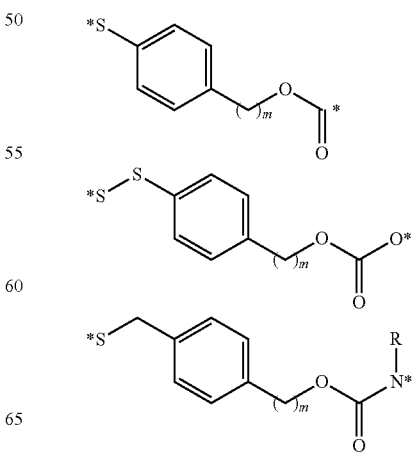

-continued

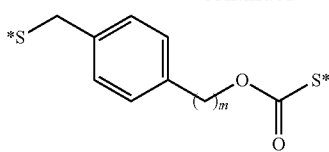

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other divalent linkers, or other parts of the conjugate.

In another embodiment, the compounds described herein comprise one or more radicals linkers of selected from the formulae:

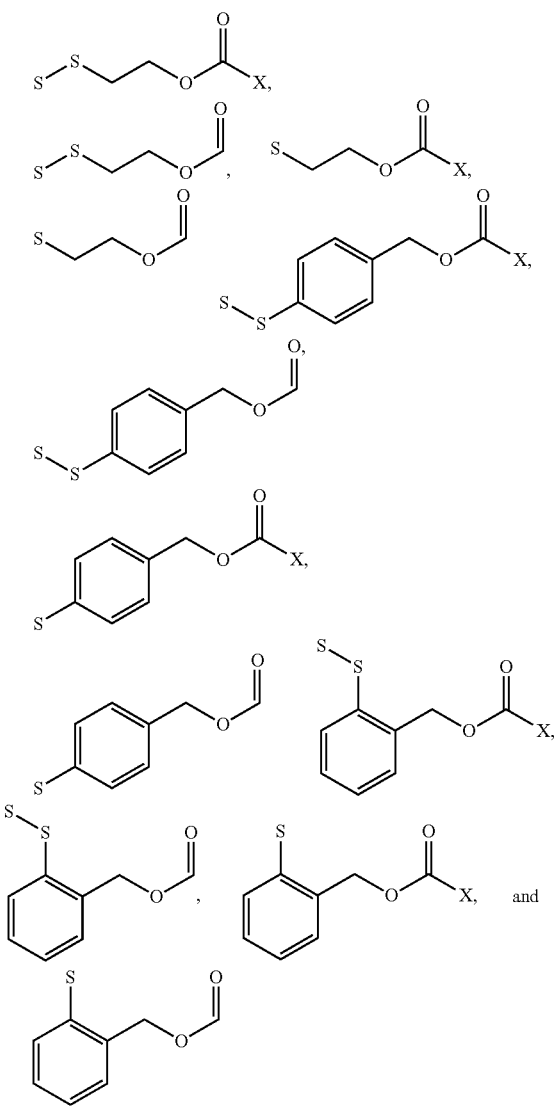

wherein X is NH, O, or S.

In another embodiment, the polyvalent linkers herein described comprise a radical having the formula:

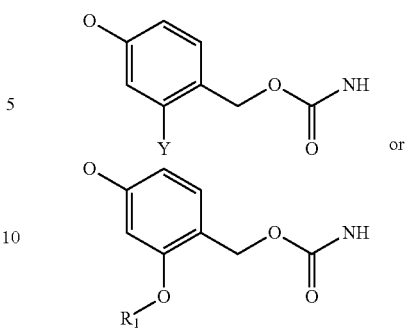

or

Another embodiment, the polyvalent linkers described herein comprise a radical of having the formula:

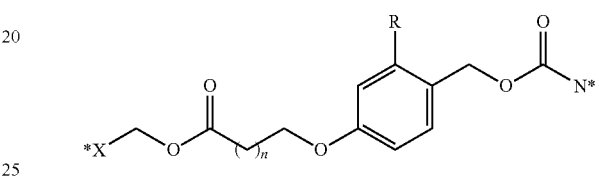

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and the symbol (*) indicates points of attachment. It is appreciated that other substituents may be present on the aryl ring, the benzyl carbon, the alkanoic acid, or the methylene bridge, including but not limited to hydroxy, alkyl, alkoxy, alkylthio, halo, and the like.

In another embodiment, the polyvalent linkers described herein comprise radicals selected from carbonyl, thionocarbonyl, alkylene, cycloalkylene, alkylenecycloalkyl, alkylenecarbonyl, cycloalkylenecarbonyl, carbonylalkylcarbonyl, 1 alkylenesuccinimid-3-yl, 1 (carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl) succinimid-3-yl, and 1-(carbonyltetrahydrofuranyl)succinimid-3-yl, wherein each of said spacer linkers is optionally substituted with one or more substituents $X^1$;

wherein each substituent is independently selected from the group consisting of alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from the group consisting of an amino acid, an amino acid derivative, and a peptide, and wherein $R^6$ and $R^7$ are each independently selected from the group consisting of an amino acid, an amino acid derivative, and a peptide.

It is to be understood that the compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

In each of the foregoing and each of the following embodiments, it is also to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to be a description of such hydrates and/or solvates, including pharmaceutically acceptable solvates.

In each of the foregoing and each of the following embodiments, it is also to be understood that the formulae include and represent each possible isomer, such as stereoisomers and geometric isomers, both individually and in any and all possible mixtures. In each of the foregoing and each of the following embodiments, it is also to be understood that the formulae include and represent any and all crystalline forms, partially crystalline forms, and non crystalline and/or amorphous forms, and co-crystals of the compounds.

In another embodiment, the compounds described herein can be internalized into the targeted pathogenic cells by binding to PSMA. In particular, PSMA selectively and/or specifically binds the conjugate, and internalization can occur, for example, through PSMA-mediated endocytosis. Once internalized, conjugates containing a releasable linker can complete delivery of the drug to the interior of the target cell. Without being bound by theory, it is believed herein that in those cases where the drug is toxic to normal cells or tissues, such a delivery system can decrease toxicity against those non-target cells and tissues because the releasable linker remains substantially or completely intact until the compounds described herein are delivered to the target cells. Accordingly, the compounds described herein act intracellularly by delivering the drug to an intracellular biochemical process, which in turn decreases the amount of unconjugated drug exposure to the host animal's healthy cells and tissues.

The conjugates described herein can be used for both human clinical medicine and veterinary applications. Thus, the host animal harboring the population of pathogenic cells and treated with the compounds described herein can be human or, in the case of veterinary applications, can be a laboratory, agricultural, domestic, or wild animal. The present invention can be applied to host animals including, but not limited to, humans, laboratory animals such as rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The drug delivery conjugate compounds described herein can be administered in a combination therapy with any other known drug whether or not the additional drug is targeted. Illustrative additional drugs include, but are not limited to, peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins, antigens and antibodies thereto, haptens and antibodies thereto, hormones, lipids, phospholipids, liposomes, toxins, antibiotics, analgesics, bronchodilators, beta-blockers, antimicrobial agents, antihypertensive agents, cardiovascular agents including antiarrhythmics, cardiac glycosides, antianginals, vasodilators, central nervous system agents including stimulants, psychotropics, antimanics, and depressants, antiviral agents, antihistamines, cancer drugs including chemotherapeutic agents, tranquilizers, anti-depressants, H-2 antagonists, anticonvulsants, antinauseants, prostaglandins and prostaglandin analogs, muscle relaxants, anti-inflammatory substances, stimulants, decongestants, antiemetics, diuretics, antispasmodics, antiasthmatics, anti-Parkinson agents, expectorants, cough suppressants, mucolytics, and mineral and nutritional additives.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$, and $C_2$-$C_{24}$, $C_2$-$C_{12}$, $C_2$-$C_8$, $C_2$-$C_6$, and the like. Illustratively, such particularly limited length alkyl groups, including $C_1$-$C_8$, $C_1$-$C_6$, and $C_1$-$C_4$, and $C_2$-$C_8$, $C_2$-$C_6$, and $C_2$-$C_4$, and the like may be referred to as lower alkyl. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$, and $C_3$-$C_{24}$, $C_3$-$C_{12}$, $C_3$-$C_8$, $C_3$-$C_6$, and $C_3$-$C_4$, and the like. Illustratively, such particularly limited length alkenyl and/or alkynyl groups, including $C_2$-$C_8$, $C_2$-$C_6$, and $C_2$-$C_4$, and $C_3$-$C_8$, $C_3$-$C_6$, and $C_3$-$C_4$, and the like may be referred to as lower alkenyl and/or alkynyl. It is appreciated herein that shorter alkenyl, and/or alkynyl groups may add less lipophilicity to the compound and accordingly will have different pharmacokinetic behavior. In embodiments of the invention described herein, it is to be understood, in each case, that the recitation of alkyl refers to alkyl as defined herein, and optionally lower alkyl. In embodiments of the invention described herein, it is to be understood, in each case, that the recitation of alkenyl refers to alkenyl as defined herein, and optionally lower alkenyl. In embodiments of the invention described herein, it is to be understood, in each case, that the recitation of alkynyl refers to alkynyl as defined herein, and optionally lower alkynyl. Illustrative alkyl, alkenyl, and alkynyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like, and the corresponding groups containing one or more double and/or triple bonds, or a combination thereof.

As used herein, the term "alkylene" includes a divalent chain of carbon atoms, which is optionally branched. As used herein, the term "alkenylene" and "alkynylene" includes a divalent chain of carbon atoms, which is optionally branched, and includes at least one double bond or triple bond, respectively. It is to be understood that alkynylene may also include one or more double bonds. It is to be further understood that in certain embodiments, alkylene is advantageously of limited length, including $C_1$-$C_{24}$, $C_1$-$C_{12}$, $C_1$-$C_6$, and $C_1$-$C_4$, and $C_2$-$C_{24}$, $C_2$-$C_{12}$, $C_2$-$C_8$, $C_2$-$C_6$, and $C_2$-$C_4$, and the like. Illustratively, such particularly limited length alkylene groups, including $C_1$-$C_8$, $C_1$-$C_6$, and $C_1$-$C_4$, and $C_2$-$C_8$, $C_2$-$C_6$, and $C_2$-$C_4$, and the like may be referred to as lower alkylene. It is to be further understood that in certain embodiments alkenylene and/or alkynylene may each be advantageously of limited length, including $C_2$-$C_{24}$, $C_2$-$C_{12}$, $C_2$-$C_6$, and $C_2$-$C_4$, and $C_3$-$C_{24}$, $C_3$-$C_{12}$, $C_3$-$C_8$, $C_3$-$C_6$, and $C_3$-$C_4$, and the like. Illustratively, such particularly limited length alkenylene and/or alkynylene groups, including $C_2$-$C_8$, $C_2$-$C_6$, and $C_2$-$C_4$, and $C_3$-$C_8$, $C_3$-$C_6$, and $C_3$-$C_4$, and the like may be referred to as lower alkenylene and/or alkynylene. It is appreciated herein that shorter alkylene, alkenylene, and/or alkynylene groups may add less lipophilicity to the compound and accordingly will have different pharmacokinetic behavior. In embodiments of the invention described herein, it is to be understood, in each case, that the recitation of alkylene, alkenylene, and alkynylene refers to alkylene, alkenylene, and alkynylene as defined herein, and optionally lower alkylene, alkenylene, and alkynylene. Illustrative alkyl groups are, but not limited to, methylene, ethylene, n-propylene, isopropylene, n-butylene, isobutylene, sec-butylene, pentylene, 1,2-pentylene, 1,3-pentylene, hexylene, heptylene, octylene, and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "amino acid" refers generally to beta, gamma, and longer amino acids, such as amino acids of the formula:

where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornithine, threonine, and the like.

As used herein, the term "amino acid derivative" generally refers to an amino acid as defined herein where either, or both, the amino group and/or the side chain is substituted. Illustrative amino acid derivatives include prodrugs and protecting groups of the amino group and/or the side chain, such as amine, amide, hydroxy, carboxylic acid, and thio prodrugs and protecting groups. Additional Illustrative amino acid derivatives include substituted variations of the amino acid as described herein, such as, but not limited to, ethers and esters of hydroxy groups, amides, carbamates, and ureas of amino groups, esters, amides, and cyano derivatives of carboxylic acid groups, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylic acid and derivatives thereof" includes the group $CO_2H$ and salts thereof, and esters and amides thereof, and CN.

As used herein, the term "sulfinic acid or a derivative thereof" includes $SO_2H$ and salts thereof, and esters and amides thereof.

As used herein, the term "sulfonic acid or a derivative thereof" includes $SO_3H$ and salts thereof, and esters and amides thereof.

As used herein, the term "sulfonyl" includes alkylsulfonyl, alkenylsulfonyl, alkynylsulfonyl, heteroalkylsulfonyl, heteroalkenylsulfonyl, heteroalkynylsulfonyl, cycloalkylsulfonyl, cycloalkenylsulfonyl, cycloheteroalkylsulfonyl, cycloheteroalkenylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, acylsulfonyl, and the like, each of which is optionally substituted.

As used herein, the term "phosphinic acid or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

As used herein, the term "phosphonic acid or a derivative thereof" includes $PO_3H_2$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH heteroaryloxylNH heteroarylalkyloxylNH heteroarylalkenyloxylNH heteroarylalkynyloxylNH acyloxy, and the like, each of which is optionally substituted.

As used herein, the term "hydrazino and derivatives thereof" includes alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, heteroarylNHNH, heteroarylalkylNHNH, heteroarylalkenylNHNH, heteroarylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is also optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, haloalkyl, heteroalkyl, arylalkyl, arylheteroalkyl, heteroaryl, heteroarylalkyl, heteroarylheteroalkyl, and/or sulfonic acid is optionally substituted.

Illustrative substituents include, but are not limited to, a radical $-(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from $-CO_2R^4$ and $-CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

As used herein, the term "leaving group" refers to a reactive functional group that generates an electrophilic site on the atom to which it is attached such that nucleophiles may be added to the electrophilic site on the atom. Illustrative leaving groups include, but are not limited to, halogens, optionally substituted phenols, acyloxy groups, sulfonoxy groups, and the like. It is to be understood that such leaving groups may be on alkyl, acyl, and the like. Such leaving groups may also be referred to herein as activating groups, such as when the leaving group is present on acyl. In addition, conventional peptide, amide, and ester coupling agents, such as but not limited to PyBop, BOP-Cl, BOP, pentafluorophenol, isobutylchloroformate, and the like, form various intermediates that include a leaving group, as defined herein, on a carbonyl group.

As used herein the term "radical" with reference to, for example, the PSMA binding or targeting ligand, and/or the independently selected drug, refers to a PSMA binding or targeting ligand, and/or an independently selected drug, as described herein, where one or more atoms or groups, such as a hydrogen atom, or an alkyl group on a heteroatom, and the like, is removed to provide a radical for conjugation to the polyvalent linker L.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, (C$_3$-C$_{20}$)alkanoyl; halo-(C$_3$-C$_{20}$)alkanoyl; (C$_3$-C$_{20}$)alkenoyl; (C$_4$-C$_7$)cycloalkanoyl; (C$_3$-C$_6$)-cycloalkyl(C$_2$-C$_{10}$)alkanoyl; optionally substituted aroyl, such as unsubstituted aroyl or aroyl substituted by 1 to 3 substituents selected from the group consisting of halogen, cyano, trifluoromethanesulphonyloxy, (C$_1$-C$_3$)alkyl and (C$_1$-C$_3$)alkoxy, each of which is optionally further substituted with one or more of 1 to 3 halogen atoms; optionally substituted aryl(C$_2$-C$_{16}$)alkanoyl and optionally substituted heteroaryl(C$_2$-C$_{16}$)alkanoyl, such as the aryl or heteroaryl radical being unsubstituted or substituted by 1 to 3 substituents selected from the group consisting of halogen, (C$_1$-C$_3$)alkyl and (C$_1$-C$_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, (C$_1$-C$_3$)alkyl, and (C$_1$-C$_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

It is to be understood that in every instance disclosed herein, the recitation of a range of integers for any variable describes the recited range, every individual member in the range, and every possible subrange for that variable. For example, the recitation that n is an integer from 0 to 8, describes that range, the individual and selectable values of 0, 1, 2, 3, 4, 5, 6, 7, and 8, such as n is 0, or n is 1, or n is 2, etc. In addition, the recitation that n is an integer from 0 to 8 also describes each and every subrange, each of which may for the basis of a further embodiment, such as n is an integer from 1 to 8, from 1 to 7, from 1 to 6, from 2 to 8, from 2 to 7, from 1 to 3, from 2 to 4, etc.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. In addition, it is to be understood that the compositions may be prepared from various co-crystals of the compounds described herein.

Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

In addition to the illustrative dosages and dosing protocols described herein, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and/or vehicles.

Illustrative formats for oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration.

Illustratively, administering includes local use, such as when administered locally to the site of disease, injury, or defect, or to a particular organ or tissue system. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

Depending upon the disease as described herein, the route of administration and/or whether the compounds and/or compositions are administered locally or systemically, a wide range of permissible dosages are contemplated herein, including doses falling in the range from about 1 µg/kg to about 1 g/kg. The dosages may be single or divided, and may administered according to a wide variety of protocols, including q.d., b.i.d, t.i.d., or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

The effective use of the compounds, compositions, and methods described herein for treating or ameliorating diseases caused by pathogenic cells expressing PSMA may be based upon animal models, such as murine, canine, porcine, and non-human primate animal models of disease. For example, it is understood that prostate cancer in humans may be characterized by a loss of function, and/or the development of symptoms, each of which may be elicited in animals, such as mice, and other surrogate test animals. In particular the mouse models described herein where cancer cells, such as LNCaP cells are subcutaneously implanted may be used to evaluate the compounds, the methods of treatment, and the pharmaceutical compositions described herein to determine the therapeutically effective amounts described herein.

The compounds, linkers, intermediates, and conjugates described herein may be prepared using conventional processes, including those described in International Patent Publication Nos. WO 2009/002993, WO 2004/069159, WO 2007/022494, and WO 2006/012527, and U.S. patent application Ser. No. 13/837,539 (filed Mar. 15, 2013). The disclosures of each of the foregoing are herein incorporated by reference in their entirety.

Each of the publications cited herein is incorporated herein by reference.

The following examples further illustrate specific embodiments of the invention; however, the following illustrative examples should not be interpreted in any way to limit the invention.

EXAMPLES

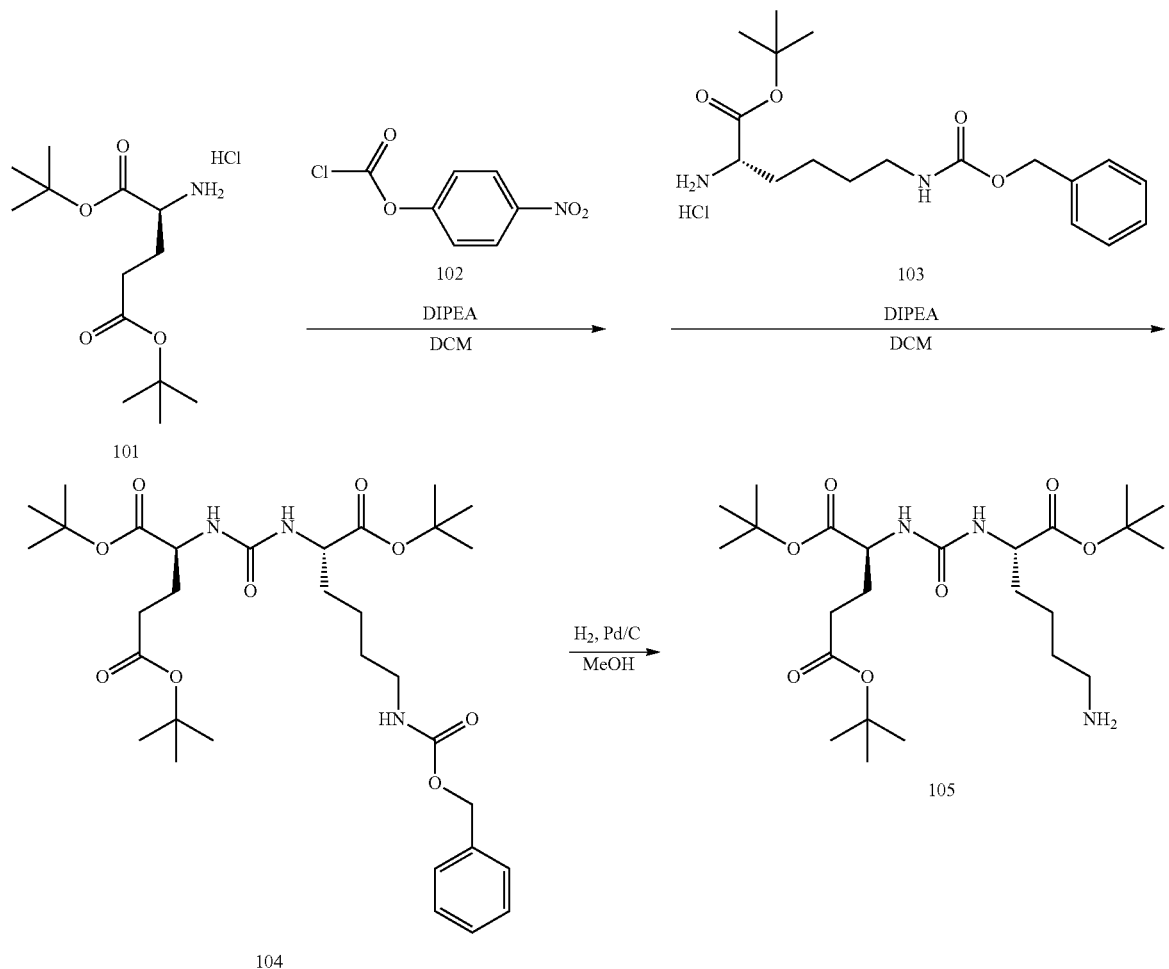

Example. Compound 104. In a 250 mL round-bottom flask, H-Glu(OtBu)-OtBu.HCl (1) (4.83 g, 16.3 mmol) and 4-nitrophenyl chloroformate, (102) (3.47 g, 17.2 mmol) were dissolved in dichloromethane (50 mL) and stirred in an ice bath under argon. Diisopropylethylamine (6.28 mL, 36.1 mmol) was added slowly, dropwise and the reaction mixture was stirred in the ice bath for 5 min, then warmed to room temperature and stirred for 30 min. H-Lys(Z)-OtBu HCl (103) (7.01 g, 18.8 mmol) was added portionwise, followed by dropwise addition of diisopropylethylamine (6.54 mL, 37.5 mmol), and stirred at room temperature for 1 hr. The reaction mixture was concentrated under reduced pressure, then purified by silica gel chromatography in 10-100% ethyl acetate/petroleum ether to yield 104 (8.76 g, 86%, ESI m/z=622.54 [M+H]$^+$).

Example. Compound 105. 104 (8.76 g, 14.1 mmol) was dissolved in anhydrous methanol (100 mL) and added slowly along the walls of the 250 mL round-bottom flask containing palladium on carbon, 10 wt. % (100 mg). A balloon containing hydrogen gas was attached to the flask using a three-way stopcock adapter, and the atmosphere of the flask was evacuated under reduced pressure, then replaced with hydrogen gas (3×), then stirred at room temperature under hydrogen gas for 1 hr. To the reaction mixture was added dry, untreated celite (~20 g) and stirred for 5 min. The reaction mixture was filtered and concentrated under reduced pressure to yield 105 (6.86 g, quantitative, ESI m/z=488.46 [M+H]$^+$).

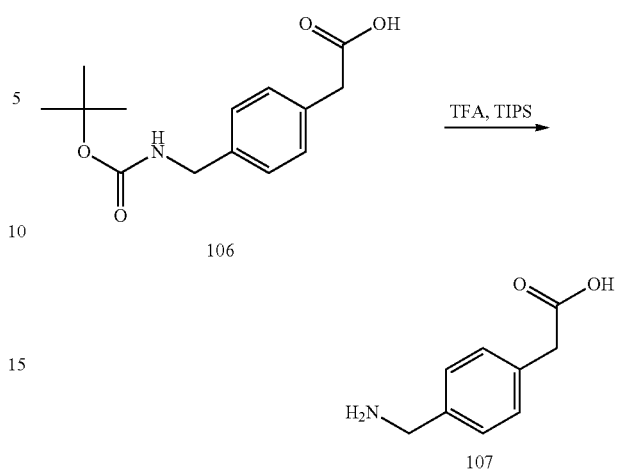

Example. Compound 107. Boc-4-aminomethylphenylacetic acid (106) (2.00 g, 7.5 mmol) dissolved in a solution of trifluoroacetic acid (9.75 mL) and triisopropylsilane (0.25 mL) and stirred at room temperature for 30 min, then concentrated under reduced pressure and coevaporated with dichloromethane (3×), then placed under vacuum, to yield 4-aminomethylphenylacetic acid (107) (quantitative).

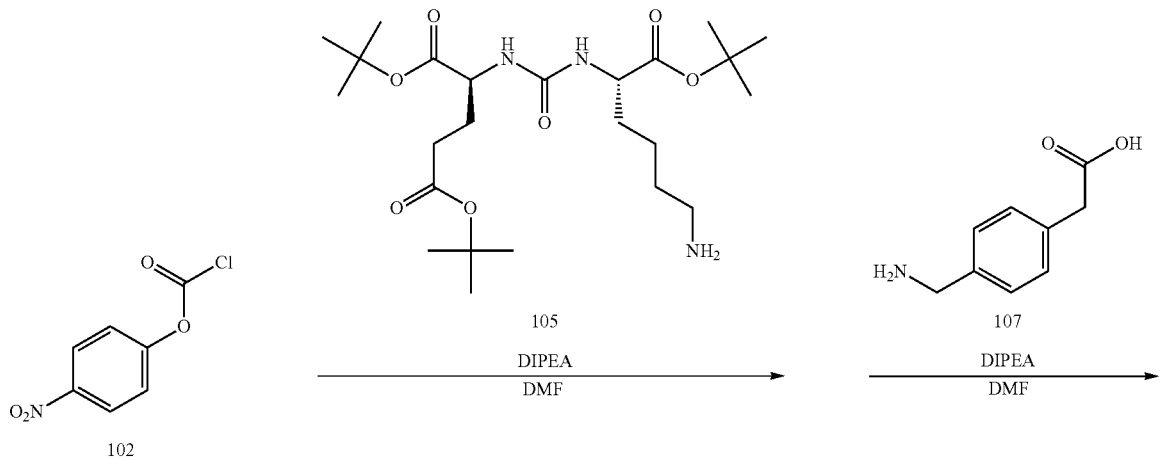

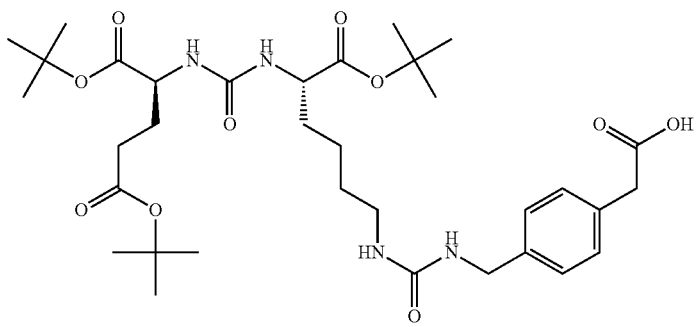

Example. Compound 108. To a stirring solution of 4-nitrophenyl chloroformate (102) (1.01 g, 5.0 mmol) in dry dimethylformamide (10 mL) was added slowly dropwise a solution of 105 (2.45 g, 5.0 mmol) and diisopropylethylamine (0.88 mL, 5.0 mmol) in dry dimethylformamide (10 mL), and the reaction mixture was stirred at room temperature for 30 min under argon. The reaction mixture was cooled in an ice bath and a suspension of 7 (~1.25 g, ~7.5 mmol) and diisopropylethylamine (1.76 mL, 10.1 mmol) in dry dimethylformamide (10 mL) was added slowly dropwise to the reaction vessel, then the reaction mixture was warmed to room temperature and stirred for 30 min under argon. The reaction mixture was purified by preparative HPLC in 10-100% acetonitrile/0.1% formic acid to yield 8 (0.56 g, 16%, $^1$H NMR consistent with structure of 108; ESI m/z=679.50 [M+H]$^+$).

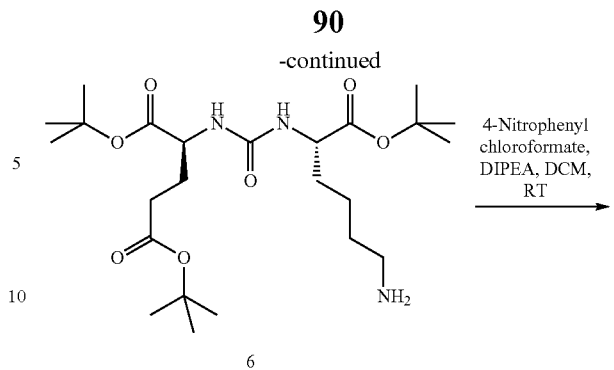

Example. Preparation of protected ligand 7, including coupling group.

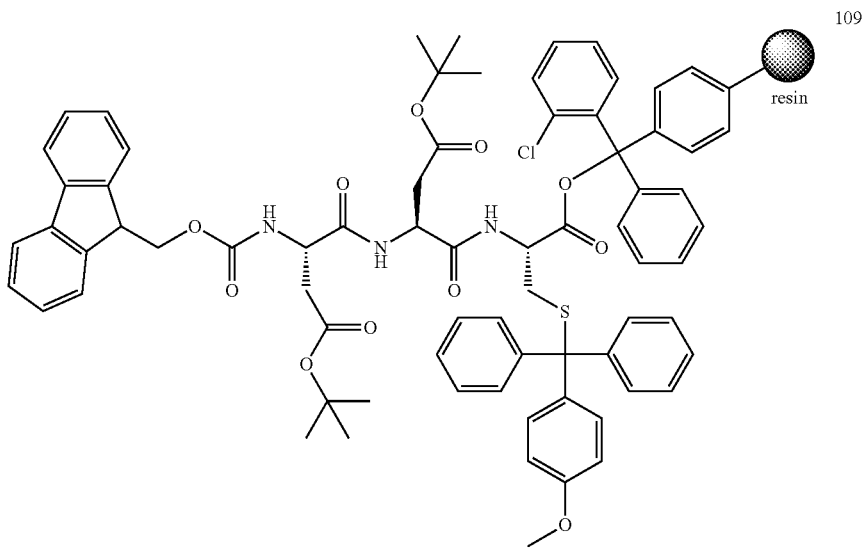 [SMILES: COc1ccc(C(SC[C@H](NC(=O)[C@H](CC(=O)OC(C)(C)C)NC(=O)[C@H](CC(=O)OC(C)(C)C)NC(=O)OCC2c3ccccc3-c3ccccc32)C(=O)OC(c2ccccc2)(c2ccc(C)cc2)c2ccccc2Cl)(c2ccccc2)c2ccccc2)cc1]

109

Example. Peptide 109.

TABLE 1

Reagents for peptide 109 synthesis

| Reagent | mmol | Equiv-alents | Molecular weight (g/mol) | quantity |
|---|---|---|---|---|
| H-Cys(4-methoxytrityl)-2-chlorotrityl-Resin | 0.87 | 1.0 | | |
| Fmoc-Asp(OtBu)—OH | 2 × 1.74 | 2 × 2.0 | 411.5 | 716 mg |
| PyBOP | 2 × 1.73 | 2 × 2.0 | 520.39 | 900 mg |
| diisopropylethylamine | 2 × 3.48 | 2 × 4.0 | 129.25 (d = 0.742 g/mL) | 606 μL |

In a peptide synthesis vessel H-Cys(4-methoxytrityl)-2-chlorotrityl-resin (0.87 mmol) was loaded and washed with isopropyl alcohol (3×10 mL) followed by dimethylformamide (3×10 mL). To the vessel was then introduced Fmoc-Asp(OtBu)—OH (2.0 equiv) in dimethylformamide, diisopropylethylamine (4.0 equiv), and PyBOP (2.0 equiv). Argon was bubbled for 1 hr, the coupling solution was drained, and the resin was washed with dimethylformamide (3×10 mL) and isopropyl alcohol (3×10 mL). Kaiser tests were performed to assess reaction completion. Fmoc deprotection was carried out using 20% piperidine in dimethylformamide (3×10 mL) before each amino acid coupling. The above sequence was repeated to complete 2 coupling steps. The resin was dried under argon for 30 min.

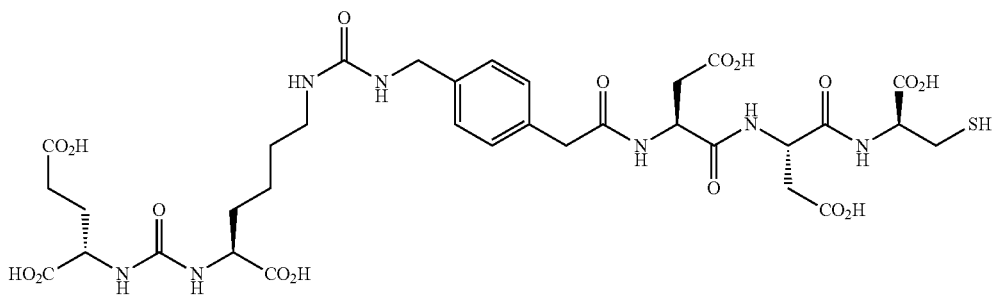

110

Example. Peptide 110.

TABLE 2

Reagents for peptide 110 synthesis

| Reagent | mmol | Equivalents | Molecular weight (g/mol) | quantity |
|---|---|---|---|---|
| Fmoc-Asp(OtBu)-Asp(OtBu)-Cys(Mmt)-2-ClTrt-resin | 0.18 | 1.0 | | |
| 108 | 0.22 | 1.2 | 678.81 | 150 mg |
| PyBOP | 0.37 | 2.0 | 520.39 | 191 mg |
| diisopropylethylamine | 0.74 | 4.0 | 129.25 (d = 0.742 g/mL) | 128 μL |

In a peptide synthesis vessel 109 (0.18 mmol) was loaded and washed with isopropyl alcohol (3×10 mL) followed by dimethylformamide (3×1.0 mL). Fmoc deprotection was carried out using 20% piperidine in dimethylformamide (3×10 mL). Kaiser tests were performed to assess reaction completion. To the vessel was then introduced 108 (1.2 equiv) in dimethylformamide, diisopropylethylamine (4.0 equiv), and PyBOP (2.0 equiv). Argon was bubbled for 1 hr, the coupling solution was drained, and the resin was washed with dimethylformamide (3×10 mL) and isopropyl alcohol (3×10 mL). Kaiser tests were performed to assess reaction completion. Peptide was cleaved from the resin using a cleavage mixture consisting of dithiothreitol (114 mg, 0.74 mmol) dissolved in a solution of trifluoroacetic acid (19 mL), $H_2O$ (0.5 mL), triisopropylsilane (0.5 mL). One-third of the cleavage mixture was introduced and argon was bubbled for 30 min. The cleavage mixture was drained into a clean flask. The resin was bubbled 2 more times with more cleavage mixture, for 30 min each, and drained into a clean flask. The drained cleavage mixture was then concentrated and purified by preparative HPLC in 0-30% acetonitrile/ 0.1% formic acid to yield 110 (66.9 mg, 43%, $^1$H NMR consistent with structure of 110; ESI m/z=844.57 [M+H]$^+$).

Example. Similarly, the following compounds are prepared as described herein:

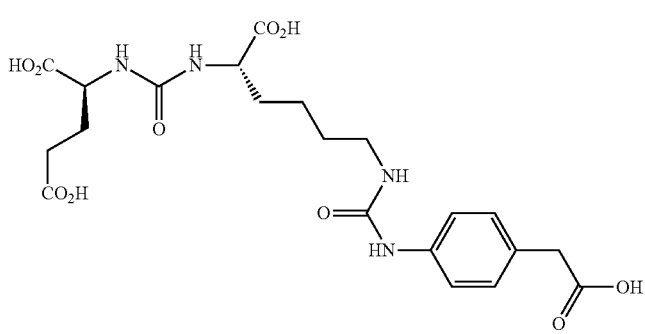

EC1080

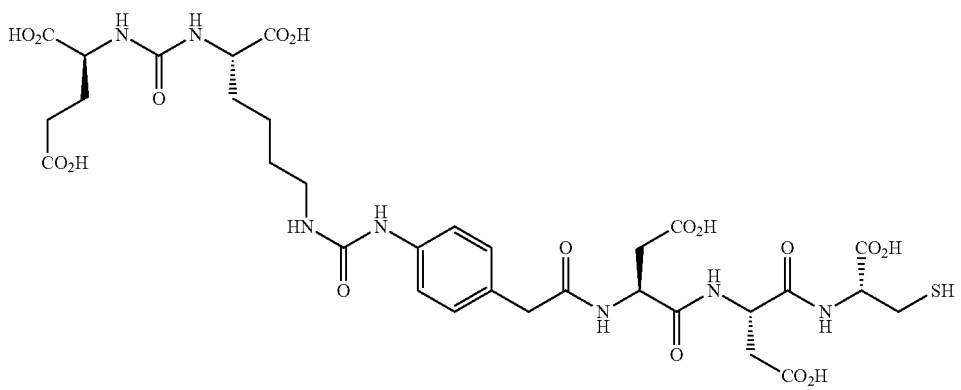

EC1067

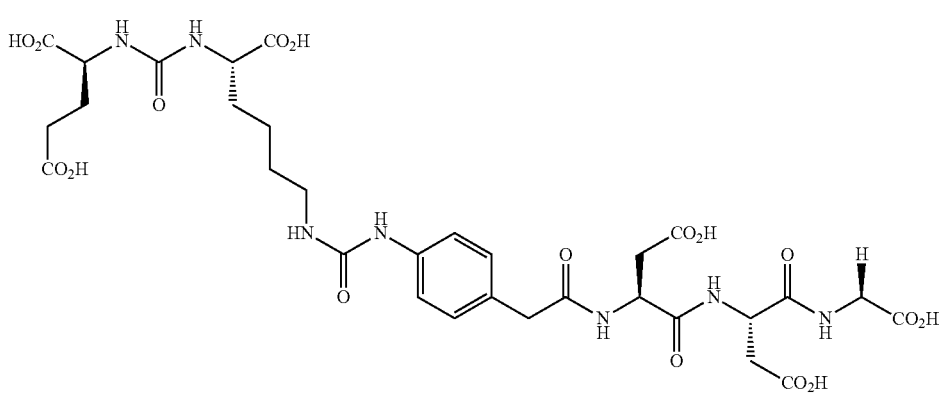

EC1100

EC1167
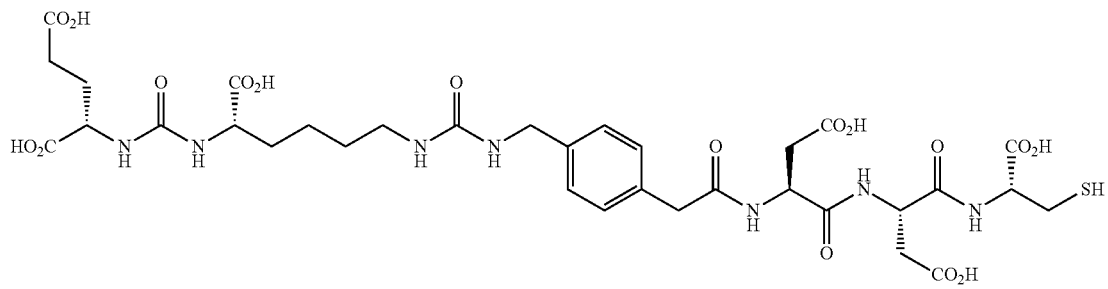
EC1168
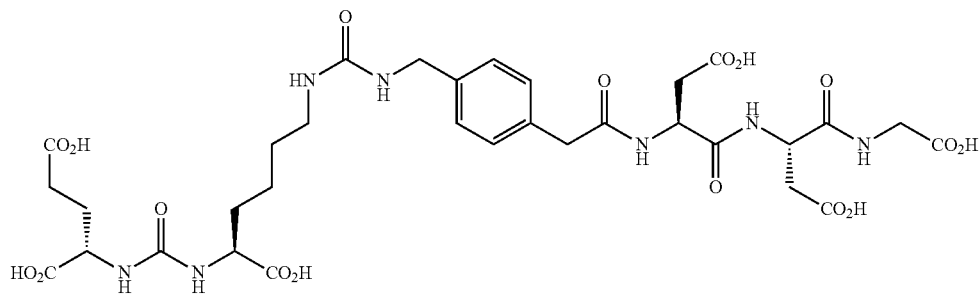
(Exact Mass: 797.27; Mol. Wt.: 797.72)
EC1170
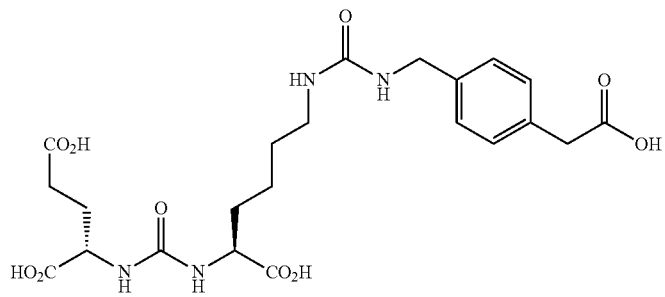
(Exact Mass: 510.20; Mol. Wt.: 510.49)
EC1302
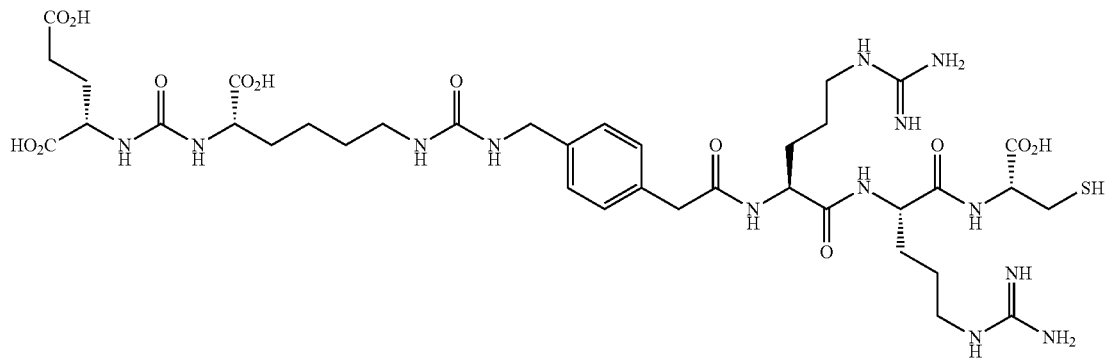

-continued
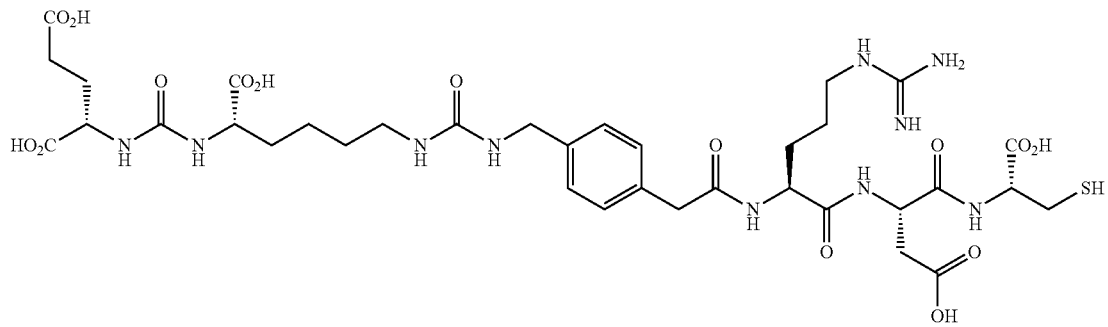
EC1303
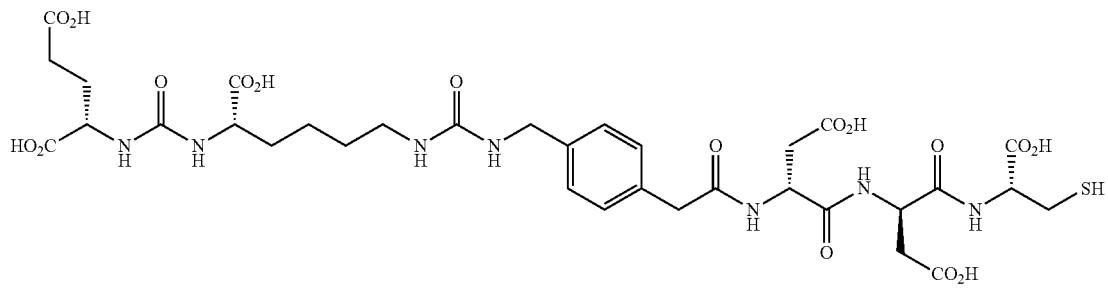
EC1307
D-Asp-D-Asp
110 +
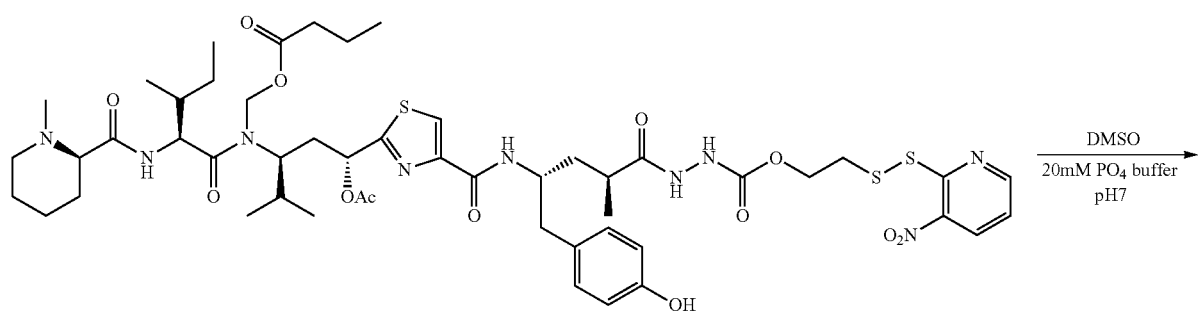
16
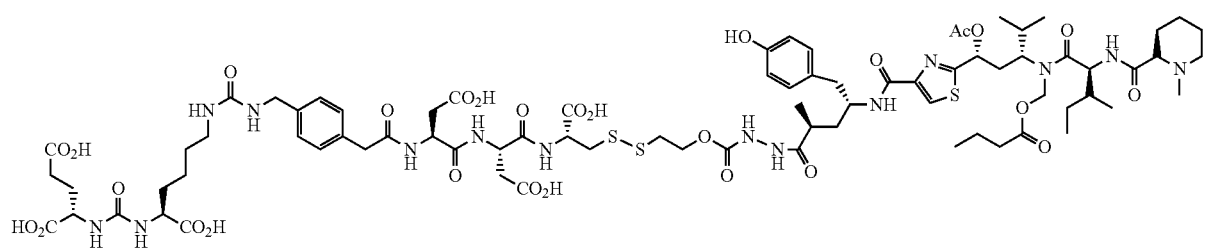
EC1169
(compound 112)

Example. EC1169 (Compound 112). In a 25 mL round bottom flask, 16 (47 mg, 0.04 mmol) was dissolved in dimethylsulfoxide (2 mL). A solution of 110 (36 mg, 0.04 mmol) in 20 mM pH7 sodium phosphate buffer (2 mL) was added dropwise, stirring at room temperature with Argon bubbling for 30 min. The reaction mixture was purified by preparative HPLC (10-100% acetonitrile/50 mM NH$_4$HCO$_3$ pH7) to yield 112 (56.6 mg, 74%, $^1$H NMR consistent with structure of EC1169; ESI m/z=895.58 [M+2H]$^{2+}$).

Example. Synthesis of 3-nitro-2-disulfenylethanol 2.

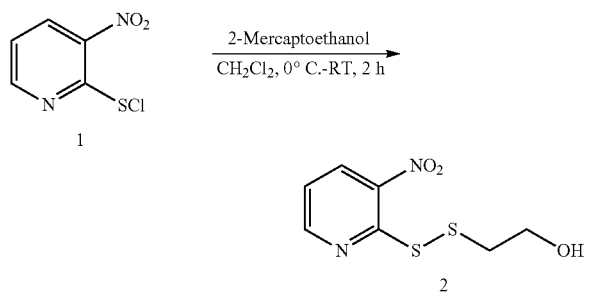

A three-necked 500 mL flask was dried and argon purged, then fitted with an addition funnel. 3-Nitro-2-sulfenyl chloride pyridine 1 (5.44 g, 27.11 mmol, 1.4 equiv) was added to the flask and dissolved in 200 mL of CH$_2$Cl$_2$. The solution was cooled to 0° C. Mercaptoethanol (1.33 mL, 18.98 mmol) was diluted with 50 mL of CH$_2$Cl$_2$ and placed in the addition funnel. The 2-mercaptoethanol solution was then added drop-wise slowly over the course of 15 minutes. The reaction progress was monitored by TLC (Rf 0.4 in 5% CH$_3$OH/CH$_2$Cl$_2$). Solvent was removed under reduced pressure and dried. The crude product was purified over silica gel (5% CH$_3$OH/CH$_2$Cl$_2$). The fractions were collected and solvent was removed by evaporating on a rotary evaporator and dried. 3.4 g of 3-nitro-2-disulfenylethanol 2 was obtained (77% yield).

Example. Synthesis of 4-nitrophenyl-(3'-nitropyridin-2'-yl)disulfenylethyl carbonate 3.

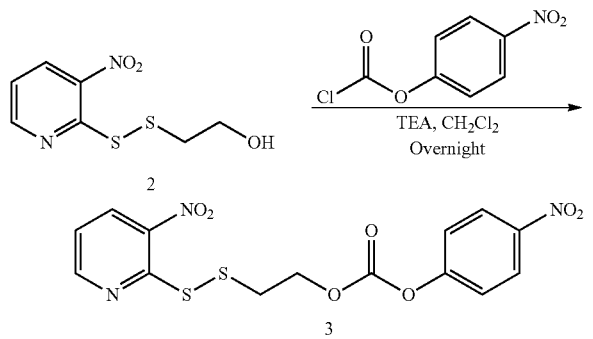

A 250 L Round-Bottomed Flask was dried and argon purged. 3-Nitro-2-disulfenylethanol 2 (3.413 g, 14.69 mmol) was added and dissolved in 45 mL of CH$_2$Cl$_2$. 4-Nitrophenylchloroformate (3.663 g, 17.63 mmol, 1.2 equiv) was added, along with triethylamine (2.9 mL, 20.57 mmol, 1.4 equiv), and the mixture stirred under argon overnight. The mixture was concentrated under reduced pressure and dried. The residue was purified by silica (30% EtOAc/petroleum ether) and the fractions were collected, solvent was removed under reduced pressure, and dried. 2.7 g of 4-nitrophenyl-(3'-nitropyridin-2'-yl)disulfenylethyl carbonate 3 was obtained (47% yield).

Example. Synthesis of 2-(Boc-tubutyrosine (Tut))hydrazinecarboxylic acid (3'nitropyridyl-2'-yl)disulfanylethyl ester 6.

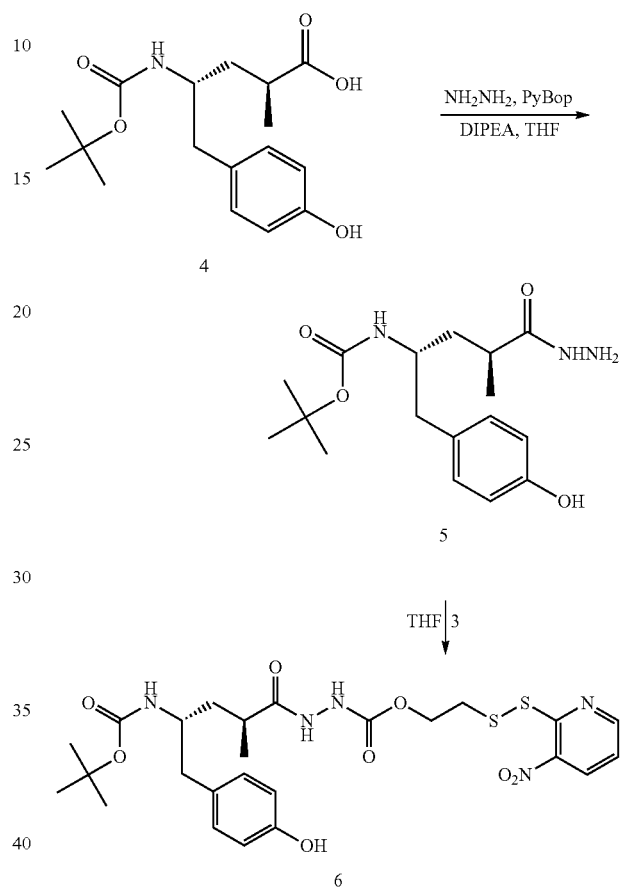

10.67 g (33 mmol) of Boc-Tut-acid 4 was dissolved in 100 mL anhydrous THF, 17.24 g (33 mmol) of PyBop, and 17.50 mL (99 mmol, 3.0 equiv) of DIPEA were added. The reaction mixture stirred for few minutes, 1.0 mL (31.68 mmol, 0.96 equiv) of hydrazine was added and stirred for 15 minutes. LC-MS analysis (X-Bridge shield RP18, 3.5 □m column; gradient 10% to 100% acetonitrile in 6 min, pH 7.4 buffer) confirmed the hydrazide 5 formation, 14.47 g (36.3 mmol, 1.1 equiv) of 4-nitrophenyl-(3'-nitropyridin-2'-yl)disulfenylethyl carbonate 2 was added. The resulting clear solution was stirred at room temperature for 24 hours. LC-MS analysis (X-Bridge shield RP18, 3.5 □m column; gradient 30% to 100% acetonitrile in 9 min, pH 7.4 buffer) indicated >98% conversion. The reaction mixture was diluted with EtOAc (~1.0 L), washed with sat. NH$_4$Cl (400 mL), sat NaHCO$_3$ solution (3×300 mL), and brine (300 mL). The organic layer was dried over Na$_2$SO$_4$ (100 g), and concentrated under reduced pressure. The crude product was loaded onto a Teledyne Redisep Gold Silica Column and eluted with MeOH/CH$_2$Cl$_2$ (330 g column; 0 to 10% gradient) using a CombiFlash chromatography system. The fractions were collected and solvent was removed under reduced pressure and dried. 16.10 g of 2-(Boc-Tut)hydrazinecarboxylic acid (3'nitropyridyl-2'-yl)disulfanylethyl ester 6 was obtained (82% yield).

Example. Synthesis of azido methylbutyrate dipeptide 9.

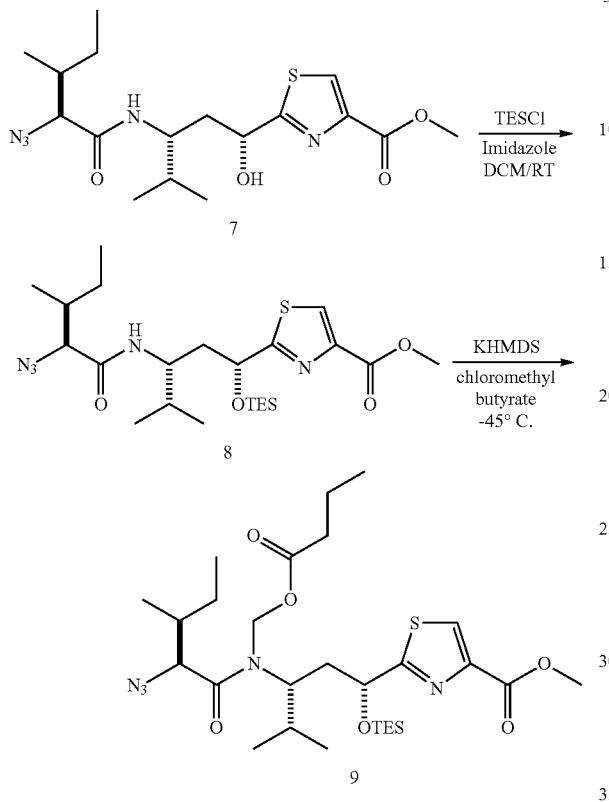

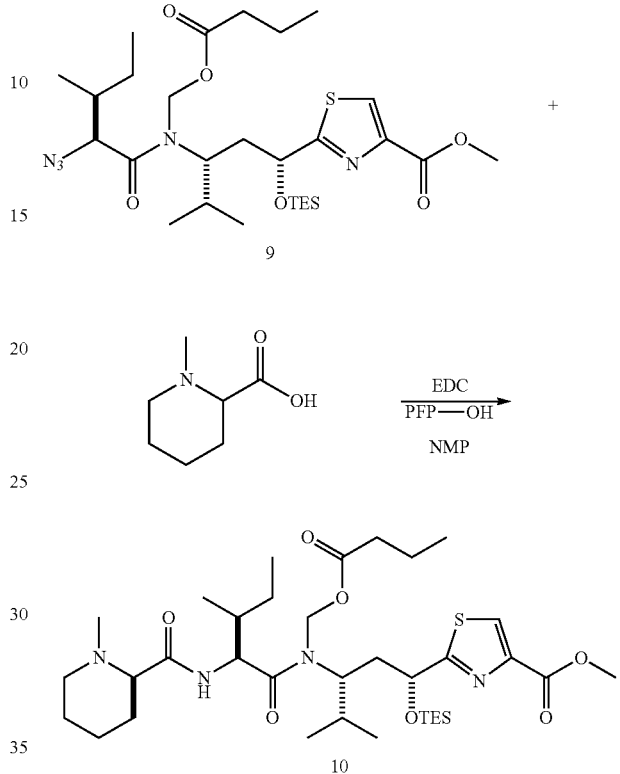

Dipeptide 7 (10.83 g, 27.25 mmol) was dissolved in 100 mL dichloromethane and imidazole (2.05 g, 1.1 eq.) was added. The reaction mixture was stirred at room temperature to dissolve all solids and cooled in the ice bath for 10 min. TESCl (4.8 mL, 1.05 equiv.) was added drop-wise at 0° C. stirred under argon, and warmed to room temperature over 1.5 h. TLC (3:1 hexanes/EtOAc) showed complete conversion. The reaction was filtered to remove the imidazole HCl salt. 125 mL dichloromethane was added to the filtrate, and the resulting solution was extracted with 250 mL brine. The brine layer was extracted with 125 mL dichloromethane. The combined organic phase was washed with 250 mL brine, separated, dried over 45.2 g of $Na_2SO_4$, and filtered. The resulting solution was concentrated under reduced pressure, co-evaporated with toluene (2×5 mL) and dried over high-vacuum overnight to give 14.96 g of crude product 8.

The crude product 8 was used without further purification. TES protected dipeptide was dissolved in 100 mL THF (anhydrous, inhibitor-free), cooled to −45° C., and stirred at −4.5° C. for 15 minutes before adding KHMDS (0.5 M in toluene, 61 mL, 1.05 equiv.), drop-wise. After the addition of KHMDS was finished, the reaction was stirred at −45° C. for 20 minutes, and chloromethyl butyrate (4.4 mL, 1.1 equiv.) was added. The reaction mixture was stirred at −45° C. for another 20 minutes. The reaction was quenched with 25 mL, MeOH and warmed to room temperature. 250 mL EtOAc and 250 mL brine were added to the reaction mixture, and the organic phase was separated. The solvent was evaporated to reduce the volume of solution. The solution was passed through 76.5 g silica in a 350 mL sintered glass funnel. The silica plug was washed with 500 mL EtOAc/petroleum ether (1:4). The filtrate and the wash were concentrated to oily residue and dried under high vacuum to give 16.5 g product 9 as a light yellow wax.

Example. Synthesis of tripeptide methyl ester 10.

Based on 16.5 g of alkylated dipeptide 9 (26.97 mmol.), N-methyl pipecolinate (MEP) (5.51 g, 1.4 equiv.) and pentafluorophenol (7.63 g, 1.5 equiv.) were added to a 300 mL hydrogenation flask. NMP (115 mL) was then added, followed by EDC (7.78 g, 1.5 equiv.). The mixture was stirred at room temperature for overnight. 16.5 g of alkylated dipeptide 9 was dissolved in 16.5 mL NMP, transferred the solution into the hydrogenation flask, washed the residual 9 with 8 mL NMP, and transferred into the hydrogenation flask. Dry 10% Pd/C (1.45, 0.05 eq.) was added. The reaction mixture was vacuumed/backfilled with hydrogen 3 times, and the flask was shaken under hydrogen (~35 psi) for 3.5 hours. The reaction mixture was analyzed by HPLC. The reaction mixture was filtered through 40 g of celite in a 350 mL sintered glass funnel and washed with 250 mL of EtOAc. The filtrate and the wash were transferred to a separatory funnel and washed with a 1% $NaHCO_3$/10% NaCl solution (200 mL×3). The organic layer was isolated and dried over 45.2 g of $Na_2SO_4$. The solution was filtered and rotovaped under reduced pressure. A sticky amber residue was obtained and dried under high vacuum overnight to give 19.3 g of crude product. The crude product was dissolved in 10 mL of dichloromethane, split into two portions, and purified with a 330 g Teledyne Redisep Silica Gold column. The combined fractions of two purifications were evaporated and dried under high vacuum to give 7.64 g of 10 as a pale yellow solid (overall yield: 39% over 3 steps from compound 7).

Example. Synthesis of tripeptide acid 11.

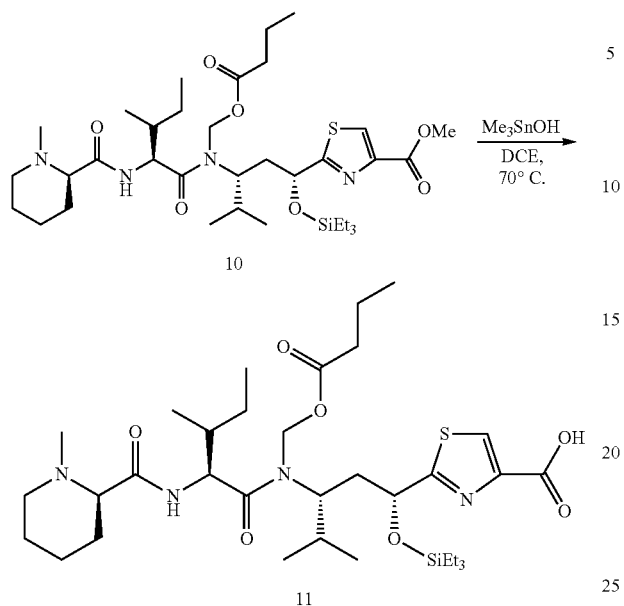

Methyl ester 10 (6.9 g, 9.7 mmol) was dissolved in 1,2-dichloroethane (1.93 mL) and added to a round bottomed flask, equipped with a stir bar and condenser. To this solution was added trimethyltin hydroxide (24.6 g, 14 eq.). The mixture was heated at 70° C. for 5 hours. LC-MS analysis indicated that the desired product had been formed and <15% of starting methyl ester 10 remained. The reaction was cooled in an ice bath for 30 minutes. The resulting precipitate was then removed by filtration. The filtrate was stared overnight at −20° C. The filtrate was then divided into two portions and each was subjected the chromatography procedure which follows.

Each portion was concentrated under reduced pressure and then placed under high vacuum for 30 min. The concentrate was then immediately dissolved in acetonitrile (95 mL). To this solution was then added an ammonium bicarbonate solution (95 mL; 50 mM, pH=7). This solution was loaded onto a Biotage SNAP C18 reverse phase cartridge (400 g, KP-C18-HS) and eluted with 50 mM ammonium bicarbonate and acetonitrile (1:1 to 100% ACN) using a Biotage chromatography system. Fractions were analyzed by LC-MS. Pure fractions were combined and ACN was removed under reduced pressure. The resulting aqueous suspension was extracted with EtOAc (3×). The combined organic layers were washed with brine, dried over anhydrous Na$_2$SO$_4$, and concentrated under reduced pressure. Purification of the two portions resulted in the recovery of clean 11 (4.6 g, 65%).

Example. Synthesis of acetyl tripeptide acid 13.

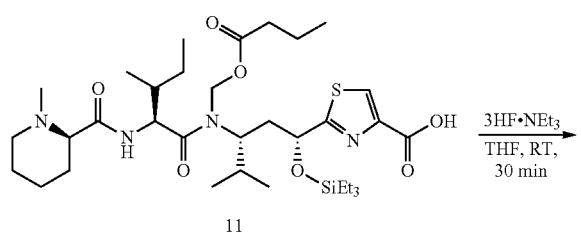

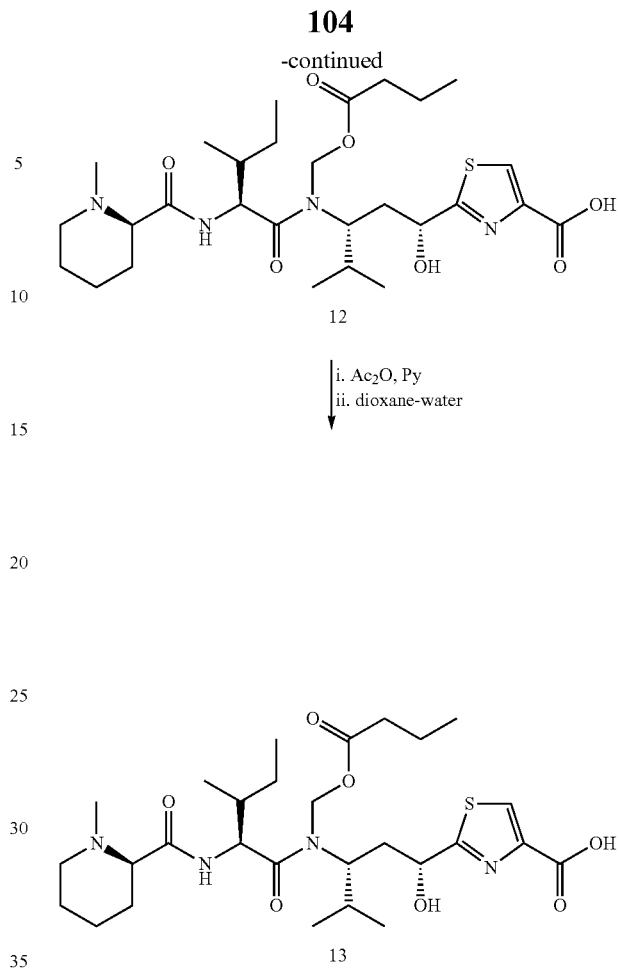

In a round bottomed flask, tripeptide acid 11 (3.9 g, 5.6 mmol) was dissolved in anhydrous THF (23 mL). To this solution was added 3 HF.TEA complex (1.8 mL, 2 eq.). The reaction was stirred at room temperature for 1 hour. LC-MS analysis indicated complete conversion to the desired des-TES product 12. The solvent was removed under reduced pressure and the residue was placed on the high vacuum for 40 minutes. The resulting residue was then dissolved in pyridine (26 mL), and acetic anhydride (7.9 mL, 15 eq.) and DMAP (25 mg) were added. The reaction was stirred at room temperature for 1 hour. LC-MS analysis indicated complete conversion to the desired acetyl tripeptide acid 13. To the reaction mixture was then added a 1:1 solution of 1,4-dioxane/water (150 mL). The reaction was stirred for 1 hour at which point the solvents were removed under high vacuum rotovap. To the residue was added toluene and the solvent was removed under vacuum (80 mL, 3×). The resulting crude 13 was dried under high vacuum overnight. The crude material was then dissolved in ACN (72 mL). Sodium phosphate buffer (50 mM, pH=7.8, 288 mL) was then added, and the pH of the resulting suspension was adjusted to neutral using saturated sodium bicarbonate solution. This solution was loaded onto a Biotage SNAP C18 reverse phase cartridge (400 g, KP-C18-HS) and eluted with water and acetonitrile (20% ACN to 65% ACN) using a Biotage chromatography system. Fractions were analyzed by LC-MS. Clean fractions were combined, the ACN was removed, and the aqueous solution was placed on the freeze dryer, resulting in purified acetyl tripeptide 13 (2.5 g, 71%).

Example. Synthesis of 2-(tubulysin B)hydrazinecarboxylic acid (3'nitropyridyl-2'-yl)disulfanylethyl ester 16.

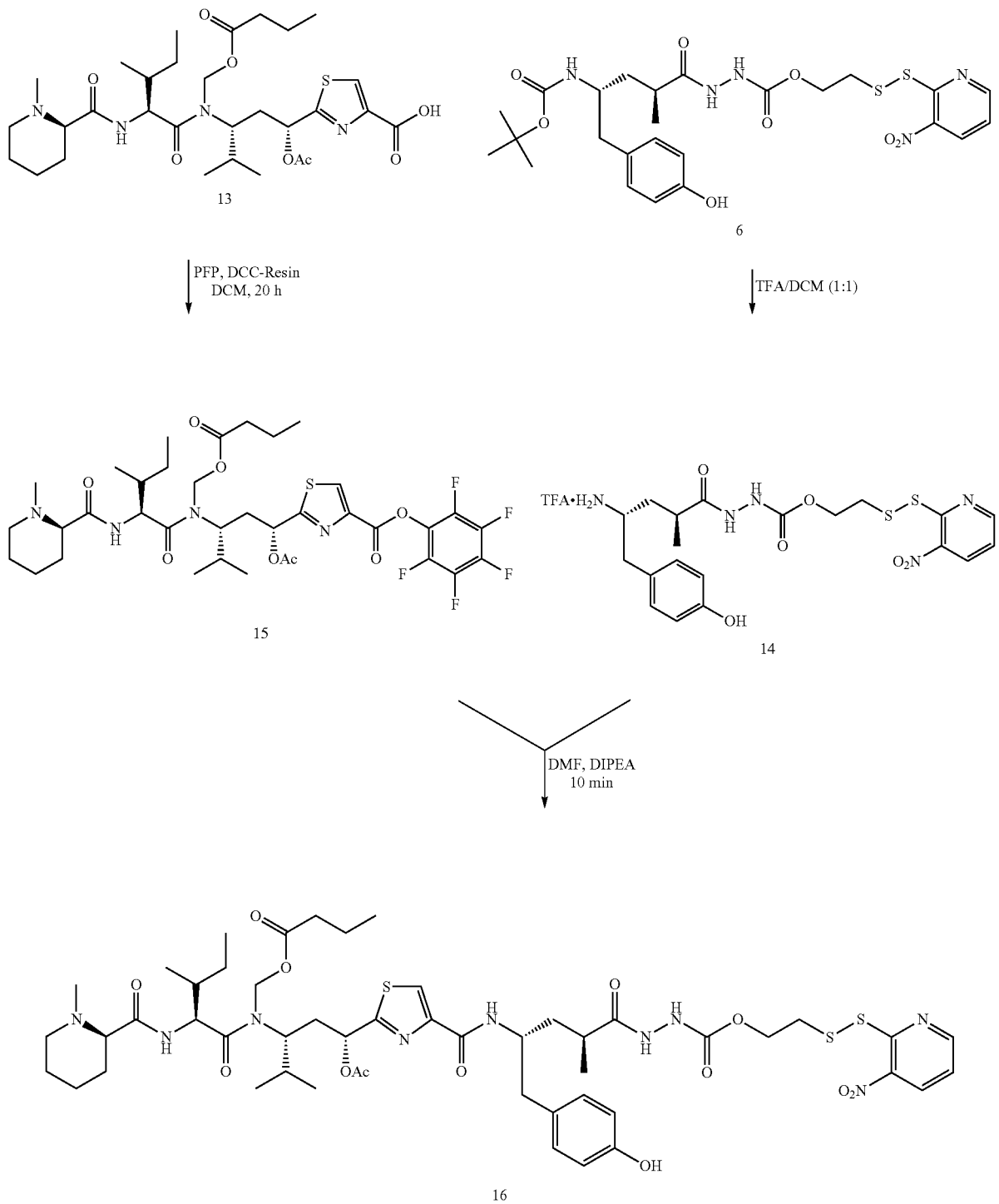

The activated Boc-Tut-fragment 6 (2.63 g, 4.42 mmol, 1.1 equiv) was treated with TFA/CH$_2$Cl$_2$ (42 mL; 1:1) and stirred for 30 minutes. LC-MS analysis (X-Bridge shield RP18, 3.5 μm column; gradient 10% to 100% acetonitrile in 6 min, pH 7.4 buffer) confirmed the product formation. TFA was removed under reduced pressure, co-evaporated with CH$_2$Cl$_2$ (3×30 mL) and activated Tut-derivative 14 was dried under high vacuum for 18 h. In another flask, the tripeptide acid 13 (2.51 g, 4.02 mmol) was dissolved in 70 mL CH$_2$Cl$_2$ (anhydrous) and 1.48 g (8.04 mmol, 2.0 equiv) of pentafluorophenol in 5 min of CH$_2$Cl$_2$ was added, followed by 8.74 g (20.1 mmol, 5.0 equiv) of DCC-resin. The resulting reaction mixture was stirred at room temperature for 20 hours. LC-MS analysis (X-Bridge shield RP1.8, 3.5 μm column; gradient 10% to 100% acetonitrile in 6 min, pH 7.4 buffer) indicated >99% conversion. The DCC-resin was filtered off, the CH$_2$Cl$_2$ was removed under reduced pressure, and the pentafluorophenol activated product 1.5 was dried under high vacuum for 10 minutes. The residue was dissolved in 16.7 mL DMF, and DIPEA (12.6 mL, 72.36 mmol, 18.0 equiv) was added. Tut-fragment trifluoroacetic acid salt 14 in DMF (8.5 mL) was added slowly over 5 min. The resulting clear solution was stirred at room temperature for 1 h. LC-MS analysis (X-Bridge shield RP18, 3.5 μm column; gradient 10% to 100% acetonitrile in 6 min, pH 7.4 buffer) confirmed the product formation. The reaction mixture was diluted with EtOAc (700 mL), washed with brine (300 mL, 2×100 mL), dried over Na$_2$SO$_4$ (75 g), concentrated, and dried for 15 hours. The crude product was dissolved in CH$_2$Cl$_2$ (25 mL) and loaded onto a Teledyne Redisep Gold Silica Column and eluted with MeOH/CH$_2$Cl$_2$ (330 g column: 0 to 5% gradient) using Combiflash chromatographic system. The fractions were collected and solvent was removed by evaporating on a rotary evaporator and dried. 3.91 g of 2-(tubulysin B)hydrazinecarboxylic acid (3'nitropyridyl-2'-yl)disulfanylethyl ester 16 was obtained (89% yield).

Example. Preparation of 2-(tubulysin B)hydrazinecarboxylic acid (pyrid-2-yl)disulfanylethyl ester 3.

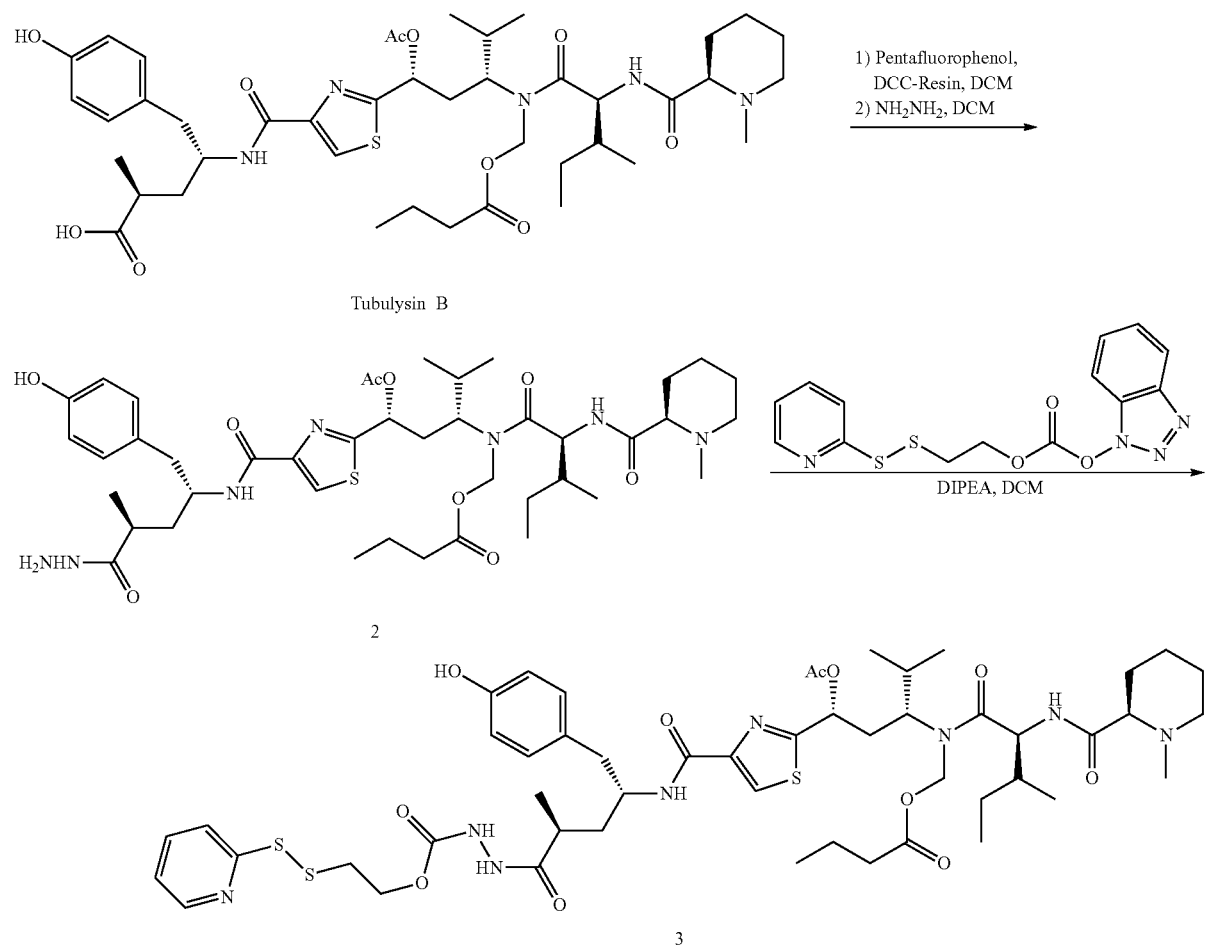

Example. Similarly, the following compounds are prepared as described herein:

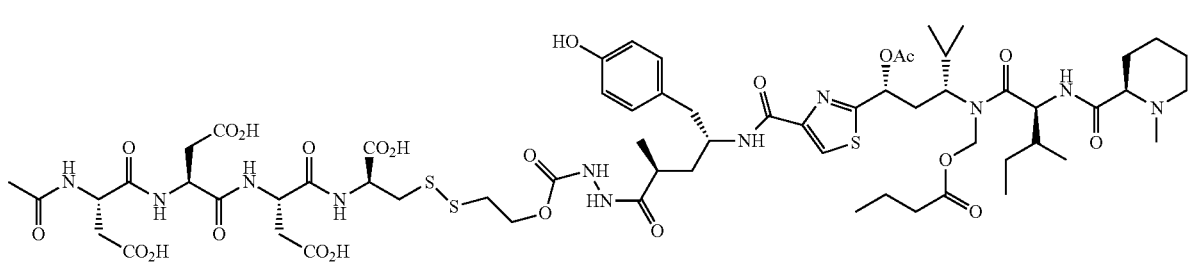

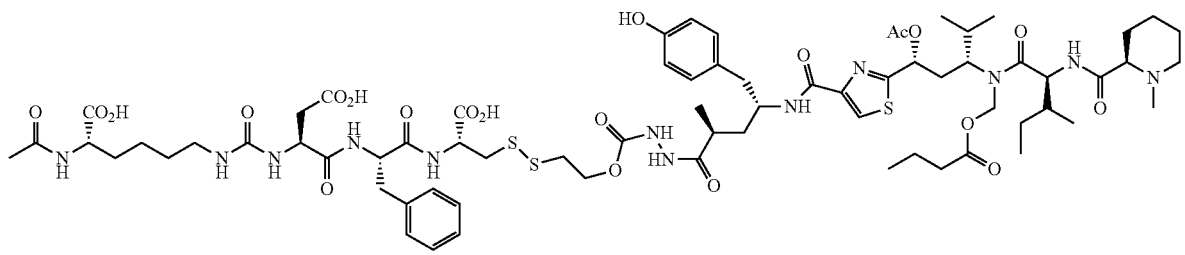

EC1568

Example. Additional tubulysins described herein may be isolated from natural sources, including but not limited to bacteria and other fermentations. Alternatively, the tubulysins described herein may be prepared according to conventional processes, including but not limited to the processes described in PCT International Publication Nos. WO 2009/055562, WO 2012/019123, and WO 2013/149185, and co-pending U.S. application Ser. No. 13/841,078 the disclosures of each of which are incorporated herein by reference in their entirety.

Example. Alternative Preparation of EC1169 (compound 12).

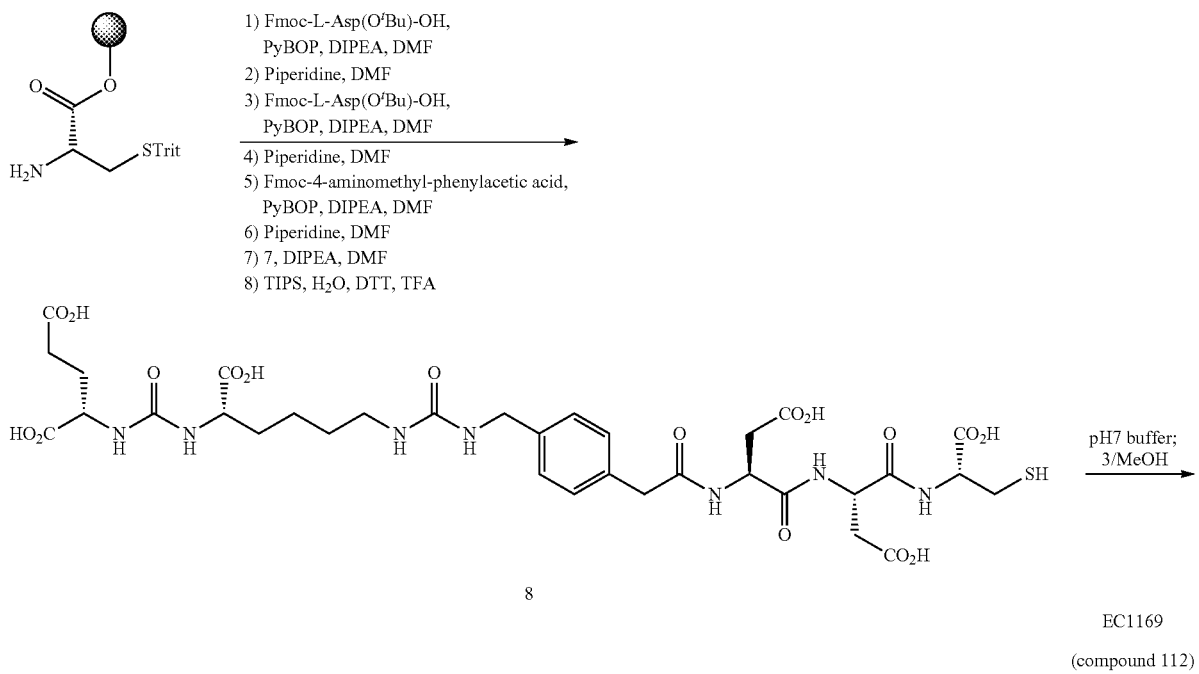

EC1169
(compound 112)

Example. The following representative example compounds are described to better illustrate the invention described herein and may be prepared according to the synthetic methods described for the above examples, and/or using conventional processes.

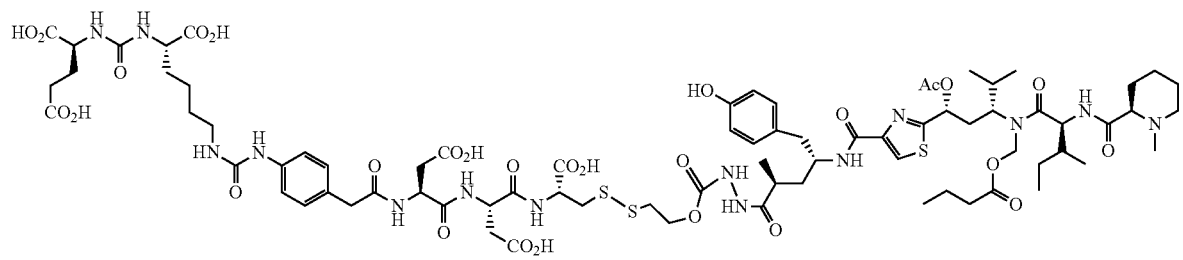

EC1069

EC1183
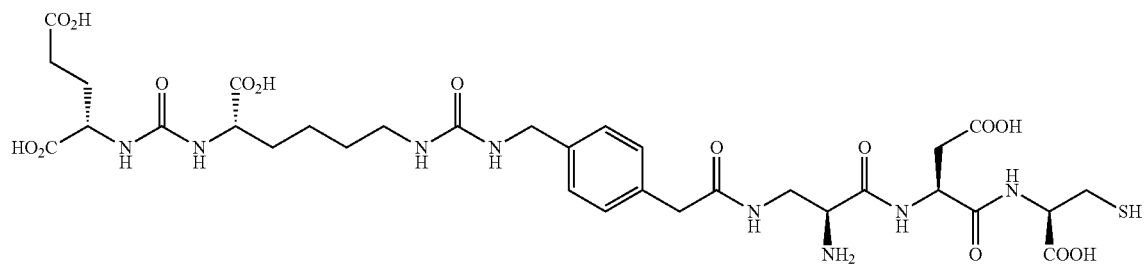
EC1192
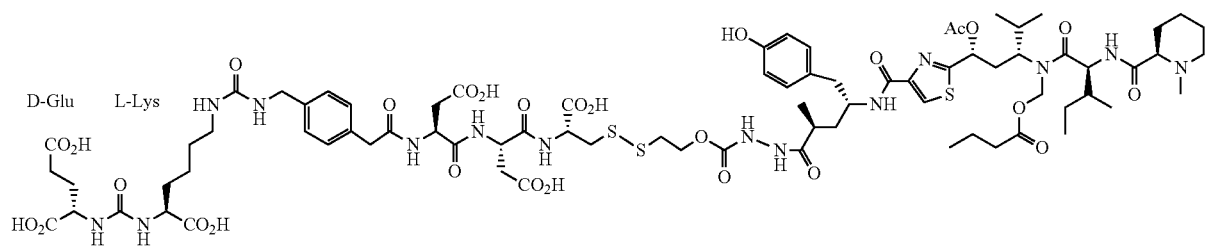
(C78H112N14O28S3. Exact Mass: 1788.69, Mol. Wt.: 1790.00
EC1197
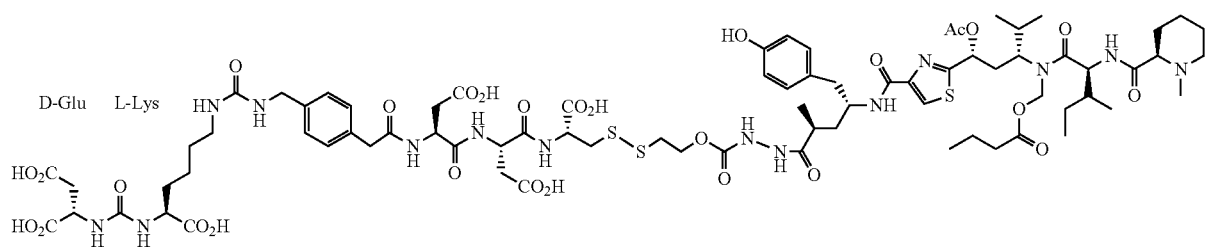
(C77H110N14O28S3. Exact Mass: 1774.68, Mol. Wt.: 1775.97)
EC1241
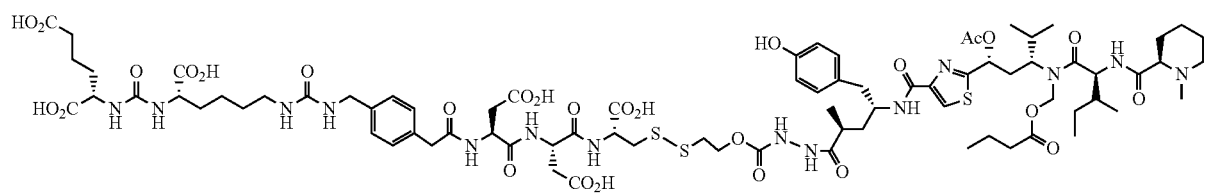
(C79H114N14O28S3. Exact Mass: 1802.71, Mol. Wt.: 1804.03)
EC1268
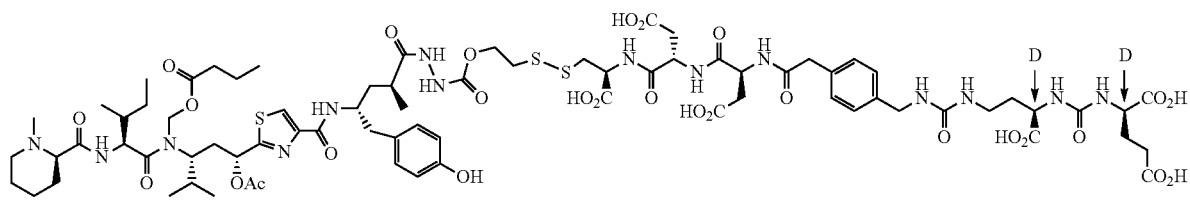
(C78H112N14O28S3. Exact Mass: 1788.69, Mol. Wt.: 1790.00)

-continued
EC1269
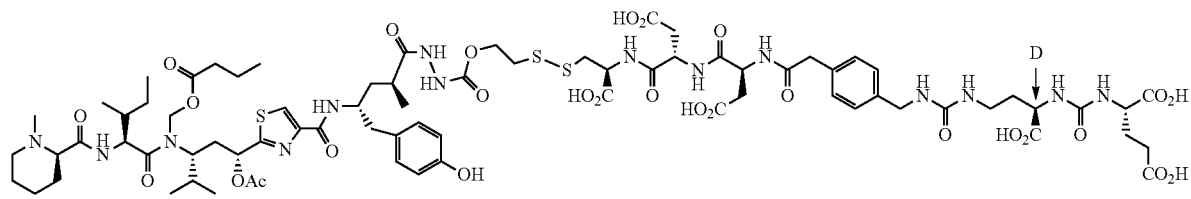
(C78H112N14O28S3. Exact Mass: 1788.69, Mol. Wt.: 1790.00)
EC1308
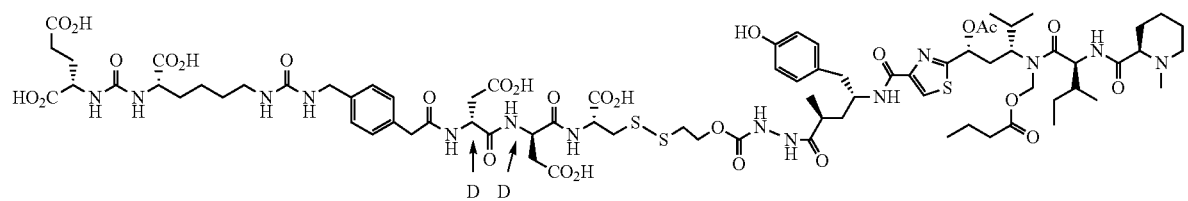
(C78H112N14O28S3. Exact Mass: 1788.6933, Mol. Wt.: 1789.9959)
EC1309
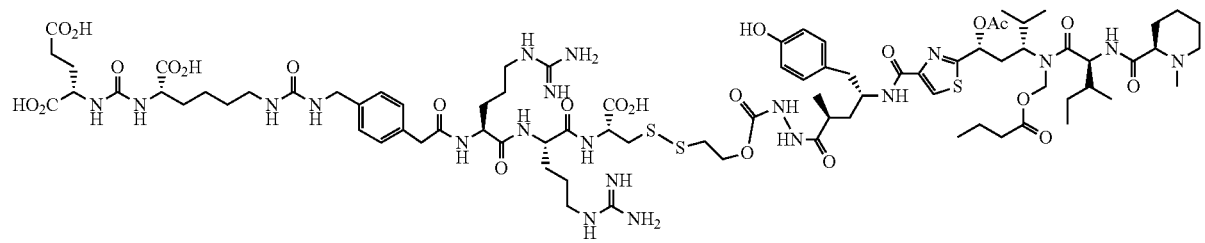
EC1310
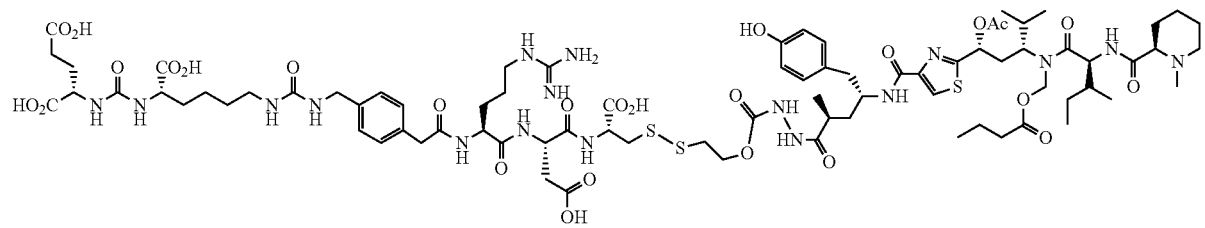
EC1385
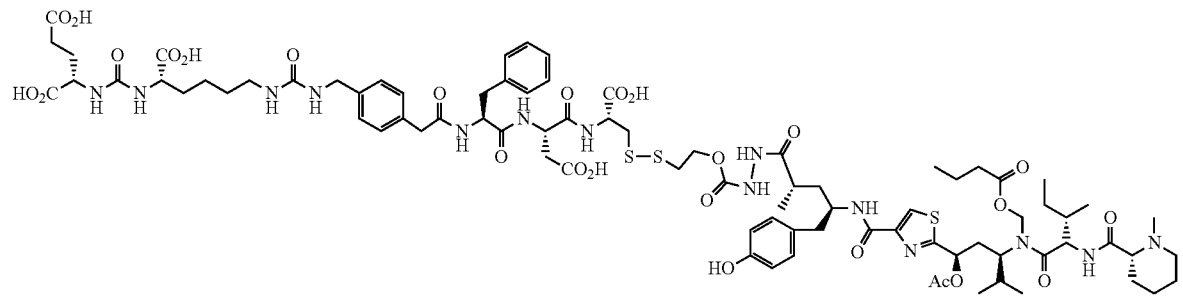
EC1385
C83H116N14O26S3
Exact Mass: 1820.7347

-continued
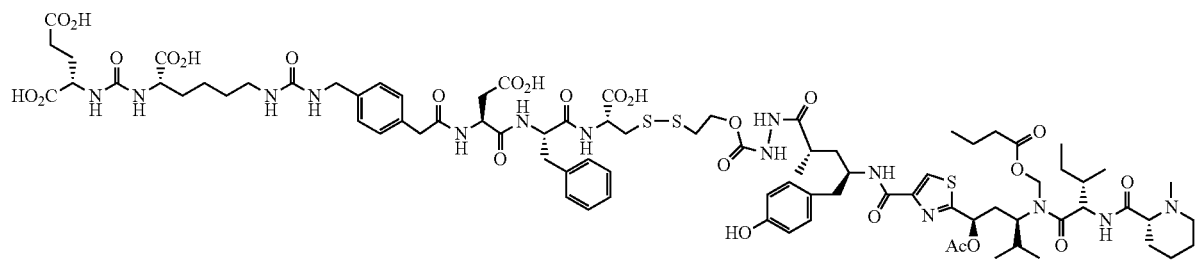
EC1386
C₈₃H₁₁₆N₁₄O₂₆S₃
Exact Mass: 1820.74
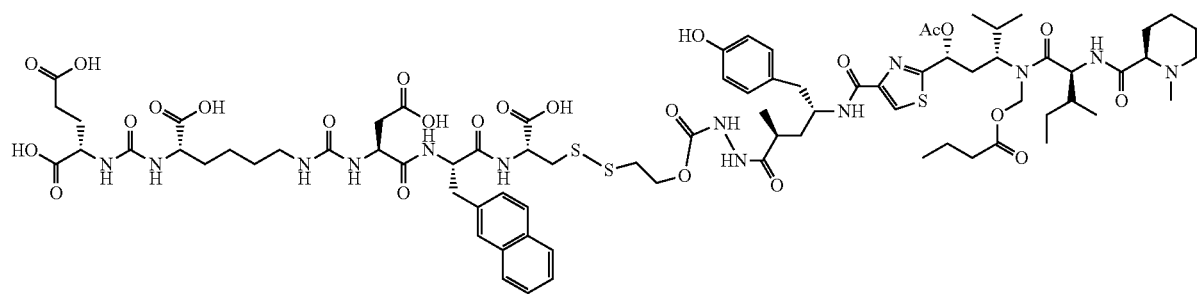
EC1387
Exact Mass: 1723.68
Mol. Wt.: 1724.97
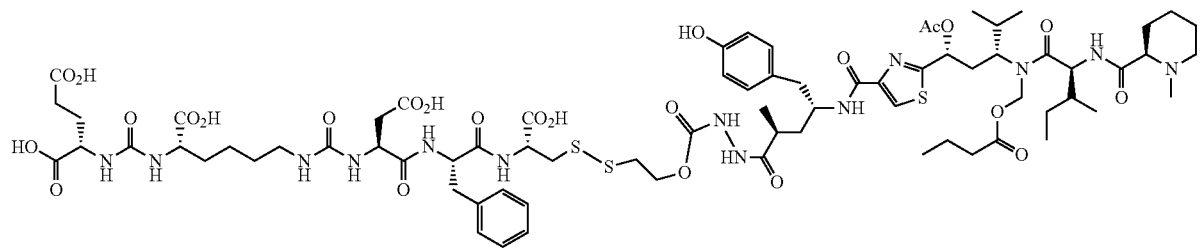
EC1388
Exact Mass: 1679.67
Mol. Wt.: 1674.91
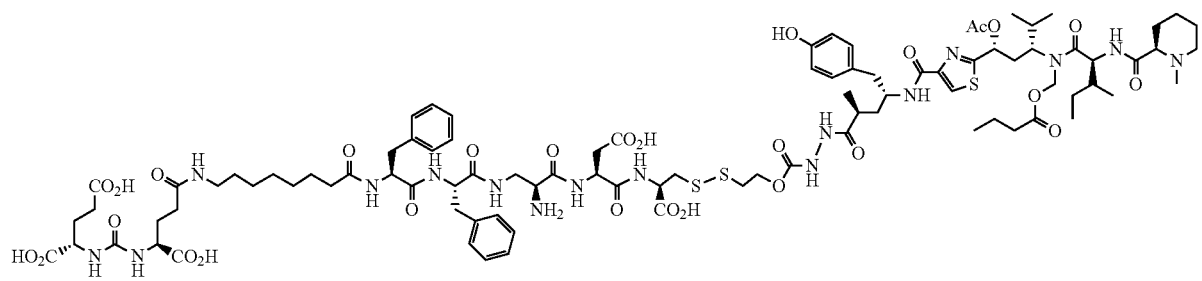
EC1437
C₉₂H₁₃₂N₁₆O₂₈S₃
Exact Mass: 2004.86
Mol. Wt.: 2006.32

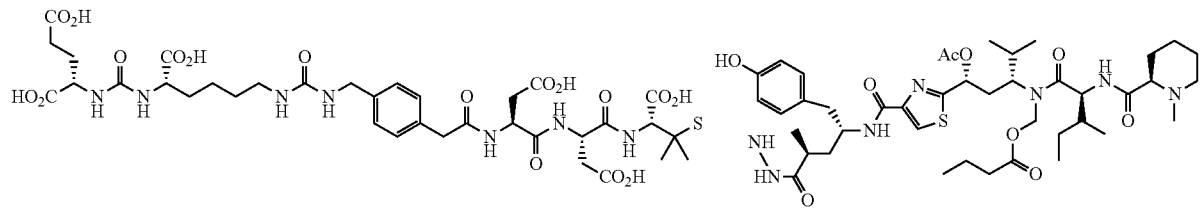
EC1452
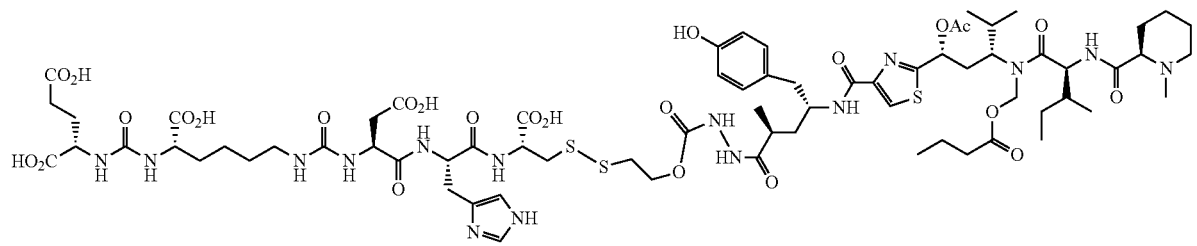
EC1550
Chemical Formula: $C_{71}H_{105}N_{15}O_{25}S_3$
Exact Mass: 1663.66
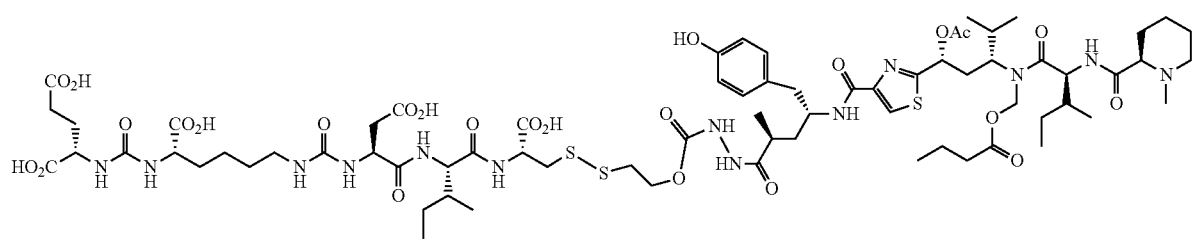
EC1551
Chemical Formula: $C_{71}H_{109}N_{13}O_{25}S_3$
Exact Mass: 1639.66
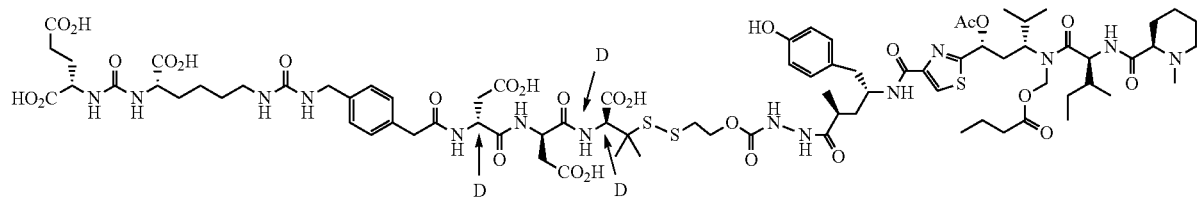
($C_{78}H_{112}N_{13}O_{28}S_3$, Exact Mass: 1788.69, Mol. Wt.: 1790.00)
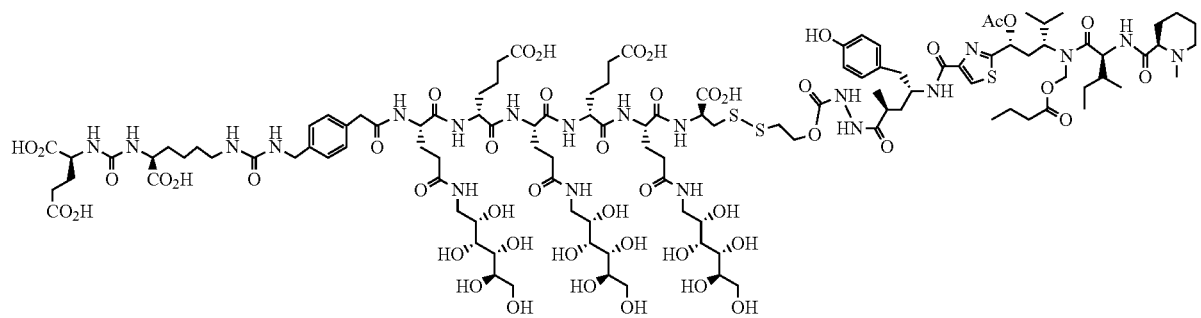

-continued

EC1677

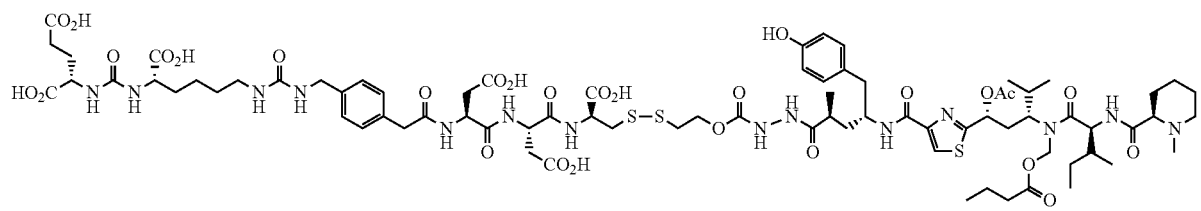

(C78H114N14O27S3, Exact Mass: 1774.71, Molecular Weight: 1776.01)

EC1718

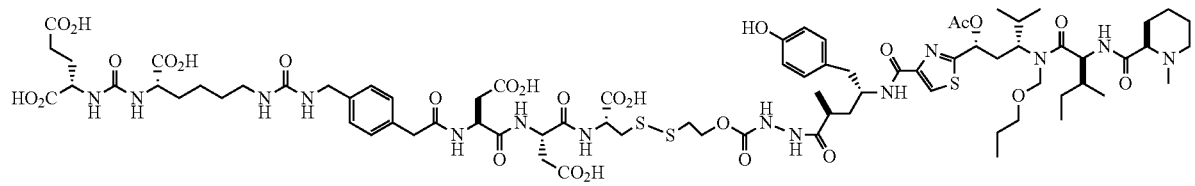

(C77H112N14O27S3, Exact Mass: 1760.70, Mol. Wt.: 1761.99)

EC1719

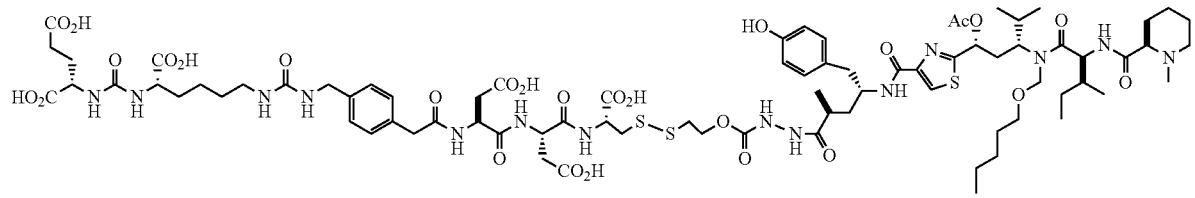

(C79H116N14O27S3, Exact Mass: 1788.73, Mol. Wt.: 1790.04)

EC1720

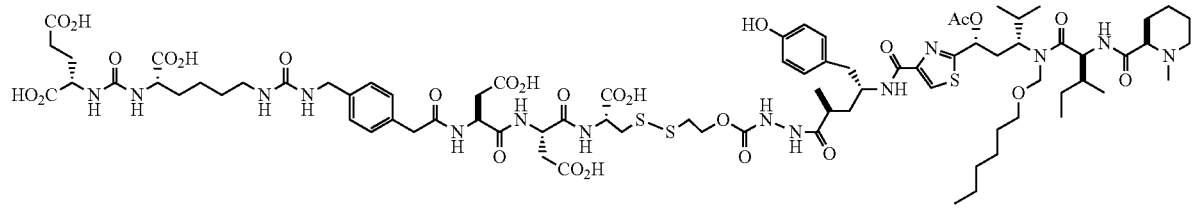

(C80H118N14O27S3, Exact Mass: 1802.75, Mol. Wt.: 1804.07)

EC1721

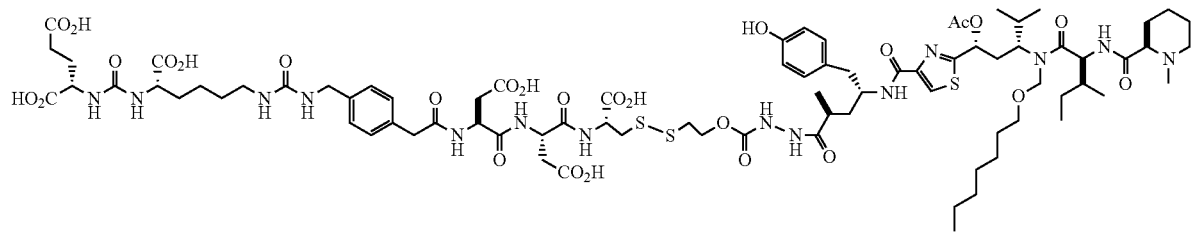

(C81H120N14O27S3, Exact Mass: 1816.76, Mol. Wt.: 1818.09)

Method Example. PSMA relative affinity assay. LNCaP cells are seeded in 12-well Corning Cell-BIND plates and allowed to form adherent monolayers overnight in RPMI/HIFCS. Spent incubation media is replaced with RPMI supplemented with 10% HIFCS and containing a standard PSMA binding ligand, such as 100 nM of 3H-PMPA or a competing compound, such as EC0652, Re-EC652, or $^{99m}$Tc-EC0652, in the absence and presence of increasing concentrations of test compound, such as unlabeled PMPA, or a compound described herein, such as EC1169 or EC1568, a negative control intermediate lacking a PSMA binding ligand which is used as a negative control. Cells are incubated for 1 h at 37° C. and then rinsed three times with 0.5 of PBS. Five hundred microliters of 1% sodium dodecylsulfate in PBS are added to each well; after 5 min, cell lysates are collected, transferred to individual tubes or to vials containing 5 mL of scintillation cocktail, and then counted for radioactivity. Cells exposed to only the standard PSMA binding ligand, such as 3H-PMPA, or competing compound, such as $^{99m}$Tc-EC0652, in FFRPMI (no competitor) art designated as negative controls, whereas cells exposed to the standard PSMA binding ligand, such as 3H-PMPA, plus 1 mM unlabeled PMPA or competing compound, such as $^{99m}$Tc-EC0652 plus Re-EC0652, serve as positive controls. Disintegrations per minute (DPMs) measured in the latter samples (representing nonspecific binding of label) are subtracted from the DPM values from all samples. Relative affinities are defined as the inverse molar ratio of compound required to displace 50% of the standard PSMA binding ligand, such as $^3$H-PMPA, or the competing compound, such as $^{99m}$Tc-EC0652, bound to PSMA on LNCaP cells, and the relative affinity of the standard PSMA binding ligand, such as PMPA, or the competing compound, such as Re-EC0652, for PSMA is set to 1.

Method Example. Dose response assay against PSMA+ LNCaP cells. LNCaP cells are seeded in 24-well Corning Cell-BIND plates and allowed to form nearly confluent monolayers overnight in RPMI/HIFCS. Thirty minutes prior to the addition of test compound, such as a compound described herein, spent medium is aspirated from all wells and replaced with fresh RPMI. Following one rinse with 1 mL of fresh RPMI/HIFCS, each well receives 1 mL of media containing increasing concentrations of test compound (four wells per sample). Test compound treated cells are pulsed for 2 h at 37° C., rinsed four times with 0.5 mL of media, and then chased in 1 mL of fresh media up to 70 h. Spent media is aspirated from all wells and replaced with fresh media containing 5 μCi/mL $^3$H-thymidine. Following a further 4 h 37° C. incubation, cells are washed three times with 0.5 mL of PBS and then treated with 0.5 mL of ice-cold 5% trichloroacetic acid per well. After 15 min, the trichloroacetic acid is aspirated and the cells are solubilized by the addition of 0.5 mL of 0.25 N sodium hydroxide for 15 min. Four hundred and fifty microliters of each solubilized sample is transferred to scintillation vials containing 3 mL of Ecolume scintillation cocktail and then counted in a liquid scintillation counter. Final tabulated results are expressed as the percentage of $^3$H-thymidine incorporation relative to untreated controls.

Method Example. Activity in vivo against PSMA+ expressing tumor implanted in mice. Four to seven week-old male nu/nu mice (Harlan Sprague Dawley, Inc., Indianapolis, Ind.) are maintained on a standard 12 h light-dark cycle and fed ad libitum with rodent diet #2918 (Harlan Teklad, Madison, Wis.) for the duration of the experiment. LNCaP cells are grown in RPMI in 10% HIFCS at 37° C., in a 5% $CO_2$/95% air-humidified atmosphere, harvested and resuspended on ice in matrigel solution (50% RPMI+50% matrigel high concentration, BD#354248) to a final concentration of 1×10$^6$ cells/50 μL. Cell solution and injection needles (28 gauge) are kept on ice prior to injection and 50 μL of the cell solution injected in the subcutis of the dorsal medial area. Mice are divided into groups of five, seven, or nine, and freshly prepared test compound solutions are injected through the lateral tail vein under sterile conditions in a volume of 200 μL of phosphate-buffered saline (PBS). Intravenous (i.v.) treatments are typically initiated when the LNCaP tumors are approximately 100-150 mm$^3$ in volume. The mice in the control groups do not receive any treatment. Growth of each s.c. tumor is followed by measuring the tumor three times per week during treatment and twice per week thereafter, until a volume of 1500 mm$^3$ is reached. Tumors are measured in two perpendicular directions using Vernier calipers, and their volumes are calculated as 0.5× L×W$^2$, where L=measurement of longest axis in mm and W=measurement of axis perpendicular to L in mm. As a general measure of gross toxicity, changes in body weights are determined on the same schedule as tumor volume measurements. Maximum % weight loss on any given day due to treatment is determined for each mouse. Survival of animals is monitored daily. Animals that are moribund (or unable to reach food or water) are euthanized by $CO_2$ asphyxiation.

Figure 2:
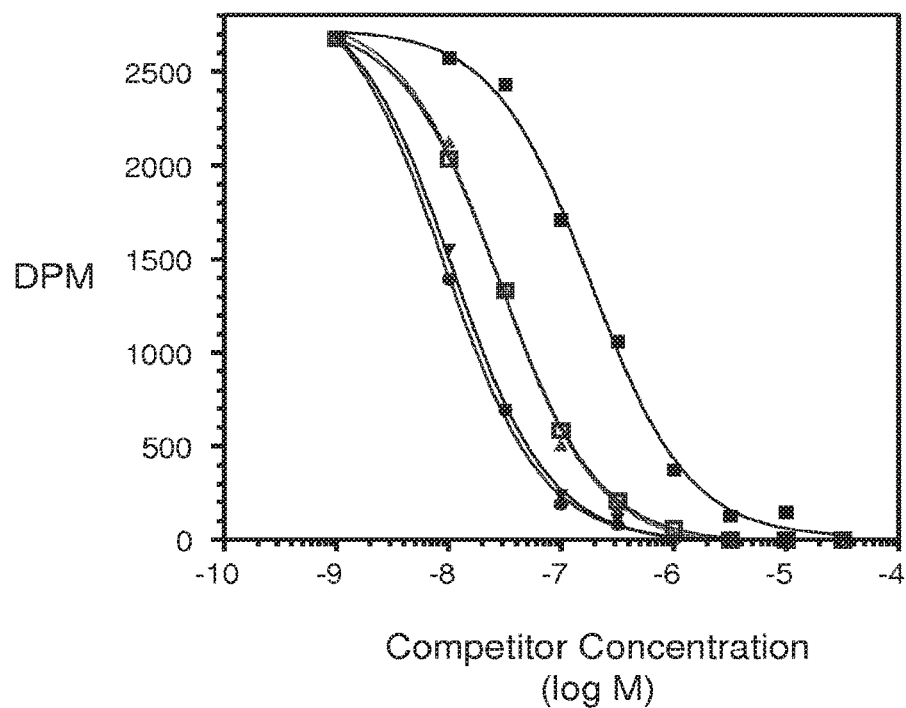
FIG. 2 shows the relative affinity of (■) PMPA, 1.0 (normalized); (●) EC1100, 20×; (▼) EC1168, 17×; (▲) EC1169, 7×; and (□) EC1170, 7× in 10% serum/FDRPMI for PSMA.

Example. Relative affinity of compounds described herein compared to PSMA inhibitors DUPA and PMPA. PMPA is reportedly one of the highest affinity ligands, or the highest affinity ligand, for PSMA. The data in FIG. 1 and FIG. 2 show that compounds described herein exhibit higher affinity for PSMA than does PMPA.

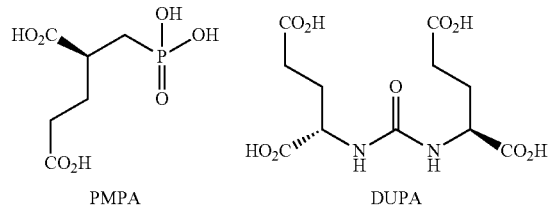

PMPA  DUPA

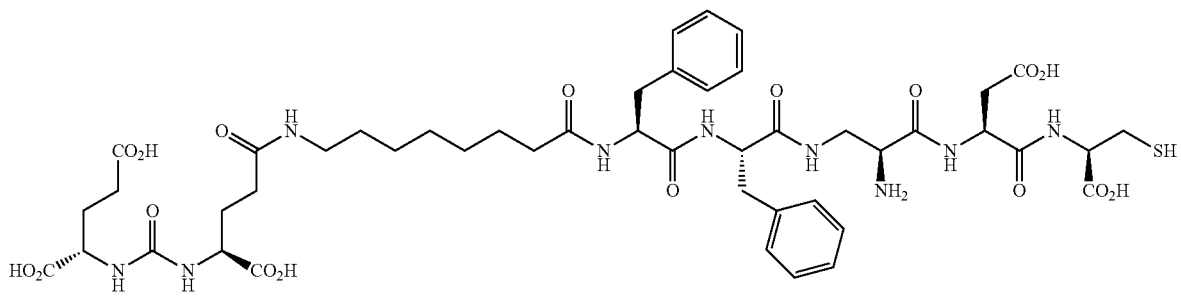

EC0652

It was unexpectedly discovered that the ligands described, herein have a higher affinity for PSMA than the reportedly highest affinity ligand PMPA. In addition, it was unexpectedly discovered herein that conjugates of the ligands described herein had even higher affinity for PSMA.

The binding data for additional illustrative compounds described herein are shown in the following table

| Example | Relative PSMA Binding Affinity (fold over PMPA = 1.0) |
|---|---|
| EC1080 | 6 |
| EC1067 | 30 |
| EC1100 | 20 |
| EC1167 | 11 |
| EC1168 | 17 |
| EC1170 | 7 |
| EC1069 | 22 |
| EC1183 | 9 |
| EC1241 | 1.1 |
| EC1303 | 7 |
| EC1307 | 28 |
| EC1308 | 20 |
| EC1310 | 10 |
| EC1584 | 6 |
| EC1568 (negative control) | 0 |

Figure 3:
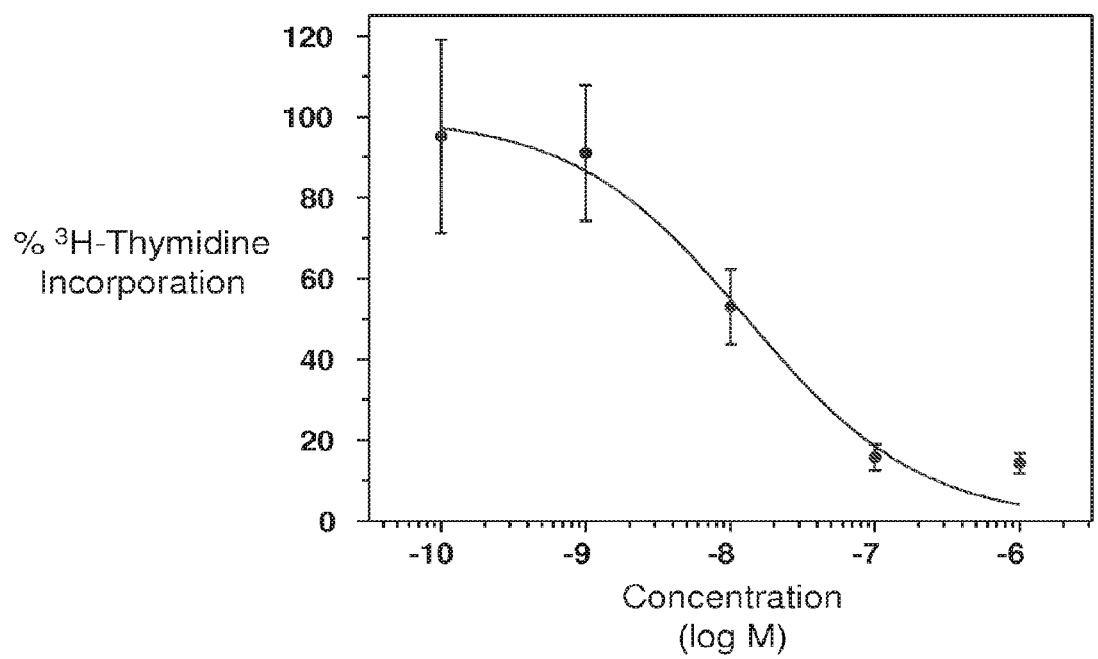
FIG. 3 shows the dose response and IC50 for EC1169 against LNCaP cells (2 h-72 h) as determined by $^3$H-thymidine incorporation cells in vitro.
Figure 4:
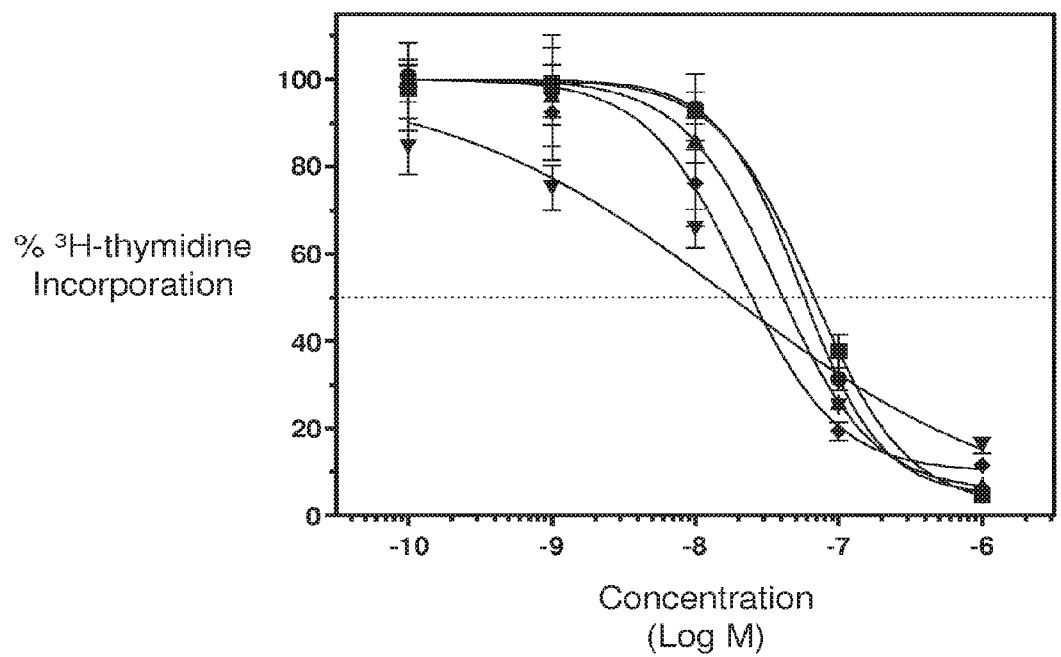
FIG. 4 shows the dose response and IC50 for (▼) EC)718, (◆) EC1677, (▲) EC1719, (●) EC1720, and (■) EC1721 against LNCaP cells (2 h-72 h) as determined by $^3$H-thymidine incorporation cells in vitro.

Example. Dose response of compounds described herein against PSMA+ LNCaP cells. Using a standard $^3$H-thymidine incorporation assay as a measure of cytotoxicity, the data in FIG. 3 show that EC1169 exhibits dose responsive cytotoxicity against cells in vitro with an $IC_{50}$ of 13 nM. The corresponding dose responsive cytotoxicity and $IC_{50}$ values for (▼) EC1718, $IC_{50}$ 17.9 nM; (♦) EC1677, $IC_{50}$ 20.9 nM; (▲) EC1719, $IC_{50}$ 37.5 nM; (●) EC1720, $IC_{50}$ 54.2 nM; (■) EC1721, $IC_{50}$ 65.6 nM are shown in FIG. 4

Example. Additional compounds described herein against LNCaP cells (2 h-72 h) as determined by $^3$H-thymidine incorporation cells in vitro are shown in the following table.

| Example | % $^3$H-thymidine incorporation |
|---|---|
| EC1069 | 13 nM |
| EC1268 | 59.1 |
| EC1385 | 184 |
| EC1386 | 57 |
| EC1387 | 24 |
| EC1388 | 12 |
| EC1437 | 30 |
| EC1550 | 22 |
| EC1551 | 20 |
| EC1452 | 22 |
| EC1584 | 33 |
| EC1588 | 42 |

Figure 5:
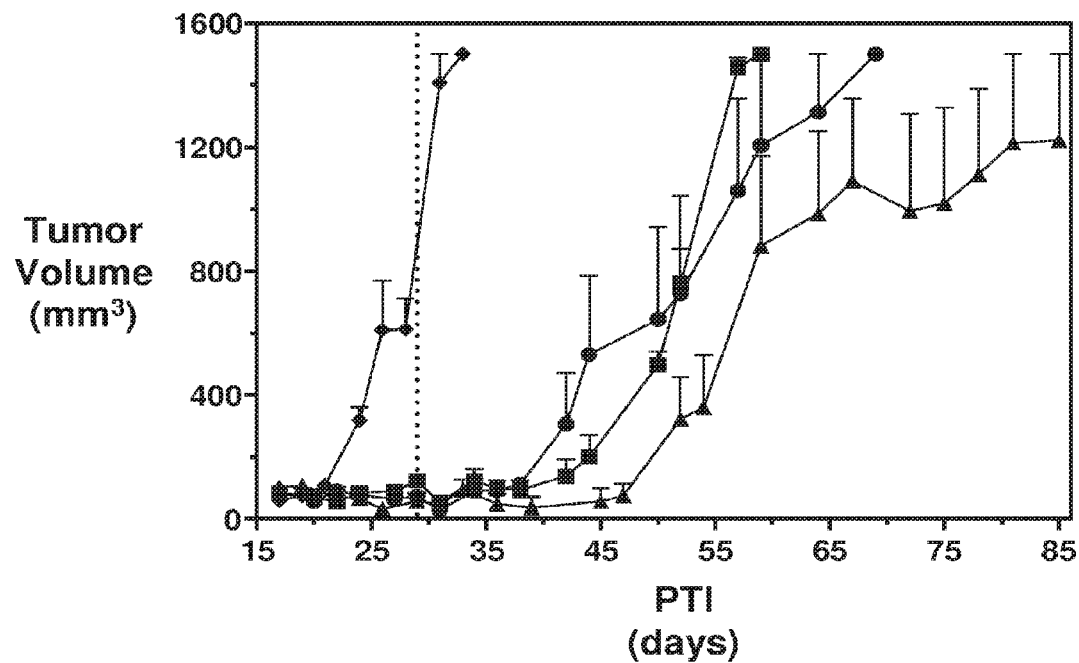
FIG. 5 shows the in vivo efficacy of EC1169 (c), EC1550 (●), and EC1551 (■), each at 2 μmol/kg, TPW (three times per week), 2 weeks, compared against vehicle-treated controls (◆) in treating LNCaP tumor xenografts.

Example. Activity of compounds described herein against PSMA+ tumors in vivo. As shown in FIG. 5 treatment of nude mice bearing PSMA-positive LNCaP human xenografts with EC1169 (c), EC1550 (●), and EC1551 (■), each at 2 µmol/kg, TIW, 2 weeks, leads to complete responses in all tested animals. Each compound was compared against vehicle-treated controls (♦). A complete response is observed when the tumor does not appear to have any net growth during the treatment period of 14 days (the vertical dotted line indicates the last treatment day). As described herein, it is to be understood that the implants comprise the cancer cells in a matrix (100-150 mm$^3$ total volume). Because the matrix remains during the entire observation period, a decrease in the size of the tumor cannot always be determined by external measurement. It was also surprisingly found that, treatment with compounds described herein leads to cure. For example, EC1169 leads to cure in 2/7 tested animals. A cure is observed when the tumor does not appear to grow during the entire observation period of 85 days. The data shown in FIG. 5 are the average of the measurements for each cohort. Therefore, it is to be understood that the increase in tumor volume beginning at about day 40-45 represents regrowth in the remaining test animals.

Figure 6:
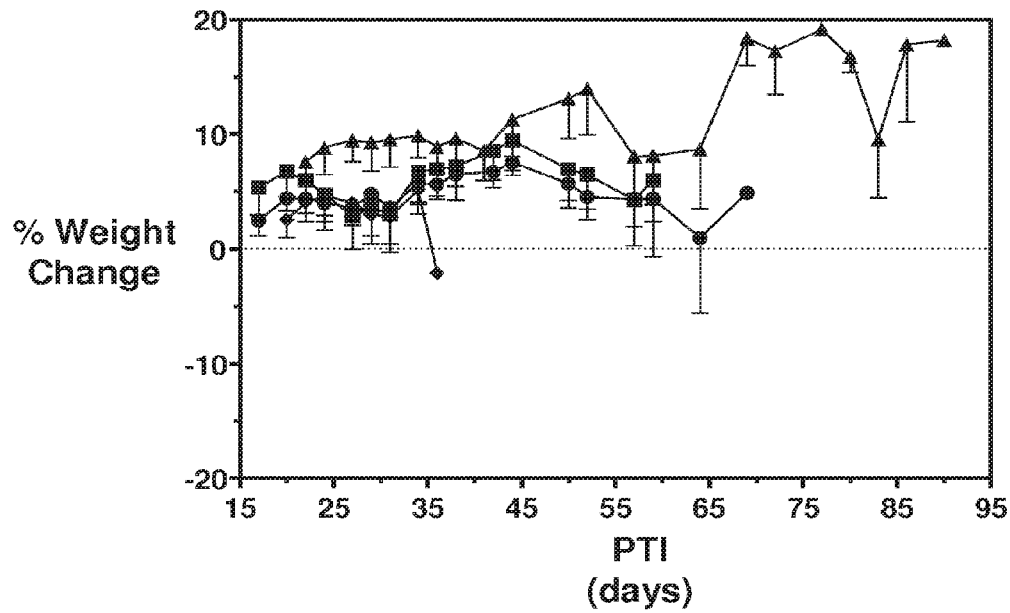
FIG. 6 shows that EC1169 (c), EC1550 (●), and EC1551 (■), each at 2 μmol/kg, TIW, 2 weeks, compared against vehicle-treated controls (◆) do not exhibit gross animal toxicity.

Example. Gross toxicity of compounds described herein. As shown in FIG. 6, the observed efficacy of EC1169 (c), EC1550 (●), and EC1551 (■), occurred in the absence of weight loss or major organ tissue degeneration.

Figure 7:
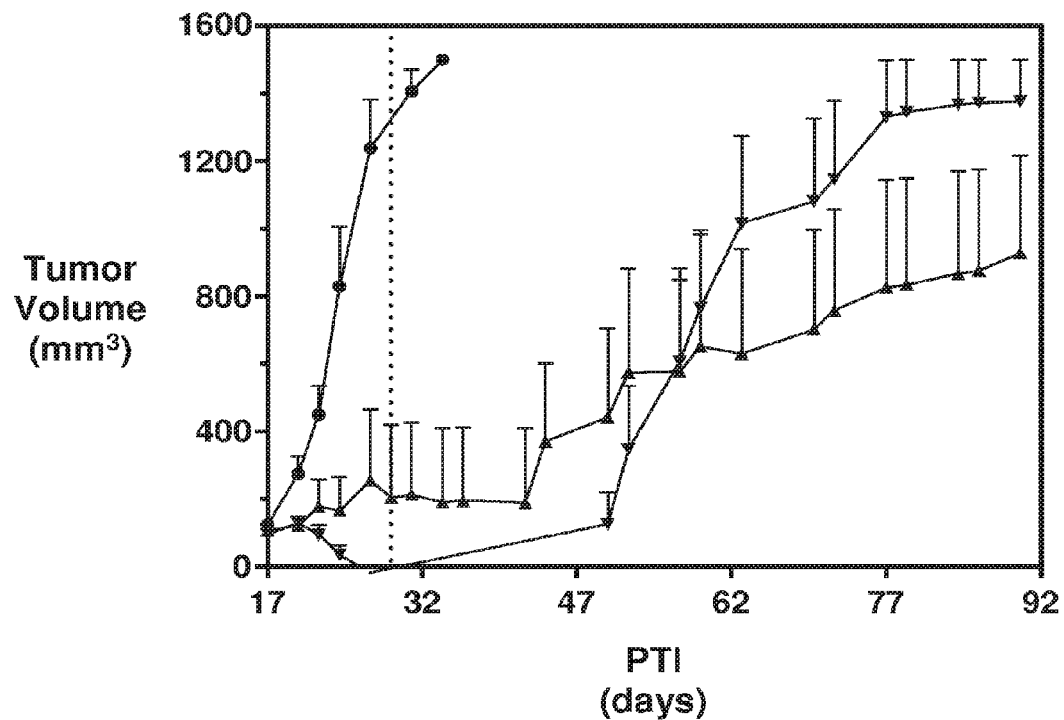
FIG. 7 shows the in vivo efficacy of EC1584 (▼) and EC1588 (▲) each at 2 μmol/kg, TIW, 2 weeks, compared against vehicle-treated controls (●) in treating LNCaP tumor xenografts.

Example. Activity of compounds described herein against PSMA+ tumors in vivo. Similarly, as shown in FIG. 7, treatment of nude mice bearing PSMA-positive LNCaP human xenografts with EC1584 (▼) and EC1588 (▲), each at 2 µmol/kg, TIW, 2 weeks, leads to complete responses in all tested animals. Each compound was compared against vehicle-treated controls (●). It was also surprisingly found that treatment with EC1588 leads to cure in 3/7 tested animals.

Figure 8:
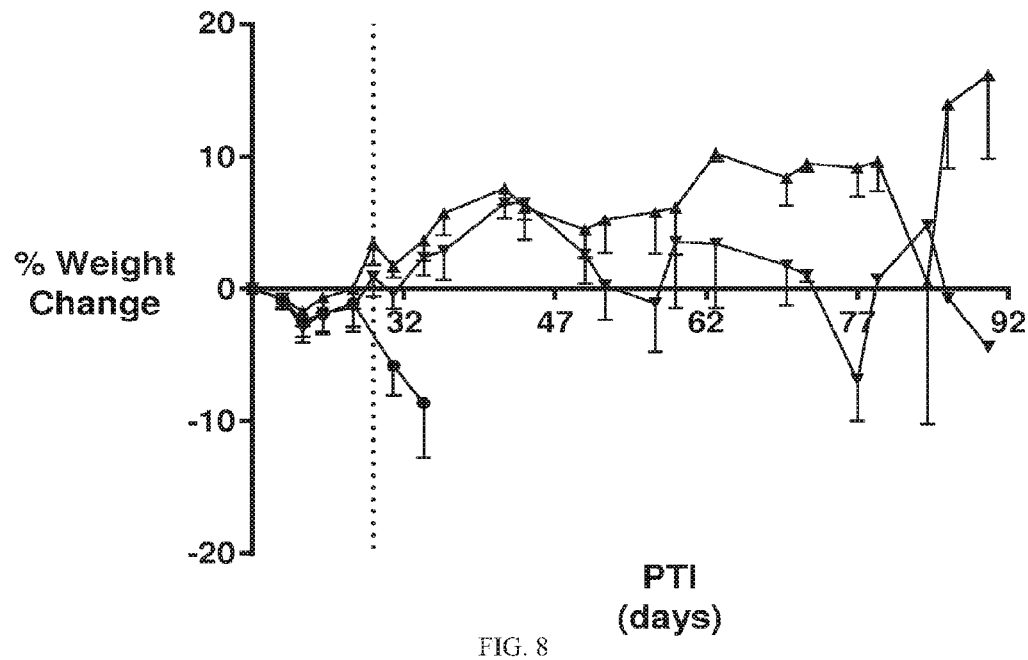
FIG. 8 shows that EC1584 (▼) and EC1588 (▲), each at 2 μmol/kg, TIW, 2 weeks, compared against vehicle-treated controls (●) do not exhibit gross animal toxicity.

Example. Gross toxicity of compounds described herein. As shown in FIG. 8, the observed efficacy of EC1584 (▼) and EC1588 (▲) occurred in the absence of weight loss or major organ tissue degeneration.

Figure 9:
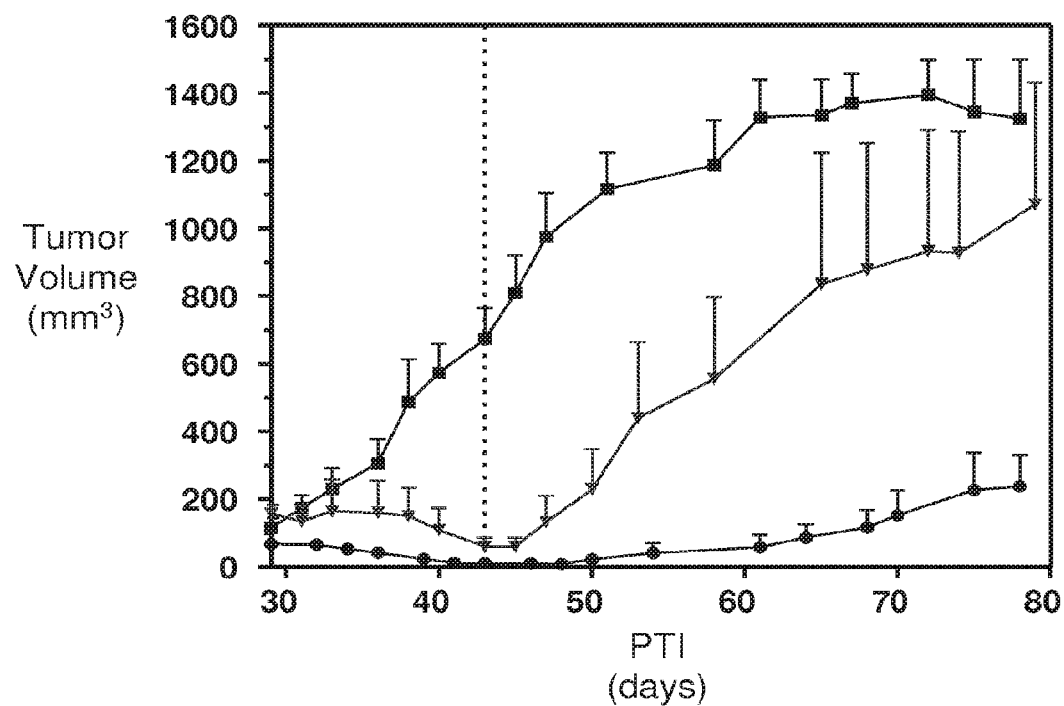
FIG. 9 shows the in vivo efficacy of EC1169 (●) at 2 μmol/kg, TIW, 2 weeks, compared to docetaxel, at 10 mg/kg, BIW, 2 weeks, MTD (▼), and each compared to vehicle-treated control (■) in treating LNCaP tumor xenografts.
Figure 10:
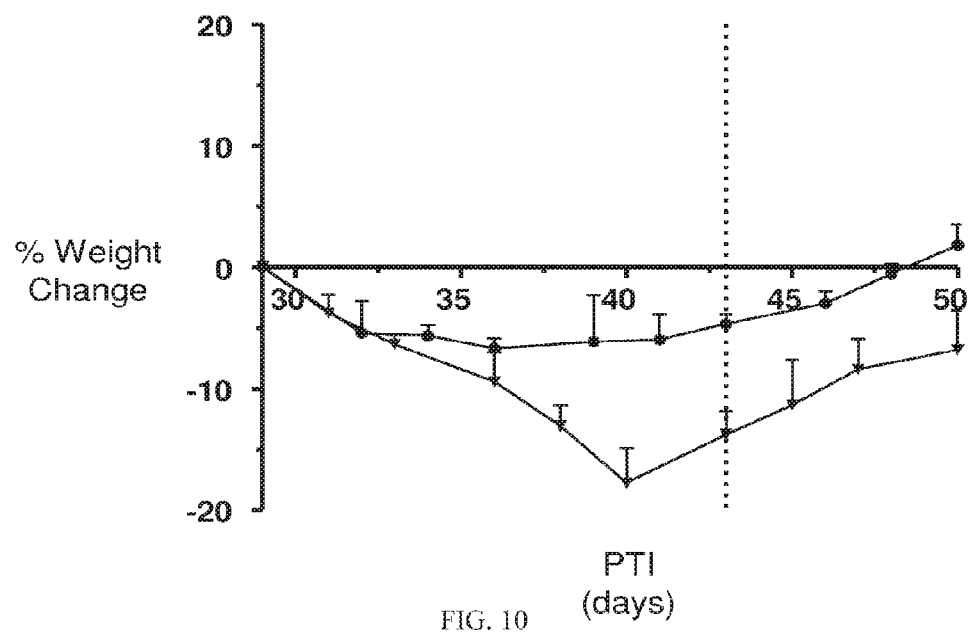
FIG. 10 shows that of EC1169 (●) administered at 2 μmol/kg, TIW, 2 weeks, exhibits substantially less gross animal toxicity compared to docetaxel, administered at 10 mg/kg, BIW, 2 weeks, MTD (▼).

Example. Activity of compounds described herein against PSMA+ tumors compared to conventional chemotherapeutic agents. As shown in FIG. 9, treatment of LNCaP-tumor bearing mice with docetaxel (the most active chemotherapeutic agent approved for prostate cancer) at 10 mg/kg, BIW, 2 weeks, MTD (▼), was found to produce only modest anti-tumor activity, and showed only 1/4 cures, even when administered at its MTD. In addition, as shown in FIG. 10, that modest observed docetaxel efficacy was accompanied by high gross toxicity, as evidenced by severe weight loss (18%). EC1169, administered at 2 µmol/kg, TIW, 2 weeks (●), is more active and less toxic than docetaxel against PSMA+ LNCaP tumors. FIG. 9 shows that treatment with EC1169 leads to a complete response in all test animals, and resulted in 2/5 cures. FIG. 10 also shows that the higher efficacy displayed by EC1169 was not accompanied by substantially lower toxicity than docetaxel, providing a significantly wider therapeutic window. The efficacy of each compound was compared to vehicle-treated control (■).

Figure 11:
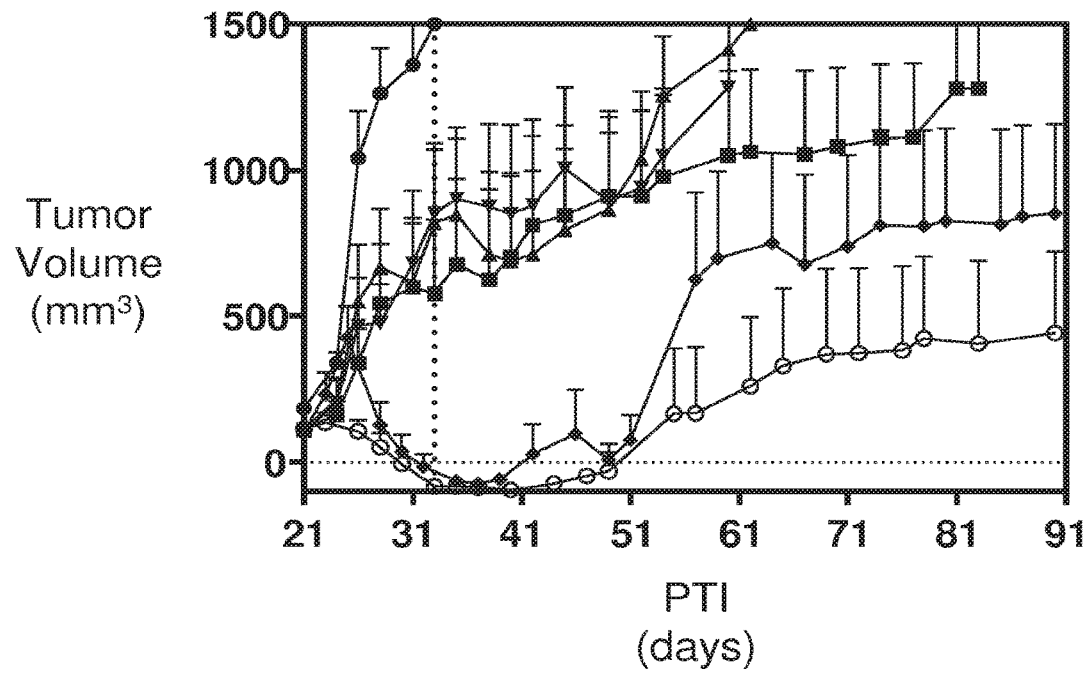
FIG. 11 shows the in vivo efficacy of (■) EC1718; (▲) EC1720; (▼) EC1721; (◆) EC1719; and (○) EC1677, each administered at 2 μmol/kg, TIW, 2 weeks; compared to (●) vehicle-treated control in treating LNCaP tumor xenografts.
Figure 12:
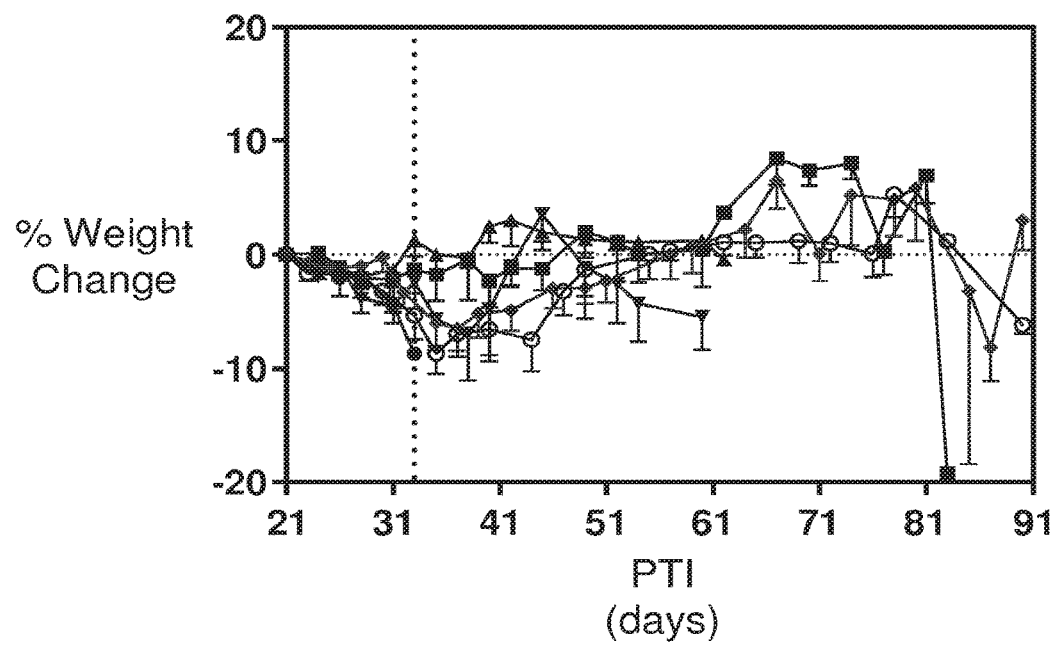
FIG. 12 shows that (■) EC1718; (▲) EC1720; (▼) EC1721; (◆) EC1719; and (○) EC1677; compared to (●) vehicle-treated control, do not exhibit gross animal toxicity.

Example. The in vivo efficacy of (■) EC1718; (▲) EC1720; (▼) EC1721; (♦) EC1719; and (○) EC1677; compared to (●) untreated control is shown in FIG. 11. All compounds were administered at 2 µmol/kg, TIW for 2 weeks, beginning on day 21 post tumor implant (PTI). The dotted line indicates the final treatment day. The data indicate that the compounds described herein are efficacious in decreasing tumor growth in vivo compared to untreated animals. In addition, (■) EC1718 lead to 1/7 cures; (▼) EC1721 lead to 1/7 cures; (♦) EC1719 lead to 2/7 cures; and (○) EC1677 lead to 4/7 cures, where regrowth of the tumor in those animals was not observed during the observation period. In addition, the compounds described herein do not show gross toxicity to the test animals, as shown in FIG. 12. Without being bound by theory, it is believed herein that the weight change observed in FIG. 12 for EC1718 at about day 81 is due to the effects of the tumor size.

Example. Specificity of compounds described herein. PSMA-negative KB tumors did not appreciably respond to EC1169 therapy, supporting the conclusion that the compounds described herein exhibit target specificity for PSMA-expressing cells.

Example. Hematological Toxicity. Conjugates described herein demonstrate significantly improved hematological toxicity. EC1169, EC1584, and EC1588 were administered to rats i.v. at 0.33 and 0.51 µmol/kg, twice per week (BIW), for 2 weeks. The hematological toxicity in red blood cells and white blood cells was significantly lower than untreated controls.

What is claimed is:

1. A method of treating prostate cancer in a patient, comprising administering a therapeutically effective amount of a conjugate having a formula

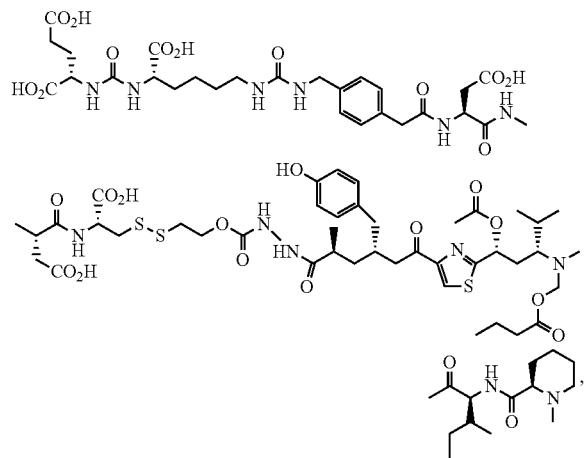

or a pharmaceutically acceptable salt thereof.

2. A method of treating prostate cancer in a patient, comprising administering a composition comprising a therapeutically effective amount of a conjugate having a formula 3. The method of claim 2, wherein the patient is a human.

4. The method of claim 2, wherein the composition is administered to the patient in an oral dosage form.

5. The method of claim 4, wherein the oral dosage form is selected from the group consisting of a tablet, a capsule, an elixir, and a syrup.

6. The method of claim 2, wherein the composition is administered to the patient in a parenteral dosage form.

7. The method of claim 6, wherein the parenteral dosage form is administered to the patient through a route selected from the group consisting of intravenous, intraarterial, intraperitoneal, epidurial, intraurethral, intrasternal, intramuscular, and subcutaneous.

8. The method of claim 2, wherein the therapeutically effective amount is from about 1 µg/kg to about 1 g/kg.

9. The method of claim 2, wherein the therapeutically effective amount is administered in a single dosage.

10. The method of claim 2, wherein the therapeutically effective amount is administered in a divided dosage.

11. The method of claim 2, wherein the therapeutically effective amount is administered once daily.

12. The method of claim 2, wherein the therapeutically effective amount is administered twice daily.

13. The method of claim 2, wherein the therapeutically effective amount is administered thrice daily.

14. The method of claim 2, wherein the therapeutically effective amount is administered once a week.

15. The method of claim 2, wherein the therapeutically effective amount is administered once a month.

16. The method of claim 2, wherein the therapeutically effective amount is administered once a quarter.

17. The method of claim 2, wherein the composition further comprises a pharmaceutically-acceptable carrier, a pharmaceutically-acceptable adjuvant, a pharmaceutically-acceptable vehicle, a pharmaceutically-acceptable excipient, or a combination thereof.

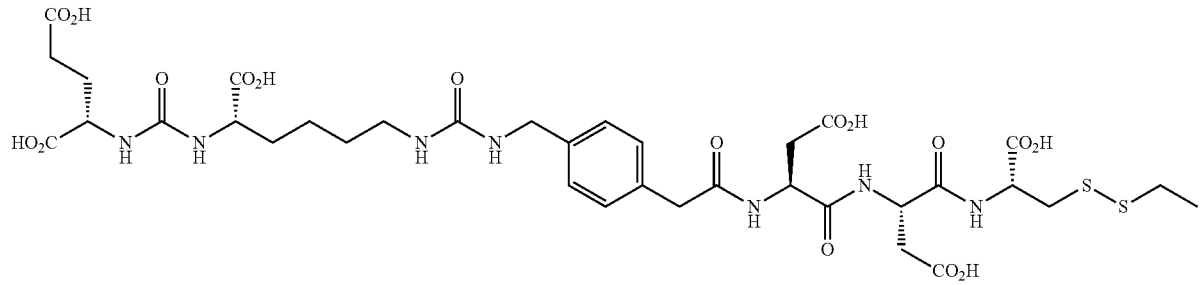

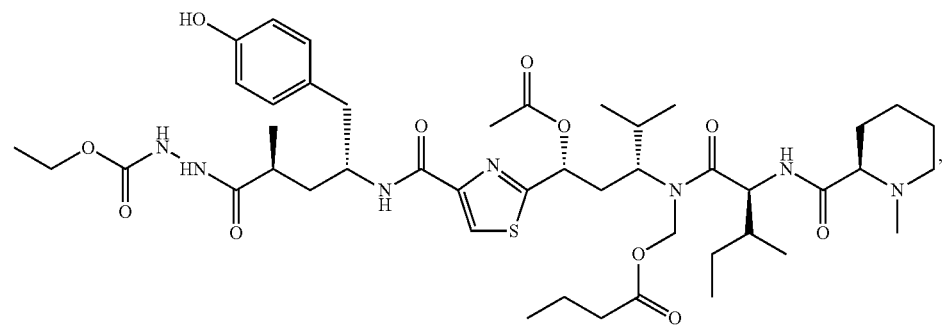

or a pharmaceutically acceptable salt thereof.

18. The method of claim 2, wherein the composition is in a form selected from the group consisting of a tablet, a pill, a powder, a lozenge, a sachet, a cachet, an elixir, a suspension, an emulsion, a solution, a syrup, a solid aerosol, an aerosol in a liquid medium, an ointment, a soft gelatin capsule, a hard gelatin capsule, and a suppository.

19. The method of claim 18, wherein the composition is in a form selected from the group consisting of a sterile injectable solution and a sterile packaged powder.

* * * * *